United States Patent
Nath et al.

(10) Patent No.: US 8,114,619 B2
(45) Date of Patent: Feb. 14, 2012

(54) METHODS FOR DIAGNOSIS AND OPTIMIZING TREATMENT OF MULTIPLE SCLEROSIS

(75) Inventors: Avindra Nath, Baltimore, MD (US); Caroline F Anderson, Columbia, MD (US); David Irani, Baltimore, MD (US); Robert J Cotter, Baltimore, MD (US); Joseph P Steiner, Mount Airy, MD (US); Norman Haughey, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 1015 days.

(21) Appl. No.: 11/857,742

(22) Filed: Sep. 19, 2007

(65) Prior Publication Data

US 2010/0137420 A1 Jun. 3, 2010

Related U.S. Application Data

(63) Continuation-in-part of application No. PCT/US2007/064532, filed on Mar. 21, 2007.

(60) Provisional application No. 60/784,425, filed on Mar. 21, 2006.

(51) Int. Cl.
G01N 33/53 (2006.01)
(52) U.S. Cl. ...................................... 435/7.92
(58) Field of Classification Search .................. None
See application file for complete search history.

(56) References Cited

U.S. PATENT DOCUMENTS

| | | | |
|---|---|---|---|
| 3,817,837 A | 6/1974 | Rubenstein et al. |
| 3,850,752 A | 11/1974 | Schuurs et al. |
| 3,939,350 A | 2/1976 | Kronick et al. |
| 3,996,345 A | 12/1976 | Ullman et al. |
| 4,275,149 A | 6/1981 | Litman et al. |
| 4,277,437 A | 7/1981 | Maggio |
| 4,366,241 A | 12/1982 | Tom et al. |
| 4,472,509 A | 9/1984 | Gansow et al. |
| 4,664,911 A | 5/1987 | Uhr et al. |
| 4,792,447 A | 12/1988 | Uhr et al. |
| 5,021,236 A | 6/1991 | Gries et al. |
| 5,045,451 A | 9/1991 | Uhr et al. |
| 5,225,538 A | 7/1993 | Capon et al. |
| 5,578,706 A | 11/1996 | Ghetie et al. |
| 5,686,072 A | 11/1997 | Uhr et al. |
| 5,707,632 A | 1/1998 | Williams et al. |
| 5,726,044 A | 3/1998 | Lo et al. |
| 5,767,072 A | 6/1998 | Vitetta et al. |
| 5,925,351 A | 7/1999 | Browning et al. |
| 6,406,697 B1 | 6/2002 | Capon et al. |
| 6,656,728 B1 | 12/2003 | Kavanaugh et al. |

OTHER PUBLICATIONS

Shimode et al. Diagnosis of cerebral amyloid angiopathy by enzyme-linked immunosorbent assay of cystatin C in cerebrospinal fluid. Stroke. Jul. 1991;22(7):860-6.*

Abrahamson et al., "Identification of the Probable Inhibitory Reactive Sites of the Cysteine Proteinase Inhibitors Human Cystatin C and Chicken Cystatin," The Journal of Biological Chemistry, 262(20):9688-9694 (1987).
Abrahamson et al., "Role of the $N$-terminal segment in the inhibition of human cysteine proteinases adn in its inactivation by leucocyte elastase," Biochem. J., 273:621-626 (1991).
Balaji et al., "Surface Cathepsin B Protects Cytotoxic Lymphocytes from Self-destruction after Degranulation," J. Exp. Med., 196(4):493-503 (2002).
Barrett et al., "L-$trans$-Epoxysuccinyl-leucylamido(4-guanidino)butane (E-64) and its analogues as inhibitors of cysteine proteinases including cathepsins B, H and L," Biochem. J., 201:189-198 (1982).
Bever et al., "Increased cathespin B activity in multiple sclerosis brain," Journal of the Neurological Sciences, 131:71-73 (1995).
Bollengier, F., "Cystatin C, Alias Post-γ-Globulin: A Marker for Multiple Sclerosis?" J. Clin. Chem. Clin. Biochem., 25:589-593 (1987).
Carrette et al., "Truncated cystatin C in cerebrospiral fluid: Technical artefact or biological process?," Proteomics, 5:3060-3065 (2005).
Del Boccio et al., "Cleavage of Cystatin C Is Not Associated with Multiple Sclerosis," Annals of Neurology, 62(2):201-204 (2007).
Fainardi et al., "Cerebrospinal fluid and serum levels and intrathecal production of active matrix metalloproteinase-9 (MMP-9) as markers of disease activity in patients with multiple sclerosis," Multiple Sclerosis, 12:294-301 (2006).
Gerhartz et al., "Physico-Chemical Properties of the N-Terminally Truncated L68Q Cystatin C Found in Amyloid Deposits of Brain Haemorhage Patients," Biol. Chem., 383:301-305 (2002).
Greiner et al., "Activity and subcellular distribution of cathespins in primary human monocytes," Journal of Leukocyte Biology, 73:235-242 (2003).
Hansson et al., "Cystatin C in Cerebrospinal Fluid and Multiple Sclerosis," Annals of Neurology, 62(2):193-196 (2007).
Irani et al., "Cleavage of Cystatin C in the Cerebrospinal Fluid of Patients with Multiple Sclerosis," Ann Neurol, 59:237-247 (2006).
Johansson et al., "A Peptidyl Derivative Structurally Based on the Inhibitory Center of Cystatin C Inhibits Bone Resorption In Vitro," Bone, 26(5):451-459 (2000).
Kanesaka et al., "Serum matrix metalloproteinase-3 levels correlate with disease activity in relapsing-remitting multiple sclerosis," J. Neurol Neurosug. Psychiatry, 77:185-188 (2006).
Lenarcic et al., "Inactivation of human cystatin C and kininogen by human cathepsin D," FEBS, 280(2):211-215 (1991).
Matsumoto et al., "Structural Basis of Inhibition of Cysteine Proteases by E-64 and Its Derivatives," Biopolymers, 51:99-107 (1999).
Nagai et al., "Cathepsin B and H activities and cystatin C concentrations in cerebrospinal fluid from patients with leptomeningeal metastasis," Clinica Chimica Acta, 329:53-60 (2003).

(Continued)

*Primary Examiner* — Daniel E Kolker
*Assistant Examiner* — Gregory S Emch
(74) *Attorney, Agent, or Firm* — Foley Hoag LLP

(57) ABSTRACT

Biological markers for multiple sclerosis, and their use in the diagnosis and prognosis of the disease, are described. Also described are methods for treating multiple sclerosis by administering an inhibitor of cathepsin B activity or a neuroprotective composition comprising a modified terpenoid compound. Also described are isolated polypeptide biomarkers, polynucleotides encoding the polypeptide biomarkers, and antibodies that bind specifically to the polypeptide biomarkers. Further described are kits that include the above-mentioned isolated polypeptide biomarkers, the polynucleotides encoding them, or specific antibodies against the polypeptide biomarkers.

5 Claims, 19 Drawing Sheets

OTHER PUBLICATIONS

Nakashima et al., "Alteration of Cystatin C in the Cerebrospinal Fluid of Multiple Sclerosis," Annals of Neurology, 62(2):197-200 (2007).

Nath et al., "Cleavage of Cystatin C in CSF is a Biomarker of Multiple Sclerosis," Neurology, 64(6): Abstract, Mar. 22, 2005, abstract No. S56.002.

Roberts, R., "Lysomal Cysteine Proteases: Structure, Function and Inhibition of Cathepsins," Drug News Perspect., 18(10):605-614 (2005).

Sanchez et al., "Cystatin C as a potential cerebrospinal fluid marker for the diagnosis of Creutzfeldt-Jakob disease," Proteomics, 4:2229-2233 (2004).

Shlipak et al., "Cystatin C and the Risk of Death and Cardiovascular Events among Elderly Persons," N. Engl. J. Med., 352(20):2049-2060 (2005).

International Search Report dated Nov. 30, 2007 for PCT/US2007/064532.

Bergers, et al.; "Effects of Angiogenesis Inhibitors on Multistage Carcinogenesis in Mice," Science 284:808-12 (Apr. 30, 1999).

Caporello, et al.; "The immunophilin ligand GP11046 protects neurons from the lethal effects of the HIV-1 proteins gp120 and Tat by modulating endoplasmic reticulum calcium load," J. Neurochem., 98(1):146-155 (2006).

Carrette, et al.; "A panel of cerebrospinal fluid potential biomarkers for the diagnosis of Alzheimer's disease," Proteomics 3:1486-1494 (2003).

Dumont, et al., "Proteomic analysis of cerebrospinal fluid from multiple sclerosis patients," Proteomics 4:2117-2124 (2004).

Duncan, et al.; "The binding site for C1q on IgG," Nature 332:738-740 (1988).

Frohman, et al.; "The utility of MRI in suspected MS: Report of the Therapeutics and Technology Assessment Subcommittee of the American Academy of Neurology," Neurology 61:602-611 (2003).

Grzonka, et al.; "Structural studies of cysteine proteases and their inhibitors," Acta Biochimica Polonica 48:1-20 (2001).

Li, et al.; "Molecular and cellular mechanisms of neuronal cell death in HIV dementia," Neurotox Res, 8(1-2):119-134 (2005).

Lofberg, et al.; "Quantitation of gamma-trace in human biological fluids: indications for production in the central nervous system," Scand J Clin Lab Invest, 39:619-626 (1979).

McDonald, et al. "Recommended diagnostic criteria for multiple sclerosis: guidelines from the International Panel on the diagnosis of multiple sclerosis," Ann Neurol. 50:121-127 (2001).

Melancon, et al.; "A novel method for imaging in vivo degradation of poly(L-glutamic acid), a biodegradable drug carrier." Pharm Res., 24(6):1217-1224 (2007).

Morrison, S. "In vitro antibodies: strategies for production and application," Annu. Rev. Immunol., 10:239-65 (1992).

Mosmann, "Rapid colorimetric assay for cellular growth and survival: application to proliferation and cytotoxicity assays," J Immunol Methods, 65(1-2):55-63 (1983).

Ousman, et al. "Protective and therapeutic role for alphaB-crystallin in autoimmune demyelination," Nature, 448(7152):474-479 (2007).

Petricoin, et al.; "SELDI-TOF-based serum proteomic pattern diagnostics for early detection of cancer," Curr Opin Biotechnol. 15:24-30 (2004).

Poulter, et al.; "Neuroimmunophilins: a novel drug therapy for the reversal of neurodegenerative disease?" Neuroscience, 128(1):1-6(2004).

Sacktor, et al.; "HIV-associated cognitive impairment before and after the advent of combination therapy," J Neurovirol. 8:136-142 (2002).

Shevchenko, et al.; "Mass spectrometric sequencing of proteins silver-stained polyacrylamide gels," Anal Chem. 68:850-858 (1996).

Xu, et al.; "Residue at Position 331 in the IgG1 and IgG4 $C_H2$ Domains Contributes to Their Differential Ability to Bind and Activate Complement," J Biol. Chem. 269(5): 3469-3474 (1994).

Yin, et al.; "Genetically encoded short peptide tag for versatile protein labeling by Sfp phosphopantetheinyl transferase," PNAS 102: 15815-20 (2005).

Zamin, et al.; "Protective effect of resveratrol against oxygen-glucose deprivation in organotypic hippocampal slice cultures: Involvement of PI3-K pathway," Neurobiol Dis, 24(1):170-182 (2006).

* cited by examiner

Figure 6
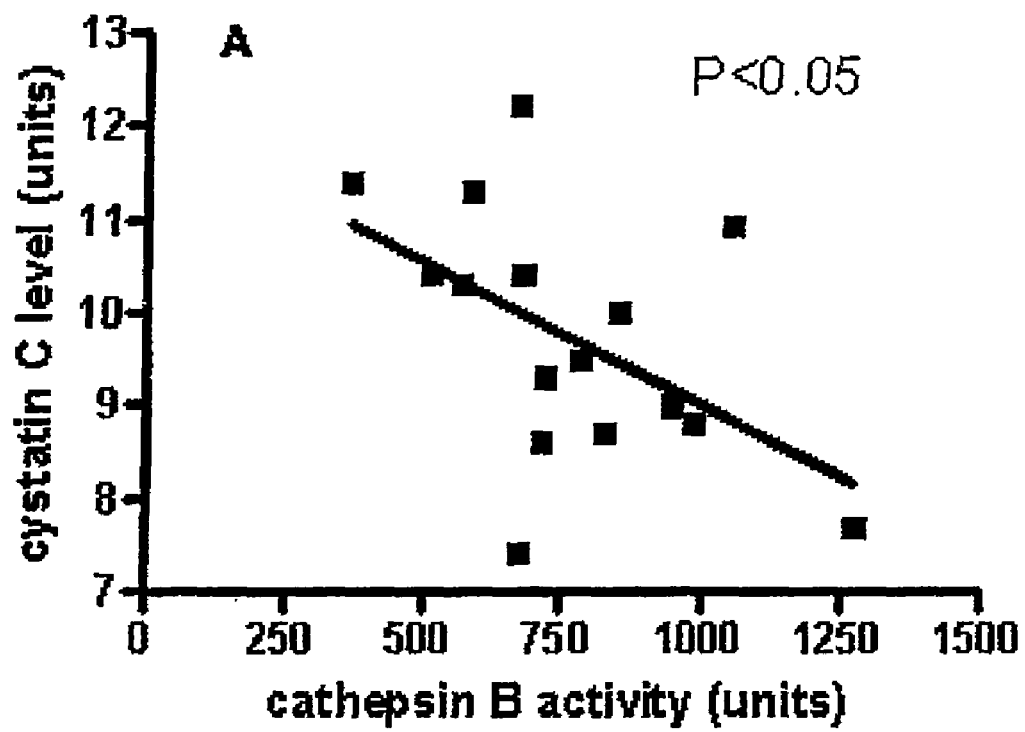
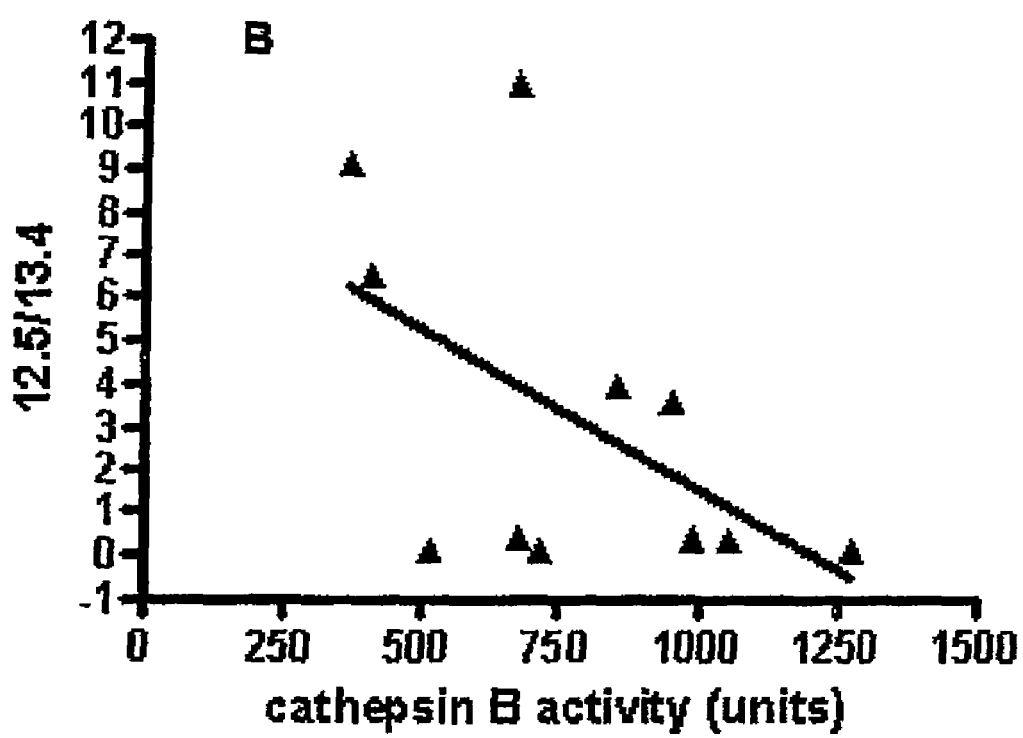

Table 1. Demographics of Patients with MS/CIS

| Sample No. | Age (yr) | Sex | Race | Diagnosis | Duration (mo) | No. of Prior Attacks | Last Attack (wk) | EDSS at LP | Steroid (last mo) | IMA at LP | CSF wbc | CSF prot | OCB | IgG Index | T2 br Lesion | T2 Cord Lesion | Enhancing Brain Lesion | Enhancing Cord Lesion | T1 Holes | MRI Criteria[a] | 12.5/13.4 Ratio |
|---|---|---|---|---|---|---|---|---|---|---|---|---|---|---|---|---|---|---|---|---|---|
| 31 | 23 | M | Asian | RR | 24 | 3 | 24 | 1.5 | No | - | 3 | 26 | 2 | 1.4 | 21 | | 2 | | 4 | + | 0.1262 |
| 42 | 30 | F | White | RR | 18 | 3 | 8 | 2.5 | No | - | 8 | 42 | 1 | 1.1 | 2 | | 1 | 0 | 0 | - | 0.0989 |
| 45 | 39 | M | White | RR | 11 | 2 | 6 | 2.5 | No | - | 16 | 33 | 5 | 1.5 | 7 | 1 | 1 | | 0 | + | 0.0879 |
| 52 | 49 | F | Black | RR | 5 | 2 | 8 | 2 | No | - | 7 | 57 | 6 | 1.2 | 7 | | 2 | | 0 | + | 0.1059 |
| 61 | 44 | F | White | RR | 11 | 2 | 10 | 3.5 | No | - | 1 | 32 | 3 | 0.8 | 22 | | 0 | | 6 | + | 0.0776 |
| 78 | 35 | F | White | RR | 92 | 3 | 14 | 1 | No | - | 6 | 27 | 3 | 1.3 | 2 | 1 | 0 | 0 | 0 | - | 0.0759 |
| 79 | 54 | F | Black | RR | 8 | 2 | 8 | 3 | No | - | 3 | 28 | 6 | 2.2 | 8 | | 2 | | 1 | + | 0.1262 |
| 109 | 24 | F | White | RR | 31 | 2 | 52 | 0 | No | - | 4 | 21 | 8 | 2.8 | 4 | | 0 | | 0 | - | 0.0989 |
| 151 | 39 | F | White | CIS[b] | 3 | 1 | 12 | 1.5 | No | - | 6 | 49 | 4 | 2 | 10 | | 1 | | 0 | + | 0.0879 |
| 152 | 32 | F | White | CIS | 2 | 1 | 8 | 2.5 | Yes | - | 18 | 62 | 6 | 1.7 | 8 | | 2 | | 0 | + | 0.1059 |
| 168 | 45 | F | White | RR | 42 | 2 | 6 | 2.5 | No | - | 1 | 36 | 3 | 1.1 | 0 | | 0 | 0 | 0 | - | 6.1187 |
| 169 | 42 | F | White | RR | 66 | 3 | 12 | 2.5 | No | - | 1 | 17 | 2 | 0.9 | 2 | 0 | 0 | 0 | 0 | - | 3.9665 |
| 171 | 45 | M | White | RR | 7 | 2 | 8 | 3 | No | - | 24 | 45 | 4 | 1.4 | 3 | 1 | 0 | 1 | 0 | + | 14.547 |
| 174 | 63 | F | Black | SP | 168 | | | 6 | No | - | 1 | 47 | 6 | 1.9 | 25 | 2 | 0 | 1 | 7 | + | 7.0584 |
| 185 | 37 | F | White | SP | 102 | | | 7 | No | + | 2 | 32 | 2 | 1.4 | 16 | 2 | 2 | 0 | 6 | + | 9.0739 |
| 191 | 33 | F | Black | RR | 48 | 3 | 4 | 2.5 | No | - | 1 | 22 | 2 | 1.9 | 2 | 1 | 0 | 0 | 0 | - | 5.7216 |
| 192 | 54 | M | White | CIS[b] | 4 | 1 | 3 | 2.0 | Yes | + | 2 | 55 | 5 | 0.8 | 1 | 2 | 1 | 1 | 0 | + | 10.146 |
| 247 | 26 | F | White | RR | 7 | 2 | 2 | 1.5 | No | - | 8 | 18 | 1 | 1.5 | 2 | 2 | 0 | | 0 | - | 4.3576 |
| 251 | 33 | F | White | CIS[b] | 3 | 1 | 4 | 3 | Yes | - | 4 | 24 | 2 | 0.7 | 11 | | 0 | | 0 | l + | 0.4099 |
| 252 | 24 | F | Black | RR | 10 | 3 | 12 | 2.5 | No | - | 9 | 33 | 7 | 3.4 | 6 | 3 | 3 | 0 | 0 | + | 0.779 |
| 256 | 53 | F | White | RR | 6 | 2 | 8 | 2 | No | - | 6 | 45 | 5 | 2.2 | 4 | | 1 | | 0 | - | 0.296 |
| 259 | 27 | F | White | RR | 5 | 2 | 4 | 2 | No | - | 2 | 34 | 0 | 0.5 | 2 | | 0 | | 0 | 0 | 0.5492 |
| 267 | 40 | M | White | RR | 40 | 2 | 7 | 2 | No | - | 42 | 58 | 2 | 3.5 | 4 | | 1 | | 0 | + | 1.9112 |
| 271 | 40 | F | Black | RR | 13 | 2 | 6 | 2 | No | - | 1 | 23 | 1 | 2.1 | 14 | | 0 | | 1 | + | 3.5913 |
| 303 | 37 | F | Black | CIS[b] | 2 | 1 | 8 | 2.5 | No | - | 20 | 44 | 2 | 1.1 | 14 | 2 | 3 | 2 | 0 | + | 12.276 |
| 329 | 44 | M | White | RR | 24 | 2 | 8 | 1.5 | No | - | 4 | 33 | 2 | 1.5 | 4 | | 0 | | 0 | - | 2.3348 |
| 330 | 54 | M | White | RR | 58 | 4 | 8 | 2.5 | No | - | 2 | 37 | 7 | 1.4 | 17 | | 6 | | 3 | + | 6.3686 |
| 331 | 37 | F | White | CIS | 2 | 1 | 5 | 2 | Yes | - | 26 | 34 | 3 | 1.3 | 4 | | 1 | | 0 | - | 4.9795 |
| 332 | 31 | F | White | RR | 30 | 2 | 8 | 2.5 | Yes | - | 5 | 48 | 3 | 1.4 | 4 | | 1 | | 0 | + | 2.5962 |

[a] Meets criteria for MRI abnormality consistent with diagnosis of MS.
[b] CIS patients that have since converted to clinically definite MS.

MS = multiple sclerosis; CIS = clinically isolated syndrome; EDSS = Expanded Disability Status Score; MRI = magnetic resonance imaging; IMA = immunomodulatory therapy; RR = relapsing-remitting; SP = secondary progressive MS; OCB = oligoclonal band; CSF = cerebrospinal fluid; LP = lumbar puncture.

Figure 10

Table 2. Peak Intensities Significantly Altered in Patients with MS

| Peak | OND (mean intensity +SD) | MS (mean intensity +SD) | p |
|---|---|---|---|
| Protein peaks elevated in MS | | | |
| 12.5kDa | 0.04 + 0.03 | 0.46 + 0.42 | <0.0001 |
| 3.9kDa | 0.15 + 0.11 | 0.29 + 0.22 | 0.007 |
| Protein peaks diminished in MS | | | |
| 13.4kDa | 0.73 + 0.26 | 0.41 + 0.32 | 0.0005 |
| 13.6kDa | 0.20 + 0.06 | 0.13 + 0.08 | 0.0005 |

MS = multiple sclerosis; OND = other neurological disorder; SD = standard deviation.

Figure 11

Table 3. Peptides Recovered from Tryptic Digestion of the 12.5kDa Protein Band (amino acid residue, observed molecular weight, and sequence are shown)

| Residues | Observed MW | Sequence |
|---|---|---|
| 1-8 | 825.00 | SSPGKPPR |
| 9-25 | 1800.91 | LVGGPMDASVEEEGVRR |
| 9-25 | 1816.94 | LVGGPMDASVEEEGVRR + oxidation (M) |
| 25-36 | 1382.76 | RALDFAVGEYNK |
| 36-36 | 1226.68 | ALDFAVGEYNK [ion score 60] |
| 46-45 | 2303.93 | ALDFAVGEYNKASNDMYHSR + oxidation (M) |
| 37-45 | 1080.54 | ASNDMYHSR |
| 37-45 | 1096.55 | ASNDMYHSR + oxidation (M) |
| 46-53 | 912.62 | ALQVVRAR |
| 76-92 | 2060.92 | TQPNLDNCPFHDQPHLK + (carbamidomethyl) [ion score 41] |

Figure 12

Figure 16  Peaks differentially expressed between Controls and MS samples using Biomarker Wizard Table 4A. Peaks elevated in MS

| | M/Z | p-value | Control mean intensity+SD | MS mean intensity+SD |
|---|---|---|---|---|
| A | 12553.9 | 0.000000006 | 0.04+0.03 | 0.46+0.42 |
| B | 6352.3 | 0.000041613 | 0.14+0.07 | 0.22+0.09 |
| C | 12796.3 | 0.000052247 | 0.02+0.02 | 0.07+0.06 |
| D | 6373.5 | 0.0001140741 | 0.19+0.10 | 0.30+0.14 |
| E | 6273.7 | 0.0001186821 | 0.07+0.07 | 0.28+0.25 |
| F | 3933.5 | 0.0007789649 | 0.15+0.11 | 0.29+0.22 |
| G | 23014.2 | 0.003460099 | 0.15+0.04 | 0.17+0.03 |
| H | 10328.9 | 0.003766280 | 0.06+0.04 | 0.09+0.05 |
| I | 6248.0 | 0.008267263 | 0.33+0.17 | 0.43+0.17 |

Figure 17

Table 4B. Peaks Diminished in MS:

| | M/Z | p-value | Control mean intensity+SD | MS mean intensity+SD |
|---|---|---|---|---|
| J | 13357.4 | 0.0000056 | 0.73+0.26 | 0.41+0.32 |
| K | 6877.0 | 0.0000072 | 1.23+1.00 | 0.63+0.55 |
| L | 13768.9 | 0.0000654 | 1.54+0.99 | 0.97+0.57 |
| M | 6677.2 | 0.0000679 | 0.52+0.23 | 0.29+0.23 |
| N | 13567.6 | 0.0000787 | 0.20+0.06 | 0.13+0.08 |
| O | 6621.9 | 0.0019336 | 0.16+0.10 | 0.10+0.07 |
| P | 6939.5 | 0.0027511 | 0.77+0.36 | 0.56+0.22 |
| Q | 4684.5 | 0.0053979 | 0.16+0.09 | 0.12+0.05 |
| R | 3638.7 | 0.0055466 | 0.22+0.06 | 0.18+0.10 |
| S | 13882.6 | 0.0058552 | 1.00+0.35 | 0.82+0.26 |

SEQUENCE LISTING

<160> NUMBER OF SEQ ID NOS: 11

<210> SEQ ID NO 1
<211> LENGTH: 417
<212> TYPE: DNA
<213> ORGANISM: Homo sapiens

<400> SEQUENCE: 1

```
atggccgggc ccctgcgcgc cccgctgctc ctgctggcca tcctggccgt ggccctggcc      60
gtgagccccg cggccggctc cagtcccggc aagccgccgc gcctggtggg aggccccatg     120
gacgccagcg tggaggagga gggtgtgcgg cgtgcactgg actttgccgt cggcgagtac     180
aacaaagcca gcaacgacat gtaccacagc cgcgcgctgc aggtggtgcg cgcccgcaag     240
cagatcgtag ctggggtgaa ctacttcttg gacgtggagc tgggccgaac cacgtgtacc     300
aagacccagc ccaacttgga caactgcccc ttccatgacc agccacatct gaaaaggaaa     360
gcattctgct ctttccagat ctacgctgtg ccttggcagg gcacaatgac cttgtcg       417
```

<210> SEQ ID NO 2
<211> LENGTH: 138
<212> TYPE: PRT
<213> ORGANISM: Homo sapiens

<400> SEQUENCE: 2

Met Ala Gly Pro Leu Arg Ala Pro Leu Leu Leu Ala Ile Leu Ala
1               5                   10                  15

Val Ala Leu Ala Val Ser Pro Ala Ala Gly Ser Ser Pro Gly Lys Pro
            20                  25                  30

Pro Arg Leu Val Gly Gly Pro Met Asp Ala Ser Val Glu Glu Glu Gly
        35                  40                  45

Val Arg Arg Ala Leu Asp Phe Ala Val Gly Glu Tyr Asn Lys Ala Ser
    50                  55                  60

Asn Asp Met Tyr His Ser Arg Ala Leu Gln Val Arg Ala Arg Lys
65                  70                  75                  80

Gln Ile Val Ala Gly Val Asn Tyr Phe Leu Asp Val Glu Leu Gly Arg
                85                  90                  95

Thr Thr Cys Thr Lys Thr Gln Pro Asn Leu Asp Asn Cys Pro Phe His
            100                 105                 110

Asp Gln Pro His Leu Lys Arg Lys Ala Phe Cys Ser Phe Gln Ile Tyr
                115                 120                 125

Ala Val Pro Trp Gln Gly Thr Met Thr Leu
        130                 135

<210> SEQ ID NO 3
<211> LENGTH: 441
<212> TYPE: DNA
<213> ORGANISM: Homo sapiens

<400> SEQUENCE: 3

```
atggccgggc ccctgcgcgc cccgctgctc ctgctggcca tcctggccgt ggccctggcc    60
gtgagccccg cggccggctc cagtcccggc aagccgccgc gcctggtggg aggccccatg   120
gacgccagcg tggaggagga gggtgtgcgc cgtgcactgg actttgccgt cggcgagtac   180
aacaaagcca gcaacgacat gtaccacagc cgcgcgctgc aggtggtgcg cgcccgcaag   240
cagatcgtag ctggggtgaa ctacttcttg gacgtggagc tgggccgaac cacgtgtacc   300
aagacccagc ccaacttgga caactgcccc ttccatgacc agccacatct gaaaaggaaa   360
gcattctgct ctttccagat ctacgctgtg ccttggcagg gcacaatgac cttgtcgaaa   420
tccacctgtc aggacgccta g                                             441
```

<210> SEQ ID NO 4
<211> LENGTH: 146
<212> TYPE: PRT
<213> ORGANISM: Homo sapiens

<400> SEQUENCE: 4

Met Ala Gly Pro Leu Arg Ala Pro Leu Leu Leu Ala Ile Leu Ala
1               5                   10                  15

Val Ala Leu Ala Val Ser Pro Ala Ala Gly Ser Ser Pro Gly Lys Pro
            20                  25                  30

Pro Arg Leu Val Gly Gly Pro Met Asp Ala Ser Val Glu Glu Glu Gly
        35                  40                  45

Val Arg Arg Ala Leu Asp Phe Ala Val Gly Glu Tyr Asn Lys Ala Ser
    50                  55                  60

Asn Asp Met Tyr His Ser Arg Ala Leu Gln Val Val Arg Ala Arg Lys
65                  70                  75                  80

Gln Ile Val Ala Gly Val Asn Tyr Phe Leu Asp Val Glu Leu Gly Arg
                85                  90                  95

```
Thr Thr Cys Thr Lys Thr Gln Pro Asn Leu Asp Asn Cys Pro Phe His
            100                 105                 110

Asp Gln Pro His Leu Lys Arg Lys Ala Phe Cys Ser Phe Gln Ile Tyr
        115                 120                 125

Ala Val Pro Trp Gln Gly Thr Met Thr Leu Ser Lys Ser Thr Cys Gln
130                 135                 140

Asp Ala
145

<210> SEQ ID NO 5
<211> LENGTH: 136
<212> TYPE: PRT
<213> ORGANISM: Homo sapiens

<400> SEQUENCE: 5

Leu Leu Ala Ile Leu Ala Val Ala Leu Ala Val Ser Pro Ala Ala Gly
1               5                   10                  15

Ser Ser Pro Gly Lys Pro Pro Arg Leu Val Gly Gly Pro Met Asp Ala
            20                  25                  30

Ser Val Glu Glu Glu Gly Val Arg Arg Ala Leu Asp Phe Ala Val Gly
        35                  40                  45

Glu Tyr Asn Lys Ala Ser Asn Asp Met Tyr His Ser Arg Ala Leu Gln
    50                  55                  60

Val Val Arg Ala Arg Lys Gln Ile Val Ala Gly Val Asn Tyr Phe Leu
65                  70                  75                  80

Asp Val Glu Leu Gly Arg Thr Thr Cys Thr Lys Thr Gln Pro Asn Leu
                85                  90                  95

Asp Asn Cys Pro Phe His Asp Gln Pro His Leu Lys Arg Lys Ala Phe
            100                 105                 110

Cys Ser Phe Gln Ile Tyr Ala Val Pro Trp Gln Gly Thr Met Thr Leu
        115                 120                 125

Ser Lys Ser Thr Cys Gln Asp Ala
    130                 135

<210> SEQ ID NO 6
<211> LENGTH: 48
<212> TYPE: DNA
<213> ORGANISM: Artificial Sequence
<220> FEATURE:
<223> OTHER INFORMATION: synthetic linker oligonucleotide

<400> SEQUENCE: 6
tctagaggtg gtctagtgcc gcgcggcagc ggttcccccg ggttgcag            48

<210> SEQ ID NO 7
<211> LENGTH: 128
<212> TYPE: PRT
<213> ORGANISM: Homo sapiens

<400> SEQUENCE: 7

Leu Leu Ala Ile Leu Ala Val Ala Leu Ala Val Ser Pro Ala Ala Gly
1               5                   10                  15

Ser Ser Pro Gly Lys Pro Pro Arg Leu Val Gly Gly Pro Met Asp Ala
            20                  25                  30

Ser Val Glu Glu Glu Gly Val Arg Arg Ala Leu Asp Phe Ala Val Gly
        35                  40                  45

Glu Tyr Asn Lys Ala Ser Asn Asp Met Tyr His Ser Arg Ala Leu Gln
    50                  55                  60

Val Val Arg Ala Arg Lys Gln Ile Val Ala Gly Val Asn Tyr Phe Leu
```

```
                65                  70                  75                  80
Asp Val Glu Leu Gly Arg Thr Thr Cys Thr Lys Thr Gln Pro Asn Leu
                        85                  90                  95
Asp Asn Cys Pro Phe His Asp Gln Pro His Leu Lys Arg Lys Ala Phe
                100                 105                 110
Cys Ser Phe Gln Ile Tyr Ala Val Pro Trp Gln Gly Thr Met Thr Leu
            115                 120                 125

<210> SEQ ID NO 8
<211> LENGTH: 16
<212> TYPE: PRT
<213> ORGANISM: Artificial Sequence
<220> FEATURE:
<223> OTHER INFORMATION: synthetic linker peptide

<400> SEQUENCE: 8

Ser Arg Gly Gly Leu Val Pro Arg Gly Ser Gly Ser Pro Gly Leu Gln
1               5                   10                  15

<210> SEQ ID NO 9
<211> LENGTH: 6
<212> TYPE: PRT
<213> ORGANISM: Artificial Sequence
<220> FEATURE:
<223> OTHER INFORMATION: synthetic polyhistidine tag

<400> SEQUENCE: 9

His His His His His His
1               5

<210> SEQ ID NO 10
<211> LENGTH: 11
<212> TYPE: PRT
<213> ORGANISM: Artificial Sequence
<220> FEATURE:
<223> OTHER INFORMATION: synthetic peptide

<400> SEQUENCE: 10

Asp Ser Leu Glu Phe Ile Ala Ser Lys Leu Ala
1               5                   10

<210> SEQ ID NO 11
<211> LENGTH: 4
<212> TYPE: PRT
<213> ORGANISM: Artificial Sequence
<220> FEATURE:
<223> OTHER INFORMATION: Illustrative ER retention signal peptide

<400> SEQUENCE: 11

Lys Asp Glu Leu
1
```

METHODS FOR DIAGNOSIS AND OPTIMIZING TREATMENT OF MULTIPLE SCLEROSIS

CROSS-REFERENCE

This application is a continuation-in-part application of PCT International Application PCT/US07/64532 filed Mar. 21, 2007, which claims the benefit of U.S. Provisional Patent Application Ser. No. 60/784,425, filed on Mar. 21, 2006, the contents of all of which are incorporated herein by reference in their entirety.

STATEMENT AS TO FEDERALLY SPONSORED RESEARCH

The methods and compositions described herein were generated with U.S. government support under Grant Numbers R01NS039253, R01NS043990, and R01GM64402 from the National Institutes of Health. Accordingly, the U.S. Government has certain rights pertaining to the use of the compositions and methods described herein.

BACKGROUND OF THE INVENTION

Multiple sclerosis (MS) is an autoimmune neurodegenerative disease, which is marked by inflammation within the central nervous system with lymphocyte attack against myelin produced by oligodendrocytes, plaque formation and demyelination with destruction of the myelin sheath of axons in the brain and spinal cord, leading to significant neurological disability over time. The disease frequently occurs in young adults between 20-40 years of age, is more prevalent in females than males (2:1), and has a characteristic geographical distribution—estimated prevalence in the USA is 120/100,000 individuals (250,000 to 350,000 cases).

The diagnosis of MS is still defined primarily by clinical terms and relies on a combination of history, neurological examination and ancillary laboratory and neuro-imaging studies. Typically, at onset an otherwise healthy person presents with the acute or sub acute onset of neurological symptomatology (attack) manifested by unilateral loss of vision, vertigo, ataxia, dyscoordination, gait difficulties, sensory impairment characterized by paresthesia, dysesthesia, sensory loss, urinary disturbances, diplopia, dysarthria or various degrees of motor weakness. The symptoms are usually painless, persist for several days to a few weeks, and then partially or completely resolve. For the period following the first attack, the patient is defined to suffer from "probable MS." Probable MS patients may remain undiagnosed for "definite MS" for years. After this variable period of remission, generally a second attack will occur, after which the diagnosis of "clinically definite MS" (CDMS) is made.

Laboratory tests for MS include: 1) cerebrospinal fluid (CSF) evaluation of IgG synthesis, oligoclonal bands; 2) MRI of the brain and spinal cord and; 3) exclusion of other autoimmune diseases by blood tests (e.g.; serum B12 level; HTLV 1 or HIV 1 titers; sedimentation rate or C-reactive protein; RA latex (Rheumatoid arthritis); ANA, anti-DNA antibodies (systemic lupus erythematosus). More recently, diagnostic criteria for CDMS have incorporated radiological assays, however, accurate diagnosis and prognosis in the "probable" stage, and early relapsing-remitting stages remains problematic. For example, it has been shown that positive MRI findings in the first demyelinating attack only provide a 50% successful prediction of development of clinically definite MS within 2-3 years. Likewise, detection of oligoclonal IgM bands in patients with early symptoms were only partially predictive of development of clinically definite MS.

SUMMARY OF THE INVENTION

Described herein are methods and compositions for diagnosis or prognosis of multiple sclerosis. Also provided herein are methods for treating multiple sclerosis in subjects diagnosed by the methods described herein.

Accordingly, in one aspect provided herein is a method for method for determining the diagnosis or prognosis of multiple sclerosis in a subject, that comprises analyzing in a biological sample from the subject the level of a cystatin C protein fragment lacking about 8 amino acids at its C-terminus, and providing to a medical caregiver for the subject analysis data for the level of the fragment or a value for the level of the fragment. As used herein, a "medical caregiver," refers to a professional that interacts directly with a subject and is responsible for determining a diagnosis, prognosis, or treatment for the subject. Examples of such individuals include, but are not limited to, physicians, nurses, and pharmacists.

In some embodiments, the above-described method further includes providing an indication to the medical caregiver that a ratio of C protein fragment lacking about 8 amino acids at its C-terminus cystatin C protein fragment to full length cystatin C protein greater than a control ratio reference value, as described herein, indicates that a subject has multiple sclerosis or is at high risk for developing multiple sclerosis. In some embodiments, the indication is provided to the medical caregiver prior to the above-described analysis. In some embodiments, the cystatin C fragment lacking about 8 amino acids at its C-terminus has an amino acids sequence that is at least 95% identical to SEQ ID NO:2. In some embodiments, the above-mentioned methods further comprises providing a comparison of the value for the level of the cystatin C protein fragment to a control level reference value, as described herein. In some embodiments, the above-described method further comprises determining the level of full length cystatin C protein in the biological sample and providing to the medical caregiver (i) analysis data for the level of the full length cystatin C protein, (ii) a value for the level of cystatin C protein, or (iii) a value for the ratio of the level of the fragment to the level of the full length cystatin C protein. In some embodiments, the biological sample to be analyzed is a cerebrospinal fluid or blood sample. In some embodiments, the analyzing comprises contacting the biological sample with an antibody that specifically binds to the cystatin C protein fragment and does not bind to the full length cystatin C protein. In some embodiments, the analyzing comprises performing mass spectroscopy on the biological sample and indicating the peak corresponding to the cystatin c protein fragment. In some embodiments, the method further comprises performing a cathepsin B activity assay on at least a fraction of the biological sample.

In a related aspect, provided herein is a method for diagnosis or prognosis of multiple sclerosis in a subject, that comprises (i) determining in a biological sample from the subject the level of full length cystatin C protein and the level of a cystatin C protein fragment lacking about 8 amino acids at its C-terminus; (ii) determining the ratio of the fragment to full length cystatin C protein in the biological sample; and (iii) providing the value of the ratio to a medical caregiver for the subject.

In a further related aspect provided herein is a method for diagnosis or prognosis of multiple sclerosis in a subject, comprising determining in a cerebrospinal fluid sample from the subject the level of cystatin C protein fragment lacking about 8 amino acids at its C-terminus, providing the value of the level to a medical caregiver for the subject, and providing an indication to the medical caregiver to determine the ratio of the value for the level of the fragment to the value for the level of full length cystatin C protein.

In yet another aspect provided herein is a method for prognosis or diagnosis of multiple sclerosis in a subject, that comprises analyzing in a biological sample from the subject the level of one or more biomarkers identified in Table 2 or Table 4, and providing to a medical caregiver for the subject analysis data for the level of the one or more biomarkers identified in Table 2 or Table 4, or values for the level of the one or more biomarkers identified in Table 2 or Table 4. In some embodiments, the just-described method further comprises providing a comparison of the value of the ratio to a control ratio reference value. In some embodiments, the method further comprises providing an indication to the medical caregiver that a ratio of a cystatin C protein fragment lacking about 8 amino acids at its C-terminus cystatin C protein fragment to full length cystatin C protein greater than a control ratio reference value indicates that a subject has multiple sclerosis or is at high risk for developing multiple sclerosis. In some embodiments, the method further comprises determining the level of (alpha)B crystallin or an (alpha)B crystallin antibody in a biological sample from the subject. In some embodiments, the biological sample is a cerebrospinal fluid sample or a blood sample.

In a further aspect, provided herein is a method for optimizing multiple sclerosis treatment of a subject in need thereof, that comprises providing a multiple sclerosis treatment to the subject, comparing the ratio of a cystatin C protein fragment lacking about 8 amino acids at its C terminus to full length cystatin C protein in a first biological sample obtained from the subject prior to the treatment; to the ratio of the cystatin C protein fragment lacking about 8 amino acids at its C terminus to the full length cystatin C protein in a second biological sample obtained from the subject after the beginning of the treatment, and altering the treatment if the ratio in the second biological sample is greater than the ratio in the first biological sample; or maintaining the treatment unaltered if the ratio in the second biological sample is equal to or less than the ratio in the first biological sample. In some embodiments, the just-described method comprises administering a composition comprising a therapeutically effective amount of one or more modified terpenoids having neuroprotective activity, as described herein, or one or more anti-fungal agents having neuroprotective activity, as described herein. In some embodiments, the biological sample is a cerebrospinal fluid sample or a blood sample.

In another aspect provided herein is a method for treating or reducing the risk of developing multiple sclerosis in a subject in need thereof, that comprises comparing the ratio of a cystatin C protein fragment lacking about 8 amino acids at its C terminus to full length cystatin C protein in a biological sample from the subject to a control ratio reference value and providing or prescribing a course of treatment for the subject if the ratio is greater than the control ratio reference value. In some embodiments, the above-mentioned method comprises administering to the subject a composition comprising a therapeutically effective amount of one or more modified terpenoids having neuroprotective activity, as described herein, or one or more anti-fungal agents having neuroprotective activity, as described herein. In some embodiments, the one or more modified terpenoids comprise the modified terpenoid having the structure of Formula I:

Formula I

[chemical structure with $Y_1$, $Y_2$, $H_3C$, $R_1$, $R_2$, O]

In yet another aspect provided herein is a method for treating or reducing the risk of developing MS or a related condition in a subject, comprising administering to a subject in need thereof a therapeutically effective amount of an agent that decreases cathepsin activity. In some embodiments, the just-mentioned method further comprises determining a level of cathepsin activity in a subject before and after the administration. In some embodiments, the level of cathepsin activity comprises using a near-infrared fluorescence dye-Cathepsin B substrate conjugate as a probe of Cathepsin B activity. In some embodiments, the method further comprises administering a composition comprising a therapeutically effective amount of one or more modified terpenoids having neuroprotective activity, as described herein or one or more anti-fungal agents having neuroprotective activity, as described herein.

In yet another aspect provided herein is an isolated antibody that binds specifically to a cystatin C protein fragment lacking about 8 amino acids at its C-terminus and does not bind significantly to a full-length cystatin C protein.

In a further aspect provided herein is an isolated antibody that binds specifically to an epitope in the last 8 amino acids of the cystatin C protein C-terminus, and does not bind significantly to the full-length C-protein.

In another aspect provided herein is an isolated antibody that binds specifically to an epitope in the last 8 amino acids of the cystatin C protein C-terminus, and does not bind significantly to the full-length C-protein.

In a related aspect provided herein is a kit comprising either of the above mentioned isolated antibodies, and a reagent for detecting binding of the isolated antibody. In some embodiments, the kit further comprises an antibody that specifically binds to full length cystatin C, but does not bind significantly to a cystatin C protein fragment lacking about 8 amino acids at its C-terminus.

In a related aspect provided herein is a kit comprising (i) an antibody that binds specifically to a cystatin C protein fragment the amino acid sequence of which comprises SEQ ID NO:2, but does not bind significantly to a full length cystatin C protein, and (ii) an antibody that binds specifically to full length cystatin C protein. In some embodiments, the kit further comprises an isolated polypeptide comprising an amino acid sequence that is at least 95% identical to SEQ ID NO: 2, wherein the polypeptide does not comprise the last 8 C-terminal amino acids of cystatin C.

In yet another aspect provided herein is an isolated polypeptide comprising an amino acid sequence that is at least 95% identical to SEQ ID NO: 2, wherein the protein does not comprise the last 8 C-terminal amino acids of cystatin C.

In a further aspect provided herein is an isolated polynucleotide comprising a nucleotide sequence that encodes a polypeptide comprising an amino acid sequence at least 95% identical to SEQ ID NO: 2, wherein the nucleic acid does not encode a polypeptide comprising the last C-terminal 8 amino acids of SEQ ID NO:4. In some embodiments, the just-mentioned polynucleotide is part of a vector. In some embodiments, the vector includes the polynucleotide operably linked to a promoter. Also provided herein are a cell (e.g., a prokaryotic or eukaryotic cell) comprising the just-mentioned vectors. In some embodiments the nucleotide sequence comprises a nucleotide sequence that is identical to SEQ ID NO:1. In some embodiments, the polynucleotide comprises a nucleotide sequence consisting essentially of SEQ ID NO: 1.

In a further aspect provided herein is the use of one or more modified terpenoids of formula I for the manufacture of a medicament for treating or reducing the risk of developing multiple sclerosis in a subject having a ratio of a cystatin C protein fragment lacking about 8 amino acids at its C terminus to full length cystatin C protein that is greater than a control ratio reference value. In some embodiments, the one or more modified terpenoids have the structure of formula I.

In yet another aspect provided herein is the use of one or more neuroprotective antifungal compounds for the manufacture of a medicament for treating or reducing the risk of developing multiple sclerosis in a subject having a ratio of a cystatin C protein fragment lacking about 8 amino acids at its C terminus to full length cystatin C protein that is greater than a control ratio reference value.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the methods and compositions described herein are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 6 shows a correlation of cystatin C levels and cathepsin B activity in the CSF of MS/CIS patients. (A) Higher cystatin C levels were associated with lower cathepsin B activity suggesting that cystatin C in the CSF of MS/CIS patients had not lost its cysteine protease inhibitory activity. (B) In some patients 12.5/13.4 peak ratios were associated with decreased cathepsin B activity.

FIG. 10 shows Table 1, which lists demographics of patients with MS/CIS.

FIG. 11 shows Table 2, which lists peak intensities significantly altered in patients with MS FIG. 12 shows Table 3, which lists peptides recovered from tryptic digestion of the 12.5 kDa protein band Amino acid residues, observed molecular weight, and sequence are shown

FIG. 16 shows Table 4A, which lists values of mass spectrometery peaks A-I (determined using Biomarker Wizard) of peptides having higher concentrations in MS samples than in control samples. The list includes the values for two cystatin C peaks.

FIG. 17 shows Table 4B, which lists values of mass spectrometery peaks J-S (determined using Biomarker Wizard) of peptides having lower concentrations in MS samples than in control samples. Each of these peaks was identified using the same weak cation CM10 chip as was used for the cystatin C peaks, hence these peaks have binding properties that are distinct in their identification.

DETAILED DESCRIPTION OF THE INVENTION

Figure 1:
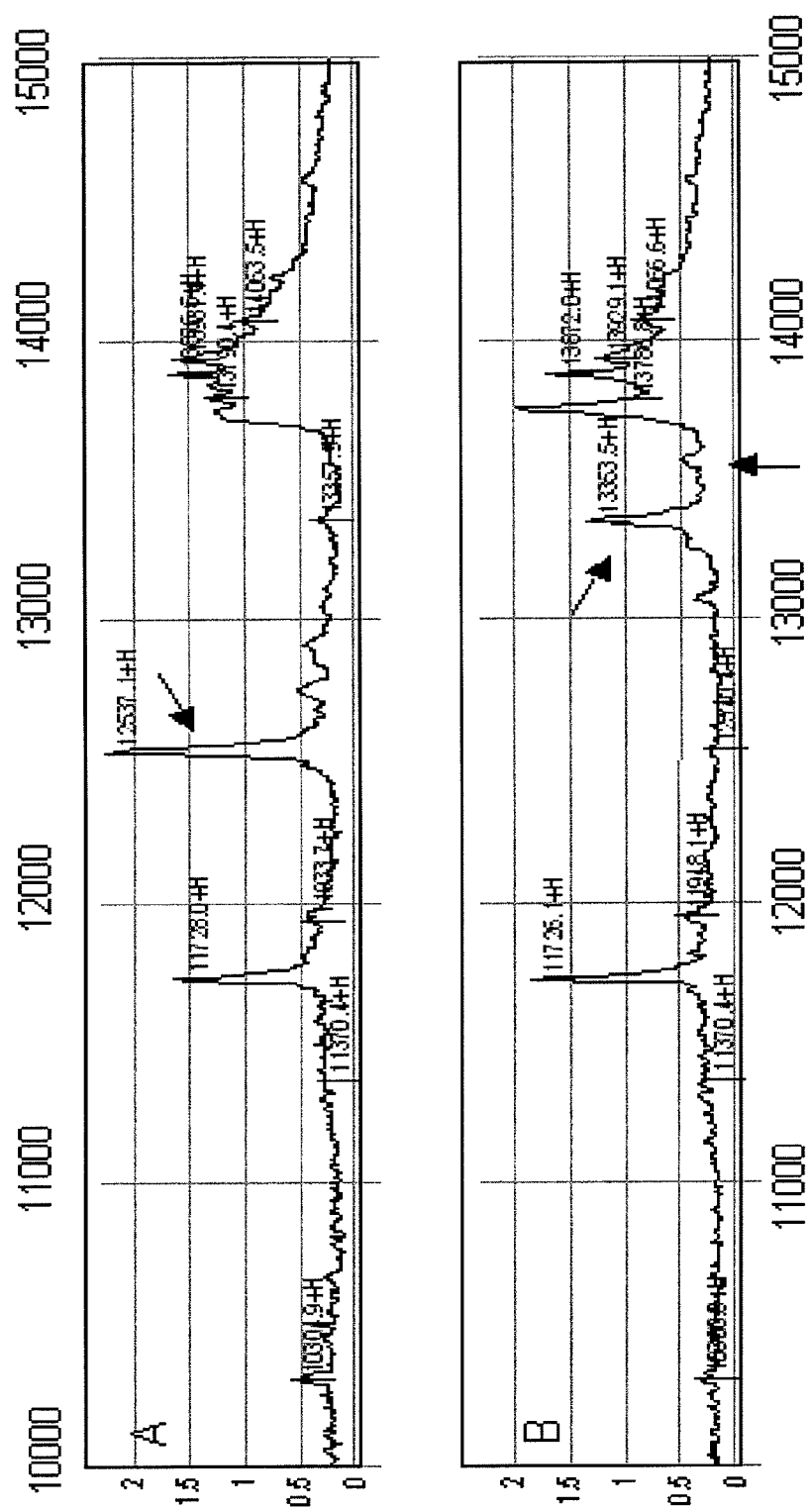
FIG. 1 shows a representative CSF spectra generated by SELDI analysis. (A) Patient with multiple sclerosis showing a prominent peak at 12.5 kD (arrow). The 13.4 kD peak is blunted. (B) The 12.5 kD peak is absent from the control patient. However the 13.4 kD peak is prominent (slanted arrow). Another small peak at 13.6 kD is also noted (vertical arrow) which is absent from the MS spectra.

The present inventors have discovered biological biomarkers whose dysregulation is indicative of multiple sclerosis (MS), i.e., MS-associated biomarkers. Methods and compositions for the diagnosis and treatment of MS or a condition relating thereto are provided herein.
Diagnostic and Prognostic Methods for Multiple Sclerosis Provided herein are methods for determining whether a subject has or is likely to develop MS or a condition relating thereto. As used herein, "MS" refers to all types and stages of MS, including, but not limited to: benign MS, relapsing remitting MS, secondary chronic progressive MS, and primary progressive MS, Progressive Relapsing Multiple Sclerosis, Chronic Progressive MS, Transitional/Progressive MS, malignant MS, also known as Marburg's Variant, and acute multiple sclerosis. Early stages of MS include an acute or sub acute onset of neurological symptomatology (attack); first attack, probable stage, second attack, early relapsing-remitting stages, and clinically isolated syndromes (CIS). "Conditions relating to MS" include, e.g., Devic's Disease, also known as Neuromyelitis Optica; and Balo's concentric sclerosis. The methods described herein may also predict the presence or likelihood of development of the early stages of MS and conditions relating to MS. For example, the methods described herein may determine: the likelihood of a symptomless subject developing MS, an early stage of MS, or a condition relating thereto; the likelihood of a subject having symptoms, e.g., symptoms that resemble those present in early stage MS, to have or to develop MS or an early stage thereof or a condition relating thereto; the likelihood of a subject having early stage MS symptoms to develop MS; or the likelihood of a subject having early stage MS symptoms to develop a particular type of MS. The methods described herein may also be used to determine the prognosis of a subject having MS, an early stage thereof or a condition relating thereto. For example, the methods may allow the prognosis of a subject that is being treated, e.g., with a modified terpenoid as described herein. The methods may also be used for determining the severity of the disease.

The method may be used to determine whether a subject is more likely than not to have MS, an early stage thereof, or a condition relating thereto, or is more likely to have MS, an early stage thereof, or a condition relating thereto than to have another disease, based on the difference between the measured and standard level or reference range of the biomarker. Thus, for example, a patient with a putative diagnosis of MS or a condition relating thereto may be diagnosed as being "more likely" or "less likely" to have MS in light of the information provided by a method described herein. If a plurality of biomarkers are measured, at least one and up to all of the measured biomarkers must differ, in the appropriate direction, for the subject to be diagnosed as having (or being more likely to have) MS or a condition relating thereto. In some embodiments, such difference is statistically significant.

The methods described herein are not limited to making an initial diagnosis of MS or a condition relating thereto, but are also applicable to confirming a provisional diagnosis of MS or a condition relating thereto, or for "ruling out" such a diagnosis.

The level of a biomarker, as described herein, is determined in a biological sample from a patient, and compared with a biomarker control level reference value or biomarker control level reference value range, where a biomarker level value greater than the biomarker control level reference value is indicative of the condition. In some embodiments, diagnosis is based on a ratio of two or more biomarkers, where the ratio of the level of a first biomarker to the level of a second biomarker is compared with a biomarker control ratio reference value or control ratio reference value range, and biomarker ratio values greater than the value of the control ratio reference value are indicative of the condition (e.g., MS). Typically, a biomarker control level reference value or biomarker control ratio reference value correspond to a numerical value that is the mean, median, or mode (or any other statistical measurement of central tendency) of the biomarker level or ratio of biomarker levels from a set of control subjects, such as one or more subject(s) that do not have MS or a condition relating thereto. A biomarker control level reference value or biomarker control ratio reference value can be based on biomarker levels from one or more subjects, e.g., 1-5; 5-10; 10-50; or more subjects. In some embodiments, "control subjects," are subjects suffering from neurological disorders other than MS or a related disorder. In other embodiments, "control subjects" are subjects that are not suffering from a health condition, disease, or disorder. Determination of the biomarker control level reference value or control ratio reference value need not be made contemporaneously with a particular patient's biomarker level, or by an individual with any knowledge or direct contact with the particular patient, e.g., the biomarker control level reference value or value range may be established based on historical measurement in a control population.

In some embodiments, a biomarker control level reference value or control ratio reference value is provided directly to a medical caregiver of a patient being tested for MS (e.g., a physician, a nurse, or a pharmacist participating directly in the medical care of the patient) along with biomarker level data (e.g., unprocessed assay data), biomarker level values, biomarker level ratios for a biological sample from the individual patient. In some embodiments, the biomarker control level reference or control ratio reference values and the biomarker level data from an individual patient sample are provided along with a comparison (e.g., a statistical comparison) of the biological sample biomarker data with the control reference values. In some embodiments, the comparison further includes an interpretation of the comparison (e.g., a likelihood that the subject is suffering from MS based on the comparison).

In some embodiments, a biomarker control level reference value or control ratio reference value is provided indirectly, e.g., by providing such values without reference or comparison to any individual patient biomarker values. For example, a biomarker control level reference value or biomarker control ratio reference value can be made available to the medical community (or the general public), e.g., in a textbook chapter, journal article, pamphlet, brochure, leaflet, booklet, magazine article, or newspaper article. The values can be provided in a hardcopy medium, digital medium (website/website link, audio recording, video recording), analog medium (e.g., film or tape recording), or as a live oral presentation. In some embodiments, the biomarker control level reference value or control ratio reference values are provided directly or indirectly, as just described, and in addition with an indication that a biomarker level value or biomarker ratio value greater or lesser (depending on the particular biomarker or biomarker ratio) than the control level reference value or control ratio reference values, respectively, indicates that a subject has multiple sclerosis or is at high risk for developing multiple sclerosis.

Thus, providing biomarker control level reference value or biomarker control ratio reference values allows a medical caregiver to determine an MS diagnosis for a patient based on a comparison of the biomarker level or biomarker ratio in a biological sample from the patient to the provided biomarker control level reference value or biomarker control ratio reference value.

In some embodiments, the comparison entails a statistical comparison to determine whether a statistically significant difference exists between the measured biomarker level or ratio and the biomarker control reference value or biomarker control ratio reference value. Accordingly, the patient can then be diagnosed, e.g., as having MS or a condition related thereto; as being likely to develop MS or a condition related thereto; or as not having MS or a condition related thereto.

The existence of a statistically significant difference between the measured biomarker level or biomarker ratio and control level reference value or control ratio reference value can be determined by standard statistical methods (e.g., Mann-Whitney test). See, e.g., Sokal et al, *Biometry*, $3^{rd}$ ed., pub. W.H. Freeman (1994).

Typically, a significant difference for biomarkers the levels of which are elevated in MS or a condition related thereto (e.g., those listed in Table 4A in FIG. 16), is indicated when the measured level is greater than the control level reference value or control ratio reference value plus at least one, at least two, at least 3, or at least 4 standard deviations above the reference level. For biomarkers the levels of which are diminished in MS or a condition related thereto (e.g., Table 4B), the measured level is less than the than the control level reference value or control ratio reference value minus at least one, at least two, at least 3, or at least 4 standard deviations below the reference level.

In some embodiments, a significant difference may mean a difference of at least 2-fold, 3-, 4-, 5-, 10- or more fold, with respect to the reference value In some embodiments, the methods described herein include determining, in a biological sample from a patient, the level of a biomarker set forth in Table 4A, where a significantly higher level than a control level reference value indicates that the patient is suffering from MS or at high risk of developing MS. In other embodiments, the methods described herein include determining in a biological sample from a patient the level of a biomarker set forth in Table 4B, where a significantly lower level than a control level reference value indicates that the patient is suffering from MS or at high risk of developing MS.

In some embodiments, levels of multiple biomarkers are determined and compared to control level reference values to so as to permit diagnosis of MS or a related condition.

In some embodiments, the methods described herein are used to make the diagnosis of MS or a related condition, independently from other information such as the patient's symptoms or the results of other clinical or paraclinical tests. In other embodiments, the methods described herein are used in conjunction with such other information.

Biomarkers described herein may be measured in combination with other signs, symptoms, and clinical tests of MS, such as MRI scans or MS biomarkers reported in the literature. Measurement of the biomarkers described herein along with any other biomarkers known in the art, including any not specifically listed herein, is also contemplated. In some embodiments, the methods described herein include determining the level of (alpha) B-crystallin or the level of an antibody against (alpha) B-crystallin in a biological sample from a patient, which has diagnostic value for multiple sclerosis, as described in, e.g., Ousman et al. (2007), *Nature*, 448(7152):472-479. In some embodiments, the level of (alpha) B-crystallin is determined in the same biological sample in which a level of one of the above-described biomarkers is determined. In other embodiments, the level of (alpha) B-crystallin is determined in an independent biological sample from the patient.

The description of the methods herein makes reference to measuring "a biomarker." The methods of described herein can include measuring two biomarkers, three biomarkers, or four or more biomarkers, or ratios of the same. The two biomarkers, three biomarkers, or four or more biomarkers may comprise any combination of biomarkers selected from Table 2 or Table 4.

Thus, a method, e.g., for diagnosing multiple sclerosis in a subject may comprise obtaining one or more biological samples from the subject; determining the level of a plurality of biomarkers in the one or more biological samples, wherein at least one of the plurality of biomarkers is selected from the group consisting of the biomarkers listed in Table 2 and Table 4; and comparing the level of at least one of the plurality of biomarkers to a control level reference value.

The biological sample to be tested for biomarkers may be of any tissue or fluid. In some embodiments, the sample is a cerebrospinal fluid (CSF) sample, but other biological fluids that may be used, include, but are not limited to, blood, serum, plasma, saliva, urine, and neural tissue.

In some embodiments, the level of a biomarker may be compared to the level of another biomarker or some other component in a different tissue, fluid or biological "compartment." Thus, a differential comparison may be made of a biomarker in CSF and serum. In some embodiments, the level of a first biomarker is compared with the level of a second biomarker or some other component within the same biological sample.

As indicated in Table 2 and Table 4, some of the biomarker measurement values are higher in samples from MS patients, while others are lower. A significant difference in the appropriate direction in the measured value of one or more of the biomarkers indicates that the patient has (or is more likely to have) MS or a condition relating thereto. If only one biomarker is measured, then that value must increase or decrease to indicate MS or a condition relating thereto. In some embodiments, multiple biomarkers are measured, and a diagnosis of MS, or early stage thereof, or a condition relating thereto is indicated by changes in multiple biomarkers. Measurements can be of (i) a biomarker described herein, (ii) a biomarker described herein and another factor known to be associated with MS or a condition relating thereto (e.g., MRI scan); (iii) a plurality of biomarkers comprising at least one biomarker described herein and at least one biomarker reported in the literature, or (iv) any combination of the foregoing. Furthermore, the amount of change in a biomarker level may be an indication of the relatively likelihood of the presence of the disease.

It is to be understood that any correlations between biological sample measurements of these biomarkers and MS or a condition relating thereto, as used for diagnosis of the disease or evaluating drug effect, are contemplated herein.

C-Terminal C Statin C Cleavage Product as a Predictor of MS or a Related Condition A method of diagnosing or prognosing or determining whether a subject has or is likely to develop multiple sclerosis may comprise determining the level, in a biological sample from the subject (e.g., a CSF sample), of the amount, or activity of a C-terminal cystatin C polypeptide fragment (i.e., the polypeptide corresponding to biomarker "A" in Table 4A; FIG. 16; amino acid sequence corresponding to SEQ ID NO:2) lacking about 8 amino acids at its C-terminus ( ) and, e.g., comparing it to the amount of full-length cystatin C polypeptide in the sample (i.e., the polypeptide corresponding to biomarker "J" in Table 4B; FIG. 16; amino acid sequence corresponding to SEQ ID NO:4). As described herein, a significantly higher ratio of the cystatin C cleavage product polypeptide to full length Cystatin C occurs in the CSF of subjects suffering from or at high risk of developing MS than in the CSF of subjects not suffering from or at high risk of MS (i.e., control subjects). Thus, a ratio of cystatin C cleavage product polypeptide to full length cystatin C that is higher than a corresponding control ratio reference value indicates a high likelihood that a subject has or is at high risk of developing MS or a related condition. Further, an increase in the C-terminal cystatin C polypeptide fragment relative to the amount of full-length cystatin C polypeptide in the sample in the same subject over time is predictive of individuals that are afflicted with MS or a related condition that is worsening, or at high risk of developing MS or a related condition.

In some embodiments, a subject is identified as being afflicted with or at risk of developing multiple sclerosis, an early stage thereof or a condition related thereto when the above-described ratio in a biological sample from the subject is greater than the corresponding control ratio reference value by at least about 1.5 fold to about 40 fold, e.g., at least about 1.8, 2.0, 2.5, 3.0, 4.3, 5.0, 5.3, 5.5, 6, 7, 9, 9.5, 10, 11, 12.5, 13.5, 14.0, 15.0, 16.0, 16.5, 17, 17.2, 17.5, 18, 18.3, 18.8, 19, 19.2, 19.8, 20.0, 20.3, 20.5, 20.7, 21, 21.5, 22, 23, 24, 26, 27, 28.5, 29, 30, 32, 33, 34, 36, 38, 38.5 fold greater than the control ratio reference value, or any other fold greater than the control ratio reference value from about 1.5 fold to about 40 fold. In some embodiments, the control ratio reference value is from about 0.80 to about 3.0, e.g., about 0.85, 0.90, 0.92, 0.95, 1.0, 1.2, 1.3, 1.4, 1.5, 1.6, 1.7, 1.8, 1.82, 1.9, 2.0, 2.3, 2.4, 2.5, 2.7, 3.0, or any other value from about 0.80 to about 3.0.

The level of a C-terminal cystatin C polypeptide fragment or cystatin c or full length cystatin polypeptide can be determined by any of a number of standard methods, some of which are described in further detail herein. Such methods include, but are not limited to, mass spectroscopy, immunoprecipitation, chromatographic separations, 2-D gel separations, binding assays (e.g., immunoassays, antibody arrays), capture arrays, or competitive inhibition assays.

In some embodiments, the technique (e.g., mass spectroscopy) used to determine the level of one or more biomarkers in a biological sample from a subject separate also detects and quantifies in parallel a wide range of other biomolecules (e.g., polypeptides) in the sample. Accordingly, in some embodiments, a method for diagnosing MS or a related condition includes (i) providing primary analytical data for the for the biological sample from a subject of interest to a medical caregiver for the subject, and (ii) directly or indirectly providing to the medical caregiver of specific biomarker parameters for identifying or quantifying in the primary analytical data a signal for the biomarker(s) of interest (e.g., full length cytostatin C polypeptide, and a C-terminal cystatin C polypeptide fragment). Examples of primary analytical data include, but are not limited to, e.g., mass spectrometry spectra, HPLC spectra, images of stained or otherwise processed one or two dimensional gels, or images of capture arrays. Examples of specific biomarker parameters include, e.g., molecular weight values determined by mass spectrometry, m/z values, molecular weight values determined by gel electrophoresis, isoelectric point, position, in a capture array, of a capture moiety (e.g., an antibody) for one or more of the biomarkers disclosed herein (e.g., a C-terminal cystatin C polypeptide fragment). Examples of directly providing a specific biomarker parameter include, but are not limited to, providing mass spectrometry spectra of a biological sample from a subject of interest and specifically identifying the spectra peaks corresponding to any of the biomarkers for MS disclosed herein (e.g., those in Table 4A or 4B); providing gel images where specific spots are identified that correspond to any of the biomarkers for MS disclosed herein; providing protein capture array images and identifying array positions corresponding to any of the biomarkers for MS disclosed herein. Indirectly providing a specific biomarker parameter include, e.g., publicly providing (e.g., on the internet, in publications, in sales literature, in lectures, videos, and the like), a specific biomarker parameter (e.g., molecular weight values) or references to sources that provide the specific biomarker parameter in question specific biomarkers, separately from a particular subject's biomarker analysis. In some embodiments, the methods described herein include, in addition to indirectly providing the specific biomarker parameter, providing an indication of the value of the biomarker parameter for diagnosing MS or a related condition is also provided.

Measurement and Detection of Biomarkers

Levels of the biomarkers described herein can be determined using a wide range of conventional techniques.

In some embodiments, levels of biomarkers disclosed herein are measured by mass spectroscopy, which allows direct measurements of analytes with high sensitivity and reproducibility. A number of suitable mass spectrometric methods are known: Electrospray ionization (ESI), for example, allows quantification of differences in relative concentration of various species in one sample against another, and is thus particularly suitable for determining ratios of biomarkers as described herein; absolute quantification using ESI is also possible by including normalization techniques (e.g., using an internal standard) in the ESI assay. Matrix-assisted laser desorption ionization (MALDI) or the related SELDI technology (Ciphergen, Inc.) also could be used to make a determination of whether a biomarker is present, and the relative or absolute level of the biomarker. Further, mass spectrometers that allow time-of-flight (TOF) measurements have high accuracy and resolution and are able to measure low abundant species, even in complex biological mixtures like CSF or serum.

In some embodiments, the level of the biomarkers is determined using a standard immunoassay, such as sandwiched ELISA using matched antibody pairs conjugated to detectable moieties (e.g., fluorescent, luminescent, or enzymatic moieties). Commercially available or custom monoclonal or polyclonal antibodies are typically used. However, the assay can be adapted for use with other reagents that specifically bind to the biomarker. Standard protocols and data analysis are used to determine the biomarker concentrations from the assay data.

In other embodiments, where levels of a protein biomarker are to be determined, quantification can is based on derivatization in combination with isotopic labeling, referred to as isotope coded affinity tags ("ICAT"). In this and other related methods, a specific amino acid in two samples is differentially and isotopically labeled and subsequently separated from peptide background by solid phase capture, wash and release. The intensities of the molecules from the two sources with different isotopic labels can then be accurately quantified with respect to one another.

In some embodiments, one- and two-dimensional gels are used to separate proteins and quantify gels spots corresponding to the biomarker(s) of interest, e.g., by silver staining, fluorescence, or radiolabeling. The identity of gel spots can be further confirmed using mass spectroscopy techniques.

In other embodiments, the biomarkers are measured using mass spectroscopy in combination with a separation technology, e.g., liquid chromatography-mass spectroscopy or gas chromatography-mass spectroscopy. Reverse-phase liquid chromatography may be coupled to high resolution, high mass accuracy ESI time-of-flight (TOF) mass spectroscopy. This allows spectral intensity measurement of a large number of biomolecules from a relatively small amount of any complex biological material without sacrificing sensitivity or throughput. Analyzing a sample will allow the biomarker (specified by a specific retention time and m/z) to be determined and quantified.

Many other separation technologies may be used in connection with mass spectroscopy. For example, a vast array of separation columns are commercially available. In addition, separations may be performed using custom chromatographic surfaces (e.g., a bead on which a biomarker specific reagent has been immobilized). Molecules retained on the media subsequently may be eluted for analysis by mass spectroscopy.

As an example, an antibody may be used to isolate a biomarker provided herein in a biological sample (e.g., by immunoprecipitation from a biological sample). In an exemplary embodiment, a biological sample is contacted with an antibody affixed to a solid support (such as a bead or solid surface) to a biomarker described herein, and the biomarker becomes tethered to the support by virtue of being bound to the antibody affixed to the solid support. The solid support containing the antibody-biomarker complex is washed under conditions which allow the antibody to remain bound to the biomarker. Non-specific components of the sample are thus separated and removed from the presence of the biomarker, with the biomarker remaining tethered to the support. The resulting composition thus becomes enriched with biomarker as a result of the concentration of the biomarker in the sample and the removal of non-marker components of the sample. The level of the biomarker may then be determined by any of a number of methods. The antibody-marker complex may be detected, or the biomarker may be eluted from the antibody and detected. As an example, the antibody-biomarker complex or eluted biomarker may be subjected to any number of methods for determining size, such as spectroscopy, chromatographic separations, or 2-D gel separations.

Analysis by liquid chromatography-mass spectroscopy produces a mass intensity spectrum, the peaks of which represent various components of the sample, each component having a characteristic mass-to-charge ratio (m/z) and retention time (r.t.). The presence of a peak with the m/z and retention time of a biomarker indicates that the biomarker is present. The peak representing a biomarker may be compared to a corresponding peak from another spectrum (e.g., from a control sample) to obtain a relative measurement. Any standard normalization technique (e.g., an internal standard) may be used when a quantitative measurement is desired. In addition, deconvoluting software is available to separate overlapping peaks. The retention time depends to some degree on the conditions employed in performing the liquid chromatography separation.

In some embodiments, the mass spectrometer used in the methods described herein provides high mass accuracy and high mass resolution (e.g., the Waters-Micromass TOF instrument).

A number of the assays discussed above employ a reagent that specifically binds to the biomarker (i.e., a "biomarker specific reagent"). Essentially any molecule that is capable of specifically binding to a biomarker described herein can be used in the methods described herein. In some embodiments, the biomarker specific reagents are antibodies, or antibody fragments. In other embodiments, the biomarker specific reagents are non-antibody species. Thus, for example, a biomarker specific reagent may be an enzyme for which the biomarker is a substrate. The biomarker-specific reagents may recognize any epitope of the targeted biomarkers.

A biomarker specific reagent may be identified and produced by any method accepted in the art. Methods for identifying and producing antibodies and antibody fragments specific for an analyte are well known. Examples of other methods used to identify biomarker specific reagents include binding assays with random peptide libraries (e.g., phage display) and design methods based on an analysis of the structure of the biomarker.

The chromatographic separation techniques described above also may be coupled to an analytical technique other than mass spectroscopy such as fluorescence detection of tagged molecules, NMR, capillary UV, evaporative light scattering or electrochemical detection.

Methods for Monitoring the Progression of MS or a Related Condition

In some embodiments provided herein is a method is for monitoring an MS patient over time to determine whether the disease is progressing. The specific techniques used in implementing this embodiment are similar to those used in the embodiments described above. The method is performed by analyzing a biological sample, such as serum or CSF, obtained from the subject at a certain time ($t_1$), where the analyzing includes measuring the level of at least one of the biomarkers described herein; and comparing the measured level with the level measured with respect to a biological sample obtained from the subject at an earlier time ($t_0$). Depending upon the difference between the measured levels, it can be seen whether the biomarker level has increased, decreased, or remained constant over the interval ($t_1$-$t_0$). A further deviation of a biomarker in the direction indicating MS or a condition relating thereto, or the measurement of additional increased or decreased MS biomarkers, would suggest a progression of the disease during the interval. Subsequent sample acquisitions and measurements can be performed as many times as desired over a range of times $t_2$ to $t_n$.

In addition to indicating a progression of the disease, tracking a biomarker level in a patient can be used to predict exacerbations or indicate the clinical course of the disease. For example, the biomarkers described herein could be further investigated to distinguish between any or all of the known forms of MS (CIS, benign MS, relapsing remitting MS, secondary chronic progressive MS, and primary progressive MS) or any described types or subtypes of the disease. In addition, the sensitivity and specificity of any method of the present invention could be further investigated with respect to distinguishing MS or a condition relating thereto from other diseases of autoimmunity, or other nervous system disorders, or to predict relapse and remission.

Methods for Monitoring and Optimizing Therapies for MS or a Related Condition

In some embodiments, the biomarkers described herein are used to assess the efficacy of a therapeutic intervention in a subject. The same approach described above is used, except a suitable treatment is started, or an ongoing treatment is changed, before the second measurement (i.e., after $t_0$ and before $t_1$). The treatment can be any therapeutic intervention, such as drug administration, dietary restriction or surgery, and can follow any suitable schedule over any time period. The measurements before and after could then be compared to determine whether or not the treatment was effective.

In some embodiments, the biomarkers described herein are used to optimize treatment of multiple sclerosis or a related condition in a subject by comparing the level of a biomarker or a ratio of two biomarkers determined in a first biological sample obtained from a subject prior to the treatment to the level of the biomarker or ratio of the two biomarkers determined in a second biological sample obtained from the subject after the beginning of the treatment. A biomarker level or ratio in the second sample that deviates further from a control level reference value or control ratio reference value than do the corresponding values in the first sample indicates that the treatment is likely ineffective and should be altered. Altered treatments include, but are not limited to, alternative dose regimens, treatment with additional agents, or substitution of at least one therapeutic agent with another therapeutic agent.

On the other hand, a biomarker level or ratio in the second sample that is closer or equal to a control level reference value than are the corresponding values in the first sample indicates that the treatment is likely to be effective and should be continued.

The time interval between obtaining the first and second biological samples can be anywhere from about 8 hours to about a year, e.g., 1 day, 2 days, 3 days, 4 days, 1 week, 2 weeks, 3 weeks, 4 weeks, 5 weeks, 2 months, 3 months, 4 months, 5 months, 6 months, 7 months, 8 months, 9 months, 10 months, 11 months, or a full year.

In some embodiments, biomarker levels or biomarker ratios are determined for biological samples obtained at regular intervals throughout the treatment period, including but not limited to, once per week, once per 10 days, once per two weeks, once per months, once per two months, once per three months, once per 4 months, or once per 6 months.

In some embodiments, the level of a cystatin C protein fragment lacking about 8 amino acids at its C-terminus is determined in the first and second biological sample.

In some embodiments, the ratio of a cystatin C protein fragment lacking about 8 amino acids at its C-terminus to full length cystatin C protein is determined in the first and second biological samples.

A biomarker may also be used to screen a candidate drug in a longitudinal clinical trial to determine whether a candidate drug is effective in treating MS or a condition relating thereto. At time $t_0$, a biological sample is obtained from each subject in population of subjects diagnosed with MS or a condition relating thereto. Next, assays are performed on each subject's sample to measure levels of a biological biomarker. In some embodiments, only a single biomarker is monitored, while in other embodiments, a combination of biomarkers is monitored. Next, a predetermined dose of a candidate drug is administered to a portion or sub-population of the same subject population. Drug administration can follow any suitable schedule over any time period. In some cases, varying doses are administered to different subjects within the sub-population, or the drug is administered by different routes. At time $t_1$, after drug administration, a biological sample is acquired from the sub-population and the same assays are performed on the biological samples as were previously performed to obtain measurement values. As before, subsequent sample acquisitions and measurements can be performed as many times as desired over a range of times $t_2$ to $t_n$. In such a study, a different sub-population of the subject population may serve as a control group, to which a placebo is administered. The same procedure may be followed for the control group: obtaining the biological sample, processing the sample, and measuring the biological biomarkers to obtain a measurement chart.

Specific doses and delivery routes can also be examined. The method is performed by administering the candidate drug at specified dose or delivery routes to subjects with MS or a condition relating thereto; obtaining biological samples, such as serum or CSF, from the subjects; measuring the level of at least one of the biomarkers in each of the biological samples; and, comparing the measured level for each sample with a control level reference value. Typically, in a longitudinal study, the control level reference value is determined by measuring the level of the biomarker(s) in the subject before drug administration. Depending upon the difference between the measured and standard levels, the drug can be considered to have an effect on MS or a condition relating thereto. If multiple biomarkers are measured, at least one and up to all of the biomarkers must change, in the expected direction, for the drug to be considered effective. In some embodiments, multiple biomarkers must change for the drug to be considered effective, and, in some embodiments, such change is statistically significant.

The above description is not limited to a candidate drug, but is applicable to determining whether any therapeutic intervention is effective in treating MS or a condition relating thereto.

As indicated in Tables 2 (FIG. 11) 4A (FIG. 16) and 4B (FIG. 17), some of the biomarkers described herein occur at higher levels in samples from MS patients than in control subjects, while other biomarkers occur at lower levels in MS patient samples than in control subject samples. The p-values shown were obtained by univariate analysis. A significant change in the appropriate direction in the measured value of one or more of the biomarkers indicates that the drug is effective. If only one biomarker is measured, then that value must increase or decrease to indicate drug efficacy. If more than one biomarker is measured, then drug efficacy can be indicated by change in only one biomarker, all biomarkers, or any number in between. In some embodiments, multiple biomarkers are measured, and drug efficacy is indicated by changes in multiple biomarkers. Measurements can be of the biomarkers described herein and other measurements and factors associated with MS or a related condition (e.g., measurement of biomarkers reported in the literature such as antibodies against (alpha)B crystallin, and MRI imaging). Furthermore, the magnitude of change in a biomarker level, particularly when compared to a control level reference value may be an indication of the relatively efficacy of the drug.

Polypeptides

As described herein, one of the biomarker polypeptides that is significantly dysregulated in patients with MS or CIS is a proteolytic fragment of cystatin C. Thus, provided herein is a composition comprising a C-terminal cleavage product of cystatin C. In one aspect, the C-terminal cleavage product comprises a deletion of amino acids from the C-terminus. In some embodiments, the cystatin C cleavage product is a cystatin C polypeptide that lacks exactly 8, about 8, or at least 8 amino acids at its C-terminus.

Human cystatin C is a 146 amino acid polypeptide with Accession number NP_000090 on the NCBI website. The full-length human cystatin C polypeptide sequence (SEQ ID NO:4) is shown below:

```
                                                        (SEQ ID NO: 4)
  1 MAGPLRAPLL LLAILAVALA VSPAAGSSPG KPPRLVGGPM DASVEEEGVR RALDFAVGEY

61 NKASNDMYHS RALQVVRARK QIVAGVNYFL DVELGRTTCT KTQPNLDNCP FHDQPHLKRK

121 AFCSFQIYAV PWQGTMTLSK STCQDA
```

In some embodiments, the above-mentioned proteolytic fragment of cystatin C lacking exactly 8 contiguous C-terminal amino acids has an amino acid sequence corresponding to SEQ ID NO: 2:

```
                                                        (SEQ ID NO: 2)
  1 MAGPLRAPLL LLAILAVALA VSPAAGSSPG KPPRLVGGPM DASVEEEGVR RALDFAVGEY

61 NKASNDMYHS RALQVVRARK QIVAGVNYFL DVELGRTTCT KTQPNLDNCP FHDQPHLKRK

121 AFCSFQIYAV PWQGTMTL
```

Provided herein are polypeptides the amino acid sequence of which comprises, consists essentially of, or consists of an amino acid sequence that is at least about 70%, 75%, 80%, 85%, 90%, 95%, 98%, 99%, or 100% identical to SEQ ID NO: 2. Preferably, such polypeptides do not comprise the last 8 C-terminal amino acids of full-length cystatin C. In some embodiments, the polypeptides provided herein comprise an amino acid sequence that differs from SEQ ID NO: 2 in one or more, e.g., 1, 2, 3, 4, 5 or 10, amino acid substitutions, additions or deletions. The amino acid changes may be conservative amino acid changes. Polypeptides comprising at least 4, 10, 20, 30, 50, 100 or 130 contiguous amino acids of SEQ ID NO: 2 are also encompassed. Polypeptides may have a molecular weight of approximately between 7 kDa and 12.5 kDa.

Preferably, the polypeptides are biologically active, i.e., they retain at least one biological activity of wild-type cystatin C, e.g., inhibition of cathepsin B. For example, the polypeptides described in the previous paragraph may exhibit a biological function of a protein comprising an amino acid sequence consisting of SEQ ID NO: 2. Certain polypeptides have a stronger biological activity than wild-type cystatin C, e.g., at least about 50%, 2 fold, 3 fold, 5 fold or more stronger. Other polypeptides may have an activity that is similar or identical to that of wild-type cystatin C. Biological activity of cystatin C may be determined as described in the examples.

Other polypeptides provided herein are cystatin C fragments lacking the N-terminal 8 amino acids, and cystatin C fragments lacking both the N-terminal 8 amino acids and the C-terminal 8 amino acids, e.g.,

```
                                                        (SEQ ID NO: 5)
LLAILAVALA VSPAAGSSPG KPPRLVGGPM DASVEEEGVR

RALDFAVGEY NKASNDMYHS RALQVVRARK QIVAGVNYFL

DVELGRTTCT KTQPNLDNCP FHDQPHLKRK AFCSFQIYAV

PWQGTMTLSK STCQDA (SEQ ID NO: 7)
LLAILAVALA VSPAAGSSPG KPPRLVGGPM DASVEEEGVR

RALDFAVGEY NKASNDMYHS RALQVVRARK QIVAGVNYFL

DVELGRTTCT KTQPNLDNCP FHDQPHLKRK AFCSFQIYAV

PWQGTMTL
```

Cystatin C fragment polypeptides lacking the 8 N-terminal amino acids generally have a lower biological activity relative to the wild-type cystatin C or cystatin C fragments lacking C-terminal fragments. Homologs of such protein, e.g., comprising, consisting of, or consisting essentially of an amino acid sequence that is at least about 70%, 80%, 90%, 95%, 98% or 99% identical to SEQ ID NO: 5 or 7 are also encompassed.

In some embodiments, a cystatin C polypeptide fragment is covalently linked, directly or indirectly, to one or more amino acids or to one or more heterologous peptides, e.g., to form a fusion polypeptide. Examples of heterologous peptides to be fused, include, but are not limited to peptides that can be used for detecting; purifying; stabilizing; or solubilizing the cystatin C fusion polypeptide (e.g., TAG peptide, FLAG tag, or a His6 tag (SEQ ID NO: 9)).

In some embodiments, the cystatin-C fragment polypeptide is linked to an immunoglobulin (Ig) constant heavy or light chain domain or portion thereof. For example, it may be linked to a CH1, CH2 and/or CH3 domain of a heavy chain. If the constant region is from a light chain, it may be from a kappa or lambda light chain. If the constant region is from a heavy chain, it may be from an antibody of any one of the following classes of antibodies: IgG, IgA, IgE, IgD, and IgM. IgG may be IgG1, IgG2, IgG3 or IgG4. The constant domain may be an Fc fragment. The constant domain may be from a mammalian antibody, e.g., a human antibody. Soluble receptor-IgG fusion proteins can be generated by methods found in, e.g., U.S. Pat. Nos. 5,225,538, 5,726,044; 5,707,632; 750, 375, 5,925,351, 6,406,697 and Bergers et al. Science 1999 284: 808-12). In some embodiments, the immunoglobulin amino acid sequence corresponds to the constant part of the heavy chain of human IgG, particularly IgG1, where dimerization between two heavy chains takes place at the hinge region. It is recognized that inclusion of the CH2 and CH3 domains of the Fc region as part of the fusion polypeptide increases the in vivo circulation half-life of the polypeptide comprising the Fc region, and that of the oligomer or dimer comprising the polypeptide.

Constant Ig domains may also contain one or more mutations that reduce or eliminate one or more effector functions, e.g., binding to Fc receptors and complement activation (see, e.g., S. Morrison, Annu. Rev. Immunol., 10, pp. 239-65 (1992); Duncan and Winter (1988) Nature 332: 738-740; and Xu et al. (1994) J. Biol. Chem. 269: 3469-3474). For example, mutations of amino acids corresponding to Leu 235 and Pro 331 of human IgG1 to Glu and Ser respectively, are provided. Such constructs are further described in U.S. Pat. No. 6,656,728.

The constant Ig domain may be linked to the N-terminus or C-terminus of a peptide.

In some embodiments, a peptide, polypeptide, or moiety is linked to the cystatin C fragment polypeptide through a linker sequence which may comprise a cleavage site for a selected protease, e.g., thrombin. For example a linker may comprise a thrombin cleavage site. An exemplary nucleotide sequence encoding such a site has the following nucleotide sequence: 5' TCT AGA GGT GGT CTA GTG CCG CGC GGC AGC GGT TCC CCC GGG TTG CAG 3' (SEQ ID NO: 6), which encodes a peptide having the amino acid sequence: Ser Arg Gly Gly Leu Val Pro Arg Gly Ser Gly Ser Pro Gly Leu Gln (SEQ ID NO: 8).

In some embodiments, a fusion polypeptide may also be fused to a signal sequence such that it is secreted from a cell in which it is expressed.

In some embodiments, a cystatin C fragment polypeptide is linked to a moiety, such as a polymer. The polymer need not have any particular molecular weight. In some embodiments, the molecular weight is between about 300 and 100,000. In other embodiments, the molecular weight is between 10,000 and 40,000. In particular, sizes of 20,000 or more are best at preventing protein loss due to filtration in the kidneys. Exemplary polymers include water-soluble degradable or non-degradable polymer. The polymer may be a copolymer comprising an acrylic polymer, alkene polymer, urethane polymer, amide polymer, polyimine, polysaccharide, or ester polymer. Alternatively, the polymer is polyglutamate, a polysaccharide such as dextran or dextrin-2-sulphate, polyvinylpyrolidone, a copolymer of divinylether and maleic anhydride (DIVEMA), or a copolymer of polethylene glycol and aspartic acid. In certain instances, the polymer is a linear or branched polyethylene glycol.

A polymer may be a homopolymer of polyethylene glycol (PEG) or is a polyoxyethylated polyol, wherein, preferably, the polymer is soluble in water at room temperature. Non-limiting examples of such polymers include polyalkylene oxide homopolymers such as PEG or polypropylene glycols, polyoxyethylenated glycols, copolymers thereof and block copolymers thereof, provided that the water solubility of the block copolymer is maintained. Examples of polyoxyethylated polyols include, for example, polyoxyethylated glycerol, polyoxyethylated sorbitol, polyoxyethylated glucose, or the like.

A fusion polypeptide may be bonded directly to a polymer or bonded to a polymer via a linking group. The polymer may be bonded to an amino acid at the N-terminus or the C-terminus of the peptide. In certain instances, the polymer is bonded to the nitrogen atom of the N-terminus amino acid of the peptide. Alternatively, the polymer may be bonded to the sulfur atom of a cysteine residue or to a lysine or arginine residue. Other sites are also possible.

In some embodiments, the polypeptides described herein may are fused to a peptide that facilitates labeling of the protein or allows linkage to another moiety. In an exemplary embodiment, an 11-residue peptide with the sequence DSLEFIASKLA (SEQ ID NO: 10) ("YBBR tag") is fused to the N- or C-terminus of the polypeptide, or inserted, e.g., in a flexible loop, in the middle of the protein (Yin et al. (2005) PNAS 102:15815). Functionally homologous peptides, which form an alpha-helix, may also be used. This peptide can then be labeled site specifically by Sfp phosphopantetheinyl transferase-catalyzed small-molecule CoA modification. The following labels may be attached: biotin, glutathione, fluorescent probes such as fluorescein, Alexa Fluor dyes, and redox probes such as porphyrin. Labeling can be performed as described in Yin et al., supra.

Also included are recombinant polypeptides which have been modified using standard molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids.

The recombinant polypeptides may also comprise one or more non-naturally occurring amino acids. For example, non-classical amino acids or chemical amino acid analogs can be introduced as a substitution or addition into peptides. Non-classical amino acids include, but are not limited to, the D-isomers of the common amino acids, 2,4-diaminobutyric acid, alpha-amino isobutyric acid, 4-aminobutyric acid, Abu, 2-amino butyric acid, gamma-Abu, epsilon-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, beta-alanine, fluoro-amino acids, designer amino acids such as beta-methyl amino acids, Calpha-methyl amino acids, Nalpha-methyl amino acids, and amino acid analogs in general.

Also provided are derivatives of peptides and proteins, such as chemically modified peptides and peptidomimetics. Peptidomimetics are compounds based on, or derived from, peptides and proteins. Peptidomimetics can be obtained by structural modification of known peptide sequences using unnatural amino acids, conformational restraints, isosteric replacement, and the like. The subject peptidomimetics constitute the continuum of structural space between peptides and non-peptide synthetic structures; peptidomimetics may be useful, therefore, in delineating pharmacophores and in helping to translate peptides into nonpeptide compounds with the activity of the parent peptides.

Additionally, peptidomimetics based on more substantial modifications of the backbone of a peptide can be used. Peptidomimetics which fall in this category include (i) retro-inverso analogs, and (ii) N-alkyl glycine analogs (so-called peptoids).

In addition to a variety of sidechain replacements which can be carried out to generate peptidomimetics, the description specifically contemplates the use of conformationally restrained mimics of peptide secondary structure. Numerous surrogates have been developed for the amide bond of peptides. Frequently exploited surrogates for the amide bond include the following groups (i) trans-olefins, (ii) fluoroalkene, (iii) methyleneamino, (iv) phosphonamides, and (v) sulfonamides.

Peptides may comprise at least one amino acid or every amino acid that is a D stereoisomer. Other peptides may comprise at least one amino acid that is reversed. The amino acid that is reversed may be a D stereoisomer. Every amino acid of a peptide may be reversed and/or every amino acid may be a D stereoisomer.

In another illustrative embodiment, a peptidomimetic can be derived as a retro-enantio analog of a peptide. Retro-enantio analogs such as this can be synthesized with commercially available D-amino acids (or analogs thereof) and standard solid- or solution-phase peptide-synthesis techniques, as described, e.g., in WO 00/01720. The final product may be purified by HPLC to yield the pure retro-enantio analog.

Also included are peptide derivatives which are differentially modified during or after synthesis, e.g., by benzylation, glycosylation, acetylation, phosphorylation, amidation, pegylation, derivatization by known protecting/blocking groups, proteolytic cleavage, linkage to an antibody molecule or other cellular ligand, etc. In specific embodiments, the peptides are acetylated at the N-terminus and/or amidated at the C-terminus.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

A peptide (or polypeptide) may also be fused to a signal sequence. For example, when prepared recombinantly, a nucleic acid encoding the peptide may be linked at its 5' end to a signal sequence, such that the peptide is secreted from the cell.

Polypeptides (or peptides) may be used as a substantially pure preparation, e.g., wherein at least about 90% of the polypeptides in the preparation are the desired polypeptide. Compositions comprising at least about 50%, 60%, 70%, or 80% of the desired peptide may also be used. The polypeptides may also be encompassed in pharmaceutical compositions, e.g., comprising a pharmaceutically acceptable vehicle.

Polypeptides described herein may be used as immunogens for the production of antibodies. For such use, e.g., the polypeptides may be in a composition with an adjuvant.

Proteins corresponding to the other peaks described in Table 2 and Table 4 are also encompassed. Exemplary polypeptides are those associated with the 12.5 kDa peak (Table 2 and Table 4 (peak A)), the 3.9 kDa peak (Table 2 and Table 4 (peak F)), the 13.4 kDa peak (Table 2 and Table 4 (peak J)), the 13.6 kDa peak (Table 2 and Table 4 (peak N)), and the 4.7 kDa peak (Table 4 (peak Q)). Fragments and variants of such polypeptides are also included within the scope of the compositions described herein.

Nucleic Acids

Provided herein are nucleic acids (also referred to herein as "polynucleotides") encoding a C-terminal cleavage product of cystatin C. In some embodiments, the cystatin C cleavage product is a cystatin C polypeptide that lacks exactly 8, about 8, or at least 8 amino acids (e.g., at least 9, 10, 11, 12, 13, 14, 15, 16, 17, 18, 19, or 20 amino acids) at its C-terminus.

Accordingly, in some embodiments provided herein is an isolated polynucleotide which encodes a C-terminal cleavage product of a cystatin C polypeptide, or fragment thereof, e.g., those described herein. Isolated polynucleotides that encode polypeptides with higher sequence homologies of, for example, 70%, 80%, 90%, 95% or 98%, which have the ability to inhibit cathepsin B activity more so than full-length cystatin C, are also contemplated herein. In some embodiments, an isolated polynucleotide encodes a cystatin C fragment comprising an amino acid sequence consisting essentially of SEQ ID NO: 2.

In some embodiments, an isolated polynucleotide encodes a polypeptide comprising at least 4, 10, 20, 30, 50, 100 or 130 contiguous amino acids of SEQ ID NO: 2, wherein said polypeptide does not comprise the last 8 amino acids of full-length cystatin C. In some embodiments, the encoded polypeptide inhibits cathepsin B proteolytic activity. In some embodiments, the ability of the encoded polypeptide to inhibit cathepsin B proteolytic activity is greater than that of than full-length cystatin C. In some embodiments, the isolated polynucleotide encodes a polypeptide representing a cystatin C cleavage product with activity similar to or identical to SEQ ID NO:2. In some embodiments, the isolated polynucleotide encodes a polypeptide the amino acid sequence of which is at least 70% to 100% identical to SEQ ID NO:2, e.g., 75%, 80%, 85%, 90%, 95%, 100%, or any other % identical to SEQ ID NO:2 from about 70 to 100%.

In another embodiment, the polynucleotide encodes a fusion polypeptide comprising the amino acid sequence of one the above-described cystatin C polypeptide fragments fused to a heterologous amino acid sequence.

The human cystatin C cDNA is an 818 nucleotide sequence (GenBank Accession No. NM_000099). The open reading frame encoding full-length cystatin C (SEQ ID NO:3) consists of nucleotides 76 to 490 (SEQ ID NO:3) and is shown below:

```
                                             (SEQ ID NO: 3)
ATG GCC GGG CCC CTG CGC GCC CCG CTG CTC CTG CTG

GCC ATC CTG GCC GTG GCC CTG GCC GTG AGC CCC GCG

GCC GGC TCC AGT CCC GGC AAG CCG CCG CGC CTG GTG

GGA GGC CCC ATG GAC CCC AGC GTG GAG GAG GAG GGT

GTG CGG CGT GCA CTG GAC TTT GCC GTC GGC GAG TAC

AAC AAA GCC AGC AAC GAC ATG TAC CAC AGC CGC GCG

CTG CAG GTG GTG CGC GCC CGC AAG CAG ATC GTA GCT

GGG GTG AAC TAC TTC TTG GAC GTG GAG CTG GGC CGA

ACC ACG TGT ACC AAG ACC CAG CCC AAC TTG GAC AAC

TGC CCC TTC CAT GAC CAG CCA CAT CTG AAA AGG AAA

GCA TTC TGC TCT TTC CAG ATC TAC GCT GTG CCT TGG

CAG GGC ACA ATG ACC TTG TCG AAA TCC ACC TGT CAG

GAC GCC TAG
```

The nucleotide sequence encoding a human cystatin C fragment lacking the 8 C-terminal amino acids (SEQ ID NO:1) is set forth below:

```
                                             (SEQ ID NO: 1)
ATG GCC GGG CCC CTG CGC GCC CCG CTG CTC CTG CTG

GCC ATC CTG GCC GTG GCC CTG GCC GTG AGC CCC GCG

GCC GGC TCC AGT CCC GGC AAG CCG CCG CGC CTG GTG
```

-continued

```
GGA GGC CCC ATG GAC GCC AGC GTG GAG GAG GAG GGT

GTG CGG CGT GCA CTG GAC TTT GCC GTC GGC GAG TAC

AAC AAA GCC AGC AAC GAC ATG TAC CAC AGC CGC GCG

CTG CAG GTG GTG CGC GCC CGC AAG CAG ATC GTA GCT

GGG GTG AAC TAC TTC TTG GAC GTG GAG CTG GGC CGA

ACC ACG TGT ACC AAG ACC CAG CCC AAC TTG GAC AAC

TGC CCC TTC CAT GAC CAG CCA CAT CTG AAA AGG AAA

GCA TTC TGC TCT TTC CAG ATC TAC GCT GTG CCT TGG

CAG GGC ACA ATG ACC TTG TCG
```

In some embodiments, provided herein is an isolated polynucleotide encoding any of the cystatin C polypeptides described above. In some embodiments, the isolated polynucleotide is at least 60% (e.g., 65%, 70%, 75%, 80%, 85%, 90%, 95%, or 100%) identical to the polynucleotide sequence of SEQ ID NO: 1, wherein the polynucleotide sequence does not encode a polypeptide comprising the last 8 amino acids of full-length cystatin C. In some embodiments, the encoded polypeptide has an ability to inhibit cathepsin B activity that is greater than that of full-length cystatin C.

In other embodiments, provided herein is an isolated polynucleotide encoding a fragment of a cystatin C polypeptide, which fragment comprises a contiguous stretch of at least 4, 10, 20, 50, 100 or 130 amino acids of SEQ ID NO: 2, wherein said polypeptide does not comprise the last 8 amino acids of full-length cystatin C. In some embodiments, the recited fragment has the ability to inhibit cathepsin B activity that is greater than that of full-length cystatin C. The polynucleotide may encode a cystatin C fragment that has a molecular weight between about 7 kDa and 12.5 kDa.

In some embodiments, the polynucleotides set forth above encode a cystatin C cleavage product as described above. Such polynucleotides include genomic sequence, mRNA or cDNA, polymorphic, allelic, isoforms and mutant forms thereof, and nucleic acid constructs of the gene, including vectors, plasmids and recombinant cells and transgenic organisms containing or corresponding to cystatin C cleavage product.

Polynucleotides include vectors, such as expression vectors for producing a peptide, e.g., viral vectors.

Also encompassed herein are cells comprising a nucleic acid encoding a polypeptide described herein and methods for producing peptides comprising culturing these cells to produce a peptide. These methods can be used of producing recombinant peptides or for expression of a petpide in a cell, e.g., in a cell of a subject.

Appropriate vectors may be introduced into host cells using techniques such as infection, transduction, transfection, transvection, electroporation and transformation. The vector may be, for example, a phage, plasmid, viral or retroviral vector. Retroviral vectors may be replication competent or replication defective. In the latter case, viral propagation generally will occur only in complementing host cells.

The vector may contain a selectable biomarker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

In some embodiments, vectors comprise cis-acting control regions to the polynucleotide of interest. Appropriate trans-acting factors may be supplied by the host, supplied by a complementing vector or supplied by the vector itself upon introduction into the host.

In certain embodiments, the vectors provide for specific expression, which may be inducible and/or cell type-specific. In some embodiments, vectors are those inducible by environmental factors that are easy to manipulate, such as temperature and nutrient additives.

Expression vectors contemplated herein include chromosomal-, episomal- and virus-derived vectors, e.g., vectors derived from bacterial plasmids, bacteriophage, yeast episomes, yeast chromosomal elements, viruses such as baculoviruses, papova viruses, vaccinia viruses, adenoviruses, fowl pox viruses, pseudorabies viruses and retroviruses, and vectors derived from combinations thereof, such as cosmids and phagemids.

The DNA insert should be operatively linked to an appropriate promoter, such as the phage lambda PL promoter, the *E. coli* lac, trp and tac promoters, the SV40 early and late promoters and promoters of retroviral LTRs, to name a few. The expression constructs will further contain sites for transcription initiation, termination and, in the transcribed region, a ribosome binding site for translation. The coding portion of the mature transcripts expressed by the constructs will preferably include a translation initiating site at the beginning and a termination codon (UAA, UGA or UAG) appropriately positioned at the end of the polypeptide to be translated.

As indicated, the expression vectors will preferably include at least one selectable biomarker. Such biomarkers include dihydrofolate reductase or neomycin resistance for eukaryotic cell culture and tetracycline, kanamycin, or ampicillin resistance genes for culturing in *E. coli* and other bacteria. Representative examples of appropriate hosts include, but are not limited to, bacterial cells, such as *E. coli, Streptomyces* and *Salmonella typhimurium* cells; fungal cells, such as yeast cells; insect cells such as *Drosophila* S2 and Sf9 cells; animal cells such as CHO, COS and Bowes melanoma cells; and plant cells. Appropriate culture mediums and conditions for the above-described host cells are known in the art.

Among vectors for use in bacteria include pQE70, pQE60 and pQE9, pQE10 available from Qiagen; pBS vectors, Phagescript vectors, Bluescript vectors, pNH8A, pNH16a, pNH18A, pNH46A available from Stratagene; pET series of vectors available from Novagen; and ptrc99a, pKK223-3, pKK233-3, pDR540, pRIT5 available from Pharmacia. Among well-established eukaryotic vectors are pWLNEO, pSV2CAT, pOG44, pXT1 and pSG available from Stratagene; and pSVK3, pBPV, pMSG and pSVL available from Pharmacia.

Among bacterial promoters suitable for use in the methods described herein include the *E. coli* lad and lacZ promoters, the T3, T5 and T7 promoters, the gpt promoter, the lambda PR and PL promoters, the trp promoter and the xyl/tet chimeric promoter. Suitable eukaryotic promoters include the CMV immediate early promoter, the HSV thymidine kinase promoter, the early and late SV40 promoters, the promoters of retroviral LTRs, such as those of the Rous sarcoma virus (RSV), and metallothionein promoters, such as the mouse metallothionein-I promoter.

Introduction of the construct into the host cell can be effected by calcium phosphate transfection, DEAE-dextran mediated transfection, cationic lipid-mediated transfection, electroporation, transduction, infection or other methods.

Such methods are described in many standard laboratory manuals (for example, Davis, et al., Basic Methods In Molecular Biology (1986)).

Transcription of DNA encoding the polypeptides described herein by higher eukaryotes may be increased by inserting an enhancer sequence into the vector. Enhancers are cis-acting elements of DNA, usually about from 10 to 300 nucleotides that act to increase transcriptional activity of a promoter in a given host cell-type. Examples of enhancers include the SV40 enhancer, which is located on the late side of the replication origin at nucleotides 100 to 270, the cytomegalovirus early promoter enhancer, the polyoma enhancer on the late side of the replication origin, and adenovirus enhancers.

Also described herein are nucleic acids encoding splice variants or nucleic acids representing transcripts synthesized from an alternative transcriptional initiation site, such as those whose transcription was initiated from a site in an intron. Such homologues can be cloned by hybridization or PCR.

The polynucleotide sequence may also encode for a leader sequence, e.g., the natural leader sequence or a heterologous leader sequence. Alternatively, the nucleic acid can be engineered such that the natural leader sequence is deleted and a heterologous leader sequence inserted in its place. The term "leader sequence" is used interchangeably herein with the term "signal peptide". For example, the desired DNA sequence may be fused in the same reading frame to a DNA sequence which aids in expression and secretion of the polypeptide from the host cell, for example, a leader sequence which functions as a secretory sequence for controlling transport of the polypeptide from the cell. The protein having a leader sequence is a preprotein and may have the leader sequence cleaved by the host cell to form the mature form of the protein.

For secretion of the translated polypeptide into the lumen of the endoplasmic reticulum, into the periplasmic space or into the extracellular environment, appropriate secretion signals may be incorporated into the expressed polypeptide, for example, the amino acid sequence KDEL (SEQ ID NO: 11). The signals may be endogenous to the polypeptide or they may be heterologous signals.

In some embodiments, provided herein is a method for the use of the polynucleotide as set forth above for the production of a polypeptide to be used as an immunogen for the production of antibodies. Methods of production of the cleavage product, e.g. by recombinant means, are provided.

In a specific embodiment provided herein a recombinant cell harboring a polynucleotide described herein, capable of producing a polypeptide described above, (e.g. SEQ ID NO: 2). In another embodiment are uses of such a recombinant cell for the production of recombinant cystatin C cleavage product. A cystatin C cleavage product may be expressed from a polynucleotide encoding a cleavage product, or from a nucleic acid expressing a cystatin C polypeptide and thereafter cleaving the cystatin C by proteolytic digest to produce the cleavage product.

Nucleic acids that encode the biomarkers set forth in Table 2 and Table 4, e.g., the 12.5 kDa peak (Table 2), the 3.9 kDa peak (Table 2), the 13.4 kDa peak (Table 2), the 13.6 kDa peak (Table 2), and the 4.7 kDa peak (Table 4), fragments and variants of such polypeptides, are also contemplated herein.

In a specific embodiment provided herein is a recombinant cell producing a polypeptide described above, (e.g. SEQ ID NO: 2). In another embodiment provided herein is a method for the use of such a recombinant cell for the production of recombinant cystatin C cleavage product. A cystatin C cleavage product may be expressed from a nucleic acid expressing the same, or from a nucleic acid expressing a cystatin C polypeptide and thereafter cleaving the cystatin C by proteolytic digest to produce the cleavage product.

Antibodies

Antibodies binding specifically to the biomarkers described herein, e.g., in Table 2 and Table 4, are also encompassed herein.

In certain embodiments provided herein are antibodies that bind with high specificity to the cystatin C cleavage product polypeptides provided herein. Thus, antibodies that bind to a polypeptide comprising SEQ ID NOs: 2 or 4 are provided. In addition to antibodies generated against the full length polypeptide or cleavage product, antibodies may also be generated in response to smaller constructs comprising epitopic core regions. Antibodies that bind to any of the polypeptides described above are also provided.

Antibodies described herein may bind essentially only to a full-length cystatin C, e.g., an antibody may bind specifically to an epitope that is absent in the cleavage product (e.g. SEQ ID NO: 2), e.g., an antibody to a cystatin C epitope within the C-terminal most 8 amino acids of the full-length polypeptide, without significant cross-hybridization to the cleavage product. Other antibodies may detect both types of proteins. An antibody that binds to both a cystatin C full-length and C-terminal cleavage product may bind to an epitope within the region of amino acids 1-138 of the full-length, such as an N-terminal region.

An antibody may specifically recognize the C-terminal cystatin C cleavage product. The antibody may only bind to the C-terminal cystatin C cleavage product (e.g., SEQ ID NO: 2), without significant cross-hybridization to the full-length cystatin C polypeptide (e.g, SEQ ID NO: 4). In a diagnostic assay the antibody may be used to determine the level of the C-terminal cleavage product.

As used herein, the term "antibody" is intended to refer broadly to any immunologic binding agent such as IgG, IgM, IgA, IgD and IgE. The term "antibody" is used to refer to any antibody-like molecule that has an antigen binding region, and includes antibody fragments such as Fab', Fab, F(ab')$_2$, single domain antibodies (DABs), Fv, scFv (single chain Fv), hybrid antibodies, chimeric antibodies, humanized antibodies and the like. Techniques for preparing, characterizing, and using antibodies can be found in, e.g., Antibodies: A Laboratory Manual, Cold Spring Harbor Laboratory, 1988.

"Humanized" antibodies are also contemplated, as are chimeric antibodies from mouse, rat, or other species, bearing human constant and/or variable region domains, bispecific antibodies, recombinant and engineered antibodies and fragments thereof.

Monoclonal antibodies (MAbs) are recognized to have certain advantages, e.g., reproducibility and large-scale production. Suitable monoclonal antibodies include those of human, murine, monkey, rat, hamster, rabbit and even chicken origin.

A wide range of animal species can be used for the production of antisera. Typically the animal used for production of antisera is a rabbit, a mouse, a rat, a hamster, a guinea pig or a goat. Because of the relatively large blood volume of rabbits, a rabbit is a choice for production of polyclonal antibodies.

Antibody Conjugates

Also provided herein are antibodies against cystatin C cleavage products, generally of the monoclonal type, that are linked to one or more other agents to form an antibody conjugate. Any antibody of sufficient selectivity, specificity and affinity may be employed as the basis for an antibody conjugate. Such properties may be evaluated using conventional immunological screening methodology.

Certain examples of antibody conjugates are those conjugates in which the antibody is linked to a detectable label. "Detectable labels" are compounds or elements that can be detected due to their specific functional properties, or chemical characteristics, the use of which allows the antibody to which they are attached to be detected, and further quantified if desired. Another such example is the formation of a conjugate comprising an antibody linked to a cytotoxic or anti-cellular agent, as may be termed "immunotoxins" (described in U.S. Pat. Nos. 5,686,072, 5,578,706, 4,792,447, 5,045,451, 4,664,911 and 5,767,072, each incorporated herein by reference).

Antibody conjugates are useful as diagnostic agents in the methods described herein. Antibody diagnostics generally fall within two classes, those for use in in vitro diagnostics, such as in a variety of immunoassays, and those for use in vivo diagnostic protocols, generally known as "antibody-directed imaging."

Appropriate imaging agents and methods for their attachment to antibodies include, e.g., U.S. Pat. Nos. 5,021,236 and 4,472,509, both incorporated herein by reference. Certain attachment methods involve the use of a metal chelate complex employing, for example, an organic chelating agent such a DTPA attached to the antibody (U.S. Pat. No. 4,472,509). Monoclonal antibodies may also be reacted with an enzyme in the presence of a coupling agent such as glutaraldehyde or periodate. Conjugates with fluorescein biomarkers are prepared in the presence of these coupling agents or by reaction with an isothiocyanate.

Antibody conjugates may be used in vivo or in vitro. In vitro the antibody may be linked to a secondary binding ligand or to an enzyme (an enzyme tag) that will generate a colored product upon contact with a chromogenic substrate. Examples of suitable enzymes include urease, alkaline phosphatase, (horseradish) hydrogen peroxidase and glucose oxidase. Other secondary binding ligands included, e.g., biotin and avidin or streptavidin compounds. The use of such labels is exemplified in, e.g., U.S. Pat. Nos. 3,817,837; 3,850,752; 3,939,350; 3,996,345; 4,277,437; 4,275,149 and 4,366,241; each of which is incorporated herein by reference.

Also provided are screening methods. A method may comprise contacting cystatin C or a biologically active fragment thereof with an agent and determining whether (a) the agent binds to cystatin C or the biologically active fragment thereof and/or (b) the agent inhibits the activity of cystatin C. A biologically active fragment may be a cystatin fragment lacking one or more amino acids at its C-terminus, e.g., as further described herein. A method may further comprise determining whether it can prevent or treat MS, an early stage thereof, or a condition relating thereto, e.g., in an animal model. An agent may be, e.g., an antibody or a molecule, e.g., a small molecule.

Methods for Treating MS or a Condition Relating Thereto

Provided herein are methods of treating or preventing multiple sclerosis, comprising administering to an individual afflicted therewith or in need thereof a therapeutically effective amount of an agent that modulates the expression, levels, or activity of a biomarker provided herein.

Further provided herein are methods of treating multiple sclerosis, comprising administering to an individual afflicted therewith or in need thereof a therapeutically effective amount of an agent which decreases cathepsin activity. In one embodiment, the cathepsin activity decreased is cathepsin B activity. In some embodiments, the agent inhibits the activity of cathepsin B.

In another embodiment, the agent inhibits the activity of cystatin C by inhibiting the proteolytic cleavage of cystatin C. The agent may be a protease inhibitor, which prevents cleavage of the 8 C-terminal most amino acids of cystatin C, thereby inhibiting the activity of cystatin C. In another embodiment, the agent may inhibit the production of SEQ ID NO: 2. The agent may be an antibody, peptide, small molecule, or mimetic which binds to the cleavage site, thereby blocking cleavage of the C terminus of cystatin C, which in turn inhibits the production of SEQ ID NO: 2.

In some embodiments, the treatment methods described herein also include determining a level of cathepsin activity in a subject before and after the beginning of treatment for MS or a related condition. In some embodiments, cathepsin is determined in a biological sample from the subject by use of a fluorogenic peptide substrate comprising a cognate amino acid cleavage recognition site, e.g., the preferred cathepsin-B substrate sequence Arg-Arg labeled with amino-4-trifluoromethyl coumarin (AFP). In some embodiments, cathepsin activity (e.g., cathepsin B activity) can be determined in vivo in the subject using an infrared-dye labeled fluorogenic peptide probe as described in, Melancon et al. (2007), *Pharm Res.*, 24(6):1217-1224.

In further embodiments, the methods described herein include determining the ratio of the level of the cystatin C fragment lacking 8 C-terminal amino acids to full length cystatin C in a biological sample, and, when the ratio is higher than a control ratio reference value, administering to the subject a composition containing a therapeutically effective amount of a neuroprotective agent.

In some embodiments, the neuroprotective agent is a modified terpenoid having the structure of Formula (I):

$$\text{structure with } Y_2, Y_1, H_3C, R_1, R_2, O, O$$

wherein each compound of Formula I is in a substantially purified form; and $Y_1$ is O and $Y_2$ is OH, O-alkyl, O-(hydroxyalkyl) or O-(alkoxyalkyl); or $Y_1$ and $Y_2$ together form a furan group;

$R_1$ and $R_2$ together form a substituted cycloalkyl or cycloalkenyl group; and ----- is selected from =====, $$\bigtriangledown_O \text{, or } \diagup_{X_4} \text{,}$$

wherein $X_4$ and $R_2$ together form a substituted heteroalicyclic group provided that $R_1$ is H; or pharmaceutically acceptable salts, esters, prodrugs, or metabolites thereof;

or ester derivatives, saccharide derivatives, or —$(CH_2CH_3O)_n$ $CH_3$ derivatives thereof, where n is 1 to 100; and a pharmaceutically acceptable excipient.

In a further embodiment, the at least one compound of Formula I has a structure selected from:

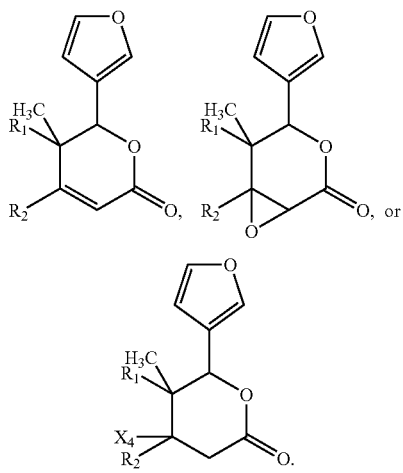

In a further embodiment, the at least one compound of Formula I has the structure:

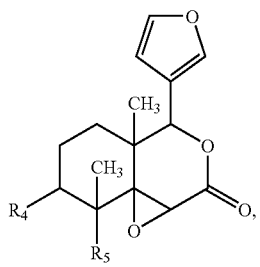

wherein $R_4$ and $R_5$ together form a substituted cycloalkyl or cycloalkenyl group.

In a further embodiment, the at least one compound of Formula I has the structure:

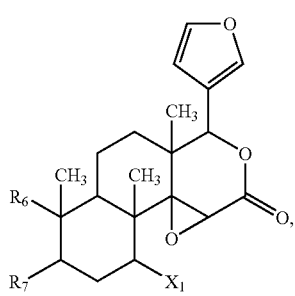

wherein $R_6$ and $R_7$ together form a substituted cycloalkyl or cycloalkenyl group; and
$X_1$ is selected from H, oxo, OH, O-alkyl, O-(hydroxyalkyl), O-(alkoxyalkyl), or O—C(O)-alkyl.

In a further embodiment, the at least one compound of Formula I has a structure selected from:

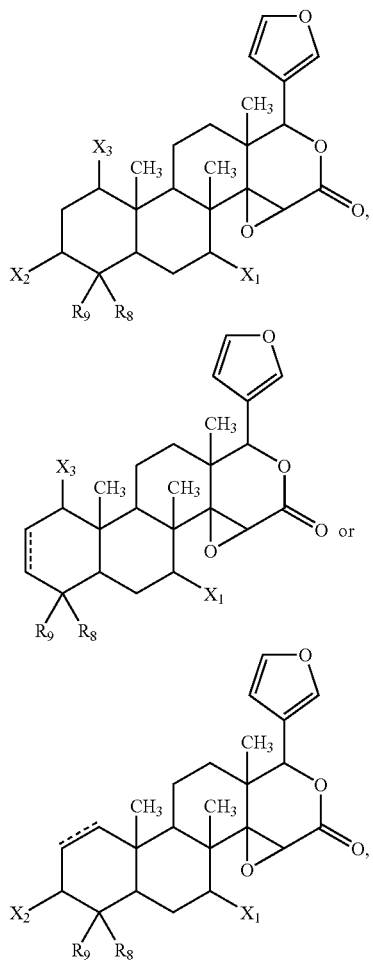

wherein $R_8$ and $R_9$ are independently H or alkyl;
$X_2$ and $X_3$ are independently selected from H, oxo, OH, O-alkyl, O-(hydroxyalkyl), O-(alkoxyalkyl), or O—C(O)-alkyl; and
------ is selected from ===== of

In a further embodiment, the at least one compound of Formula I has the structure:

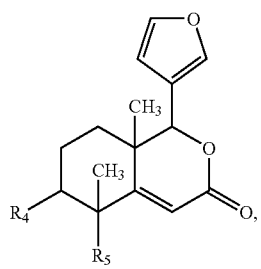

wherein $R_4$ and $R_5$ together form a substituted cycloalkyl or cycloalkenyl group.

In a further embodiment, the at least one compound of Formula I has the structure:

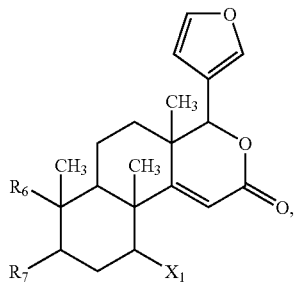

wherein $R_6$ and $R_7$ together form a substituted cycloalkyl or cycloalkenyl group; and
$X_1$ is selected from H, oxo, OH, O-alkyl, O-(hydroxyalkyl), O-(alkoxyalkyl), or O—C(O)-alkyl.

In a further embodiment, the at least one compound of Formula I has a structure selected from:

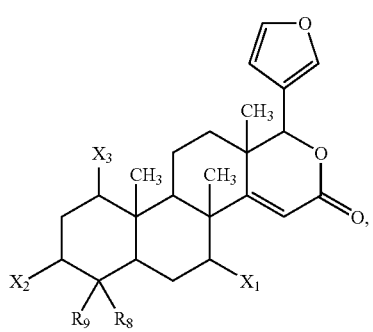

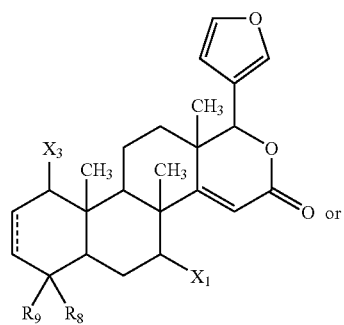

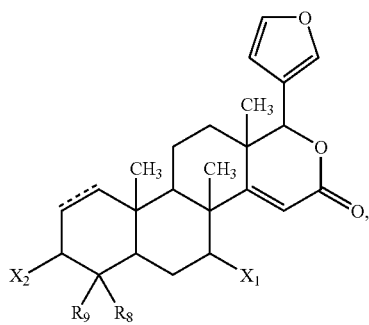

wherein $R_8$ and $R_9$ are independently H or alkyl;
$X_2$ and $X_3$ are independently selected from H, oxo, OH, O-alkyl, O-(hydroxyalkyl), O-(alkoxyalkyl), or O—C(O)-alkyl; and
------ is selected from ==== or

In a further embodiment, the at least one compound of Formula I has the structure:

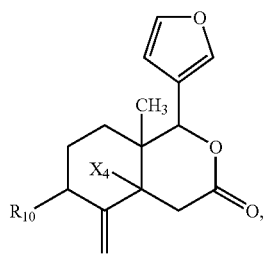

$X_4$ and $R_{10}$ together form a substituted heteroalicyclic group.

In a further embodiment, the at least one compound of Formula I has the structure:

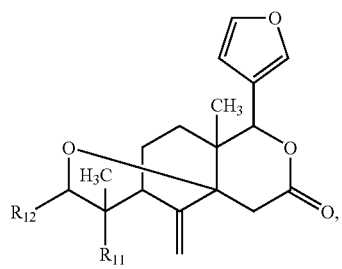

wherein $R_{11}$ and $R_{12}$ together form a substituted cycloalkyl or cycloalkenyl group.

In a further embodiment, the at least one compound of Formula I has the structure:

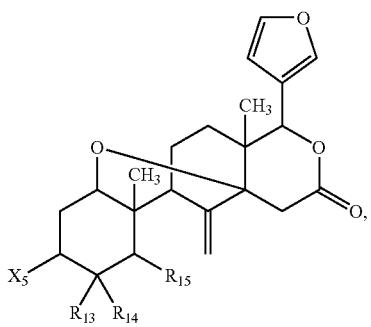

wherein $R_{13}$ and $R_{14}$ are independently H or alkyl;
$X_5$ is selected from H, oxo, OH, O-alkyl, O-(hydroxyalkyl), O-(alkoxyalkyl), or O—C(O)-alkyl; and
$R_{15}$ is alkyl-C(O)O-alkyl.

In another aspect provided herein is a pharmaceutical composition comprising at least one compound having the structure of Formula II:

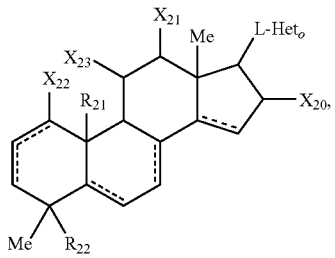

wherein Het$_O$ is a substituted or unsubstituted oxygen-containing aromatic or non-aromatic heterocycle; L is a bond or an alkylene group;
each ----- is independently selected from ═══,

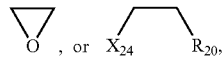

provided that no two adjacent ----- groups are adjacent ═══ or

groups;
each $X_{20}$, $X_{21}$, $X_{22}$, $X_{23}$, and $X_{24}$ is independently selected from H, oxo, OH, OC(O)-alkyl, O-(hydroxyalkyl), O-(alkoxyalkyl), or O-alkyl;
each $R_{20}$, $R_{21}$, and $R_{22}$ is selected from H or alkyl; or any two of $X_{20}$, $X_{21}$, $X_{22}$, $X_{23}$, $X_{24}$, $R_{20}$, $R_{21}$, or $R_{22}$ can form an optionally substituted oxygen-containing heterocycle; or pharmaceutically acceptable salts, esters, prodrugs, or metabolites thereof;
or ester derivatives, saccharide derivatives, or —(CH$_2$CH$_2$O)$_n$CH$_3$ derivatives thereof, where n is 1 to 100; and a pharmaceutically acceptable excipient.
In a further embodiment, the Het$_O$ is an unsubstituted furanyl group. In a further or alternative embodiment, L is a bond.
In a further or alternative embodiment, $R_{21}$ and $R_{22}$ are CH$_3$. In a further embodiment at least one of ----- groups is a ═══. In a further or alternative embodiment, at least one of ----- groups is a

In a further or alternative embodiment, at least one of ----- groups is a

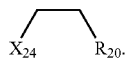

In a further or alternative embodiment, $X_{20}$ is an oxo group. In a further or alternative embodiment, the compound of Formula II is selected from:

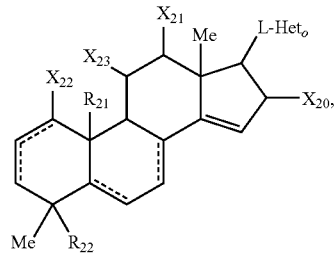

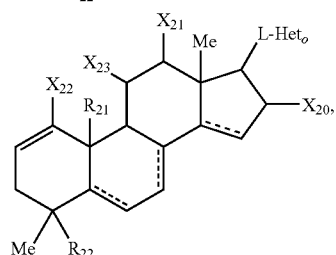

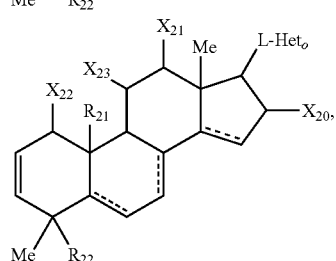

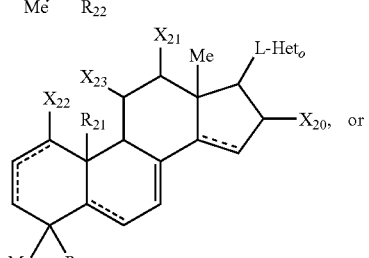

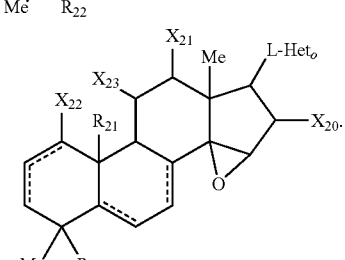

In a further or alternative embodiment, the pharmaceutical composition has a therapeutically effective amount of a compound presented in Table 5, (which are neuroprotective against the neurotoxin 3-NP), along with pharmaceutically acceptable excipients. In a further or alternative embodiment, the pharmaceutical composition has a therapeutically effective amount of a compound isolated from the plant families of order Rutales, including in Maliaceae and Rutaceae. In a further or alternative embodiment, the pharmaceutical composition has a therapeutically effective amount of a compound derived from a 4,4,8-trimethyl-17-furanylsteroid skeleton. In a further or alternative embodiment, the pharmaceutical composition has a therapeutically effective amount of a compound that is a tetranortriterpenoid.

TABLE 5

Modified Terpenoids having Significant 3-NP Neuroprotective Activity

| Compound | Structure | % Protection |
|---|---|---|
| 3alpha-ACETOXYDIHYDRODEOXYGUEDUNIN | 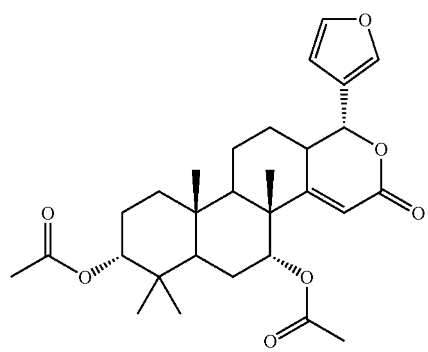 | 151 |
| 1,3-DIDEACETYLKHIVORIN | 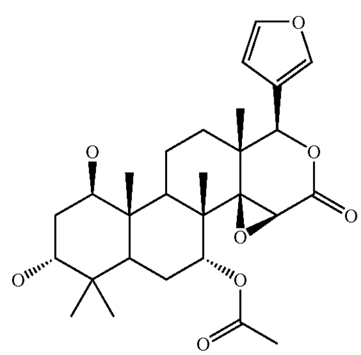 | 129 |
| DEOXODIHYDROGEDUNIN | 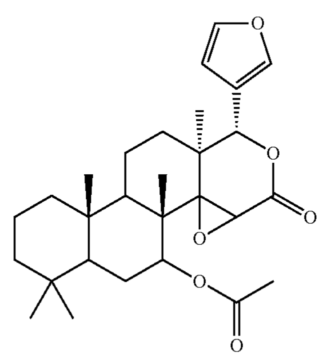 | 101 |
| 3beta-ACETOXYDEOXYANGOLENSIC ACID, METHYL ESTER | 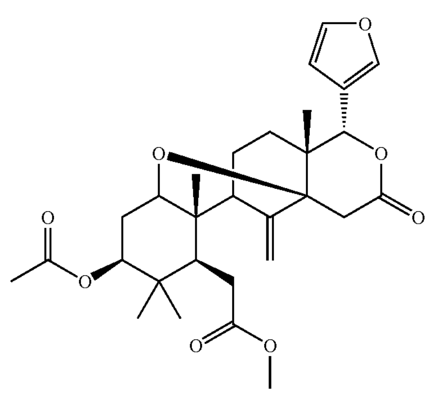 | 128 |

TABLE 5-continued

Modified Terpenoids having Significant 3-NP Neuroprotective Activity

| Compound | Structure | % Protection |
|---|---|---|
| TRIDESACETOXYKHIVORIN | 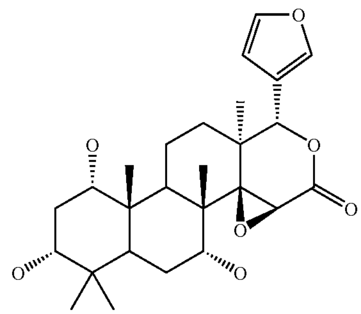 | 97 |
| 7beta-HYDROXY-7-DESACETOXYKHIVORINIC ACID, METHYL ESTER | 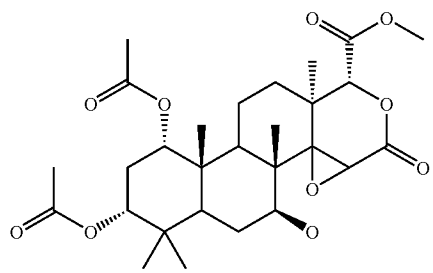 | 84 |
| 3beta-HYDROXYDEOXODIHYDROGEDUNIN | 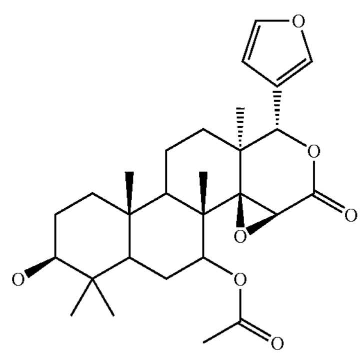 | 82 |
| DEOXODEOXYDIHYDROGEDUNIN | 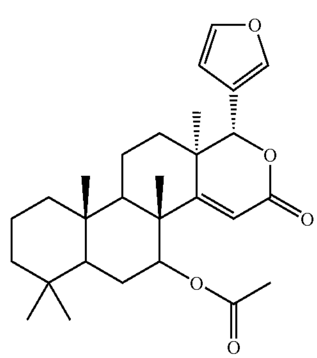 | 77 |

TABLE 5-continued

Modified Terpenoids having Significant 3-NP Neuroprotective Activity

| Compound | Structure | % Protection |
| --- | --- | --- |
| KHIVORIN | 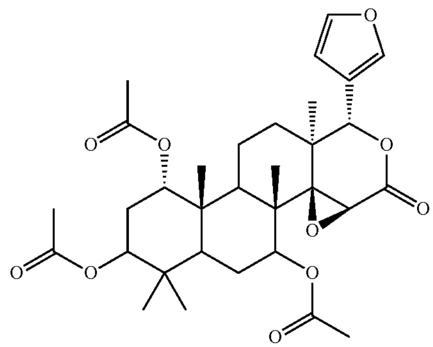 | 70 |
| EPOXYGEDUNIN | 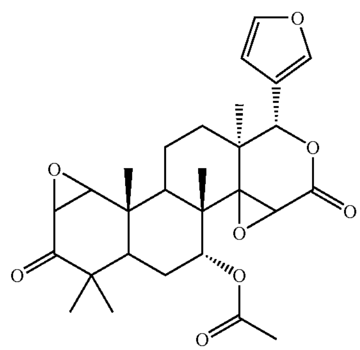 | 69 |
| 7-EPIKHIVORIN | 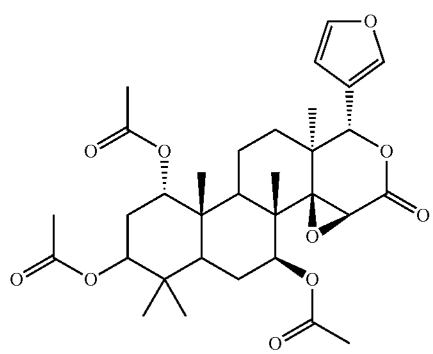 | 65 |
| 3beta, 7-beta-DIACETOXYDEOXODEACETOXY-DEOXYDIHYDROGEDUNIN | 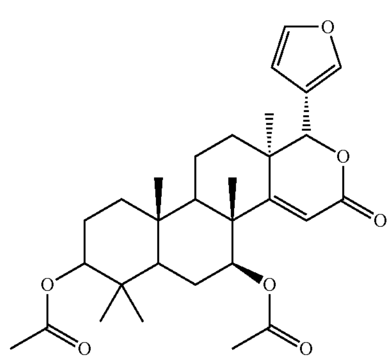 | 61 |

TABLE 5-continued

Modified Terpenoids having Significant 3-NP Neuroprotective Activity

| Compound | Structure | % Protection |
|---|---|---|
| DESACETYL (7)KHIVORINIC ACID, METHYL ESTER | 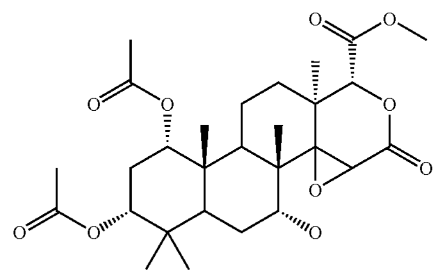 | 58 |
| 3-DEOXO-3beta-ACETOXYDEOXY-DIHYDROGEDUNIN | 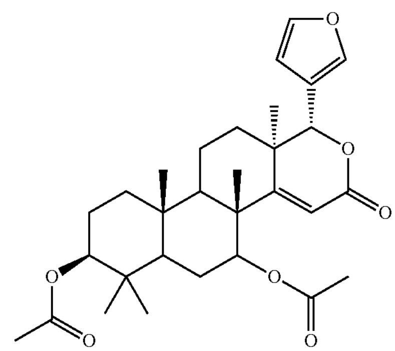 | 56 |
| 3beta-HYDROXYDEOXODIHYDRODEOXY-GEDUNIN | 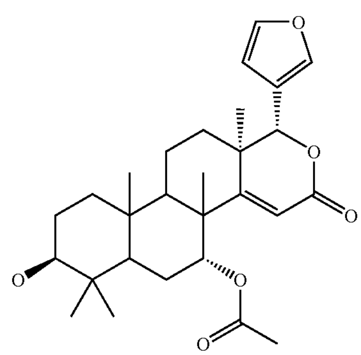 | 56 |
| DEOXYGEDUNOL ACETATE | 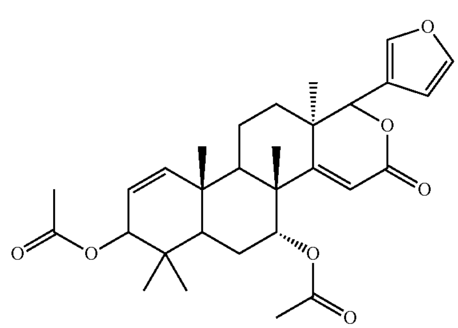 | 54 |

TABLE 5-continued
Modified Terpenoids having Significant 3-NP Neuroprotective Activity
| Compound | Structure | % Protection |
|---|---|---|
| ISOGEDUNIN | 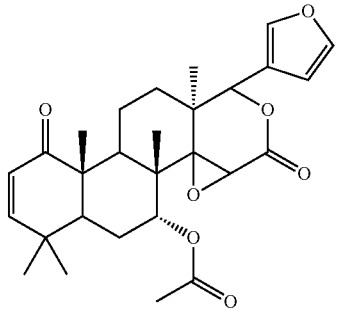 | 50 |
| GEDUNOL | 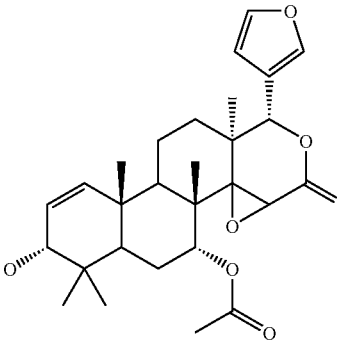 | 45 |
| 2,3-DIHYDROISOGEDUNIN | 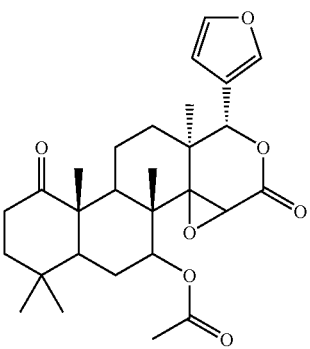 | 44 |
| 7-DEACETOXY-7-OXO-KHIVORINIC ACID, METHYL ESTER | 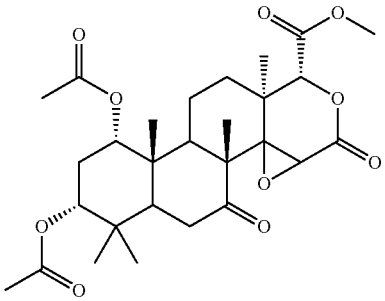 | 42 |

TABLE 5-continued

Modified Terpenoids having Significant 3-NP Neuroprotective Activity

| Compound | Structure | % Protection |
|---|---|---|
| TRIDESACETOXYKHIVORIN | 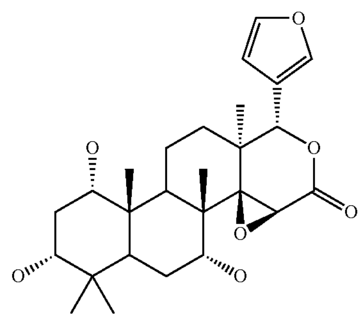 | 39 |
| 3beta-ACETOXYDEOXODIHYDRO-GEDUNIN | 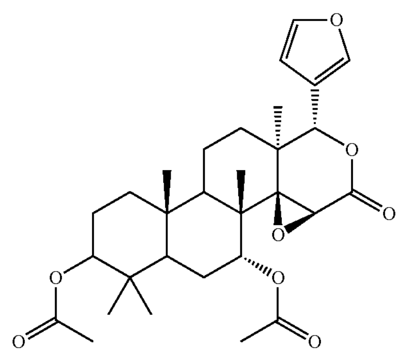 | 39 |
| DEACETOXY-7-OXOGEDUNIN | 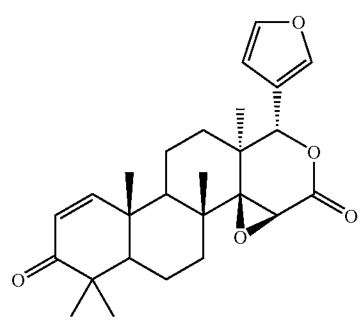 | 38 |
| DEOXYKHIVORN | 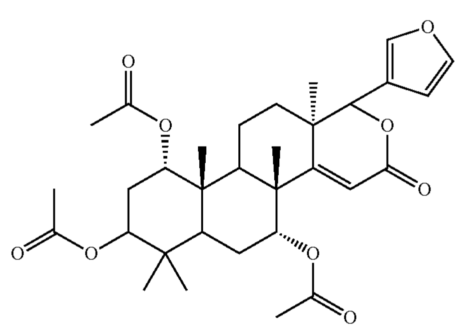 | 36 |

TABLE 5-continued

Modified Terpenoids having Significant 3-NP Neuroprotective Activity

| Compound | Structure | % Protection |
|---|---|---|
| 7-DEACETOXY-7-OXOKHIVORIN | 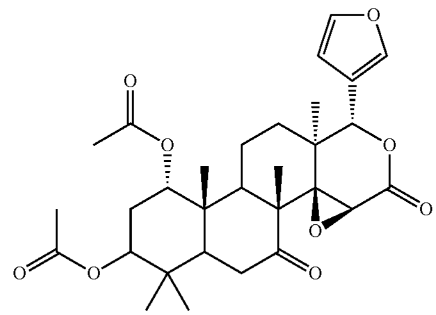 | 36 |
| 3alpha-HYDROXY-3-DEOXYANGOLENSIC ACID METHYL ESTER | 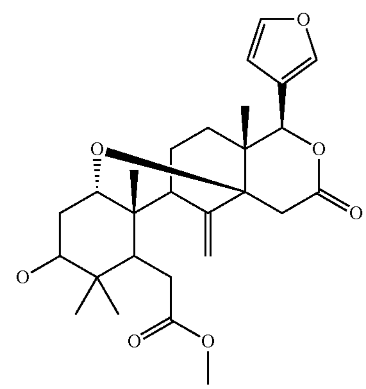 | 35 |
| ANGOLENSIC ACID, METHYL ESTER | 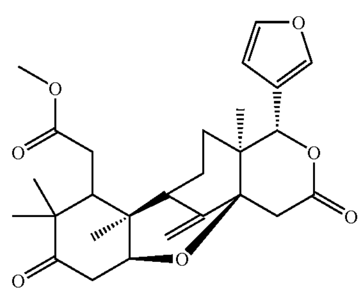 | 33 |
| 7-DEACETYLKHIVORIN | 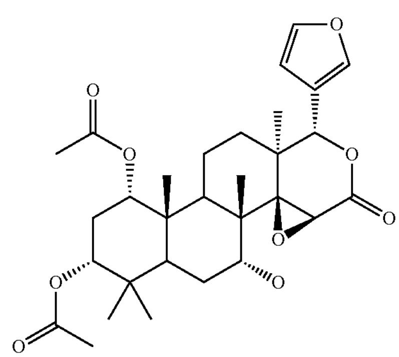 | 32 |

TABLE 5-continued

Modified Terpenoids having Significant 3-NP Neuroprotective Activity

| Compound | Structure | % Protection |
|---|---|---|
| 3beta-HYDROXYDEOXYDESACETOXY-7-OXOGEDUNIN | 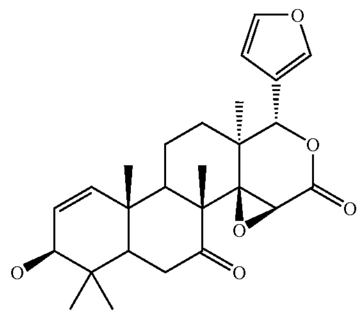 | 30 |
| 3-alpa-HYDROXYDEOXYGEDUNIN | 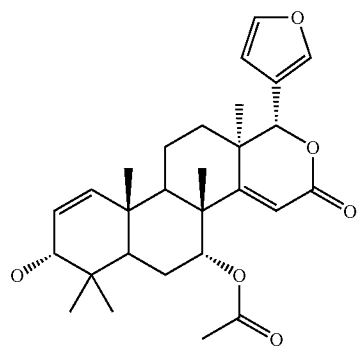 | 28 |
| DIHYDROGEDUNIN | 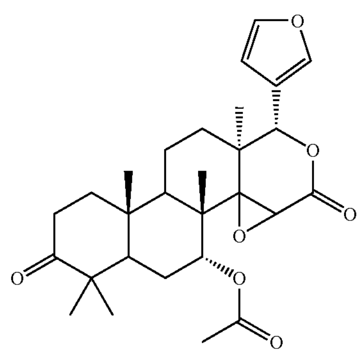 | 28 |
| 6-HYDROXYANGOLENSIC ACID METHYL ESTER | 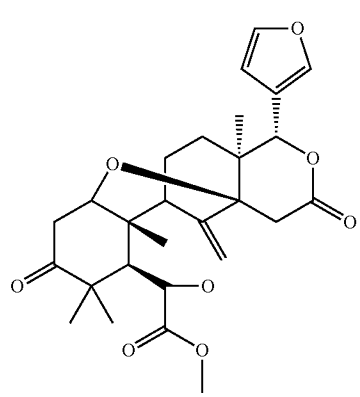 | 26 |

TABLE 5-continued
Modified Terpenoids having Significant 3-NP Neuroprotective Activity
| Compound | Structure | % Protection |
|---|---|---|
| 1,2alpha-EPOXYDEACETOXYDIHYDRO-GEDUNIN | 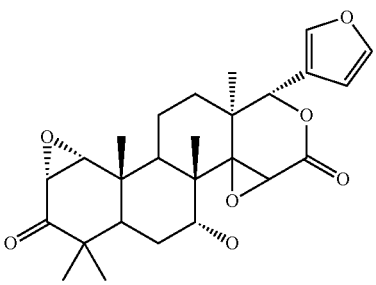 | 25 |
| 7-DEACETOXY-7-OXODEOXYGEDUNIN | 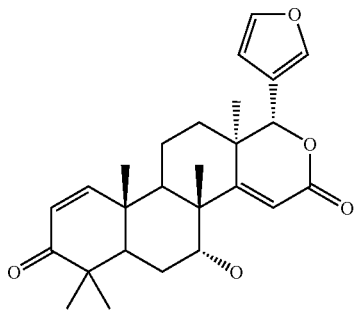 | 24 |
| DEOXYGEDUNIN | 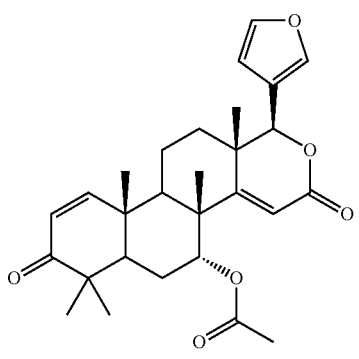 | 23 |
| GEDUNIN | 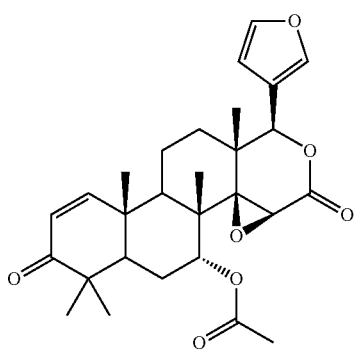 | 40 |

TABLE 5-continued
Modified Terpenoids having Significant 3-NP Neuroprotective Activity
| Compound | Structure | % Protection |
|---|---|---|
| DEACETYLGEDUNIN | 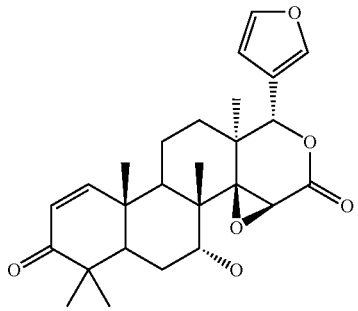 | 19 |
| DIHYDROGEDUNIN ETHANEDITHIOKETAL | 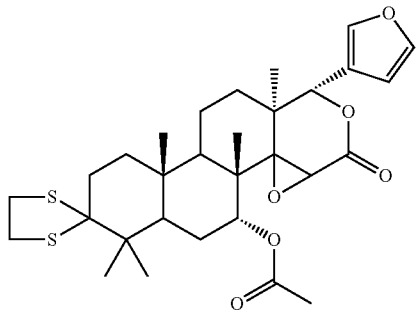 | 19 |
| 1,7-DIDEACETOXY-1,7-DIOXO-3-DEACETYLKHIVORIN | 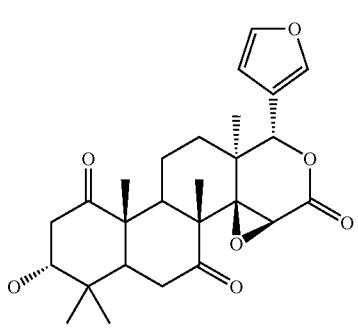 | 15 |
| 1,3-DIDEACETYL-7-DEACETOXY-7-OXOKHIVORIN | 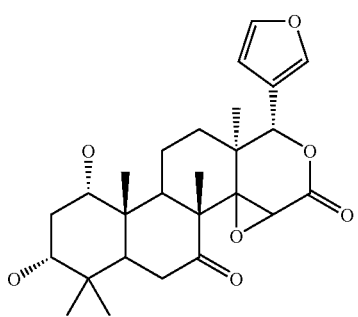 | 15 |

TABLE 5-continued

Modified Terpenoids having Significant 3-NP Neuroprotective Activity

| Compound | Structure | % Protection |
|---|---|---|
| 1 (2)alpha-EPOXYDEOXYDIHYDROGEDUNIN | 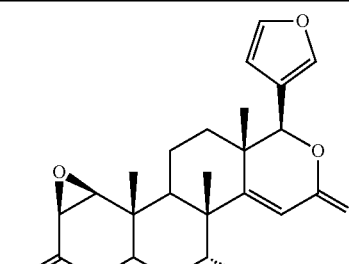 | 14 |

Details of the neuroprotective properties of the foregoing antifungal compounds can be found in U.S. patent application Ser. No. 11/893,100 filed on Aug. 13, 2007. In some embodiments, the neuroprotective agent is a neuroprotective antifungal compound, e.g., econazole nitrate, tolnaftate, miconazole nitrate, flutrimazole, flucanazole, or any other antifungal compound listed in Table 6.

TABLE 6

Antifungal Compounds having Significant 3-NP Neuroprotective Activity

| Compounds | % Protection vs 3NP |
|---|---|
| KETOCONAZOLE | 20.93% |
| CLOTRIMAZOLE | 12.57% |
| EXALAMIDE | 9.19% |
| GRISEOFULVIN ANALOG B | 10.80% |
| FLUCONAZOLE | 13.35% |
| SULCONAZOLE NITRATE | 18.21% |
| GRISEOFULVIN ANALOG A | 22.47% |
| FLUTRIMAZOLE | 46.85% |
| TOLNAFTATE | 66.83% |
| ECONAZOLE NITRATE | 141.18% |
| TRIACETIN | 45.14% |
| MICONAZOLE NITRATE | 81.61% |
| RESVERATROL | 41.20% |
| RHAPONTIN | 22.12% |
| NYSTATIN | 46.72% |

Details of the neuroprotective properties of the foregoing antifungal compounds can be found in U.S. Provisional Patent Application Ser. No. 60/922,043 filed on Apr. 5, 2007. In Tables 5 and 6 "% Protection vs 3-NP" refers to the increase in cultured neuron viability in the presence of the oxidative stressor 3-nitropropionic acid. For details of the assay, see Example 3 below.

In some embodiments any of the foregoing compositions are used for the manufacture of a medicament for treating or reducing the risk of developing multiple sclerosis in a subject having a ratio of a cystatin C protein fragment lacking about 8 amino acids at its C terminus (e.g., SEQ ID NO:2) to full length cystatin C protein that is greater than a control ratio reference value.

Kits

Provided herein are kits for diagnosing MS, an early stage thereof, or a condition relating thereto, monitoring progression of the disease or assessing response to therapy. A kit may comprise an agent for detecting or measuring one biomarker or a combination of two or more biomarkers. For example, a kit may comprise a reagent that specifically binds to a molecule selected from the group consisting of the molecules set forth in Table 2 and Table 4.

In some embodiments, the kit comprises (i) an isolated antibody that binds specifically to a cystatin C protein fragment lacking about 8 amino acids at its C-terminus and does not bind significantly to a full-length cystatin C protein, and (ii) a reagent for detecting binding of the isolated antibody. In other embodiments, a kit includes (i) an isolated antibody that binds specifically to an epitope in the last 8 amino acids of the cystatin C protein C-terminus, and does not bind significantly to the full-length C-protein, and (ii) a reagent for detecting binding of the isolated antibody. In some embodiments, any of the foregoing kits may further comprise an antibody that specifically binds to full length cystatin C, but does not bind significantly to a cystatin C protein fragment lacking about 8 amino acids at its C-terminus. In some embodiments, any of the foregoing kits further comprises an isolated polypeptide comprising an amino acid sequence that is at least 95% identical to SEQ ID NO: 2, wherein the polypeptide does not comprise the last 8 C-terminal amino acids of cystatin C.

In developing such kits, validation studies (e.g., determining minimal sensitivity of a reagent) are typically performed for each biomarker and biomarker detection platform. For a given biomarker, this may be an immunoassay or mass spectroscopy assay. Kit development may require specific antibody development, evaluation of the influence (if any) of matrix constituent ("matrix effects"), and assay performance specifications. A kit may comprise a container for sample collected from a patient and a biomarker specific reagent.

The present description is further illustrated by the following examples, which should not be construed as limiting in any way. The contents of all cited references (including literature references, issued patents, published patent applications and GenBank Accession numbers as cited throughout this application) are hereby expressly incorporated by reference. When definitions of terms in documents that are incorporated by reference herein conflict with those used herein, the definitions used herein govern.

EXAMPLES

The following specific examples are to be construed as merely illustrative, and not limitative of the remainder of the disclosure in any way whatsoever.

Example 1

Cleavage of Cystatin C in the CSF of Patients with Multiple Sclerosis

The diagnosis of multiple sclerosis (MS) can be challenging due to the lack of a specific diagnostic test. Recent advances in proteomics, however, offer new opportunities for biomarker discovery and the study of disease pathogenesis. We analyzed CSF samples from 29 patients with MS or clinically isolated syndromes (CIS), 27 patients with transverse myelitis (TM), 50 patients with HIV infection and 27 patients with other neurological diseases (OND) by surface enhanced laser desorption/ionization (SELDI) time of flight-mass spectroscopy. We found a unique protein of 12.5 kD that was 100% specific for MS/CIS compared with TM or OND. Low levels of this protein were found in some patients with HIV infection. Tandem mass spectroscopy of a tryptic digest of this 12.5 kD protein identified it as a cleavage product of full-length cystatin C (13.4 kD), an important inhibitor of cysteine proteases including the cathepsins. While total cystatin C levels in the MS patients was not different compared to controls, the patients with the highest 12.5/13.4 peak ratios also had the greatest cathepsin B inhibitory activity. As described in further detail below, this suggests that cleavage of cystatin C may be an adaptive host response and may identify a subgroup of patients with MS.

The accurate identification of patients with multiple sclerosis (MS) can be challenging at the time of disease onset. Even with magnetic resonance imaging (MRI), evoked potentials and cerebrospinal (CSF) studies, the diagnosis is still based on clinical criteria. While reliable serological tests are available for most autoimmune diseases, no such assay is available for the diagnosis of MS in part because no single antigen has been specifically associated with the disease. Nevertheless, the availability of effective immunomodulatory therapy makes it important to identify biological biomarkers that reliably distinguish MS from other neurological diseases.

The recent development of a protein chip platform based on surface enhanced laser desorption/ionization (SELDI) time of flight mass spectroscopy allows for the high throughput analysis of complex protein mixtures. This method requires microliter amounts of sample and has a sensitivity in the sub femtomole range. Using this technique, specific biomarkers for some types of cancer have been reported (1). However, tumors are cell-type specific and usually follow a predictable clinical course, hence biomarker discovery using cell extracts, serum or other body fluids has progressed rapidly in this field. In contrast, multiple immune cells, neuroglia and neurons have complex interactions with one another in MS and these interactions can vary over time. Thus, the clinical course of MS is both variable and unpredictable and biomarker discovery for this disease poses unique challenges. In a recent attempt to identify disease specific biomarkers for MS, CSF from five patients was analyzed by two dimensional gel electrophoresis. Despite the small sample size, 15 proteins were found to be differentially expressed in the CSF of MS patients compared to controls (2). In the present study, we analyzed CSF samples by SELDI time of flight mass spectroscopy from a larger sample size of well-characterized patients and controls. Analysis of CSF has several advantages over serum for biomarker discovery in neurological disease. CSF better represents local events in the brain as compared to serum. Further, high abundance proteins in serum may mask the low abundant, low molecular weight proteins that are the likely candidates for biomarkers. We identified several proteins that were significantly dysregulated in patients with MS or CIS, one of which was a cleavage product of cystatin C. Our findings have important implications for the diagnosis of MS and for understanding disease pathogenesis.

Patient Selection

All CSF samples used in these studies were obtained from patients undergoing a lumbar puncture as part of their diagnostic evaluation being conducted through the Adult Neurology Clinic at The Johns Hopkins Hospital. A protocol approved by our Institutional Review Board for Human Subjects Research allowed us to collect a small additional sample along with each diagnostic specimen. Written informed consent was obtained from each patient before these samples were obtained. Individuals with definite MS (n=23) were diagnosed according to current criteria (3, 4). Six patients had clinically isolated syndromes (CIS) and abnormal cranial MRI scans consistent with MS (4). Four of these patients have since had second clinical attacks and thus have confirmed MS. CSF samples from patients with various other neurological disorders (OND) (n=27) were used as controls. A diagnosis in each of these patients was defined according to individual disease criteria. These samples represented both inflammatory (n=12) (n=3 each with neurosarcoidosis and viral meningoencephalitis, n=1 each with acute inflammatory demyelinating neuropathy, chronic inflammatory demyelinating neuropathy, primary central nervous system (CNS) lymphoma, HIV infection with progressive multifocal leukoencephlopathy, lumbosacral plexitis and CNS Lyme's disease) and non-inflammatory neurological diseases (n=15) (n=3 each with normal pressure hydrocephalus and amyotrophic lateral sclerosis, n=2 with pesudotumor cerebri, and n=1 each with meningioma, drugs induced delirium, spinocerebellar degeneration, Alzheimer's disease, hereditary myelopathy and Parkinson's disease). For the purpose of this study, CSF was considered inflammatory in the control samples if one or more of the following abnormalities were present: white cell count >5 cells/mm3, detectable oligoclonal bands or IgG index >0.8. CSF samples from another 27 patients with acute transverse myelitis (TM) and 50 patients with HIV infection (22 without dementia and 28 with dementia) were used as other controls. All patients except three with TM had an inflammatory CSF but none had oligoclonal bands or an elevated IgG index. Samples from HIV infected patients were taken from the prospectively followed North Eastern AIDS dementia cohort (5). None of the patients had opportunistic infections.

Demographic and clinical data on the patients with MS/CIS was obtained by direct patient interview or from the relevant medical records (Table 1 provided online). With the exception of two patients with secondary progressive MS who were already on disease modifying therapy, none of our patients had received any treatment other than corticosteroids before the time of CSF acquisition. An Expanded Disability Status Scale (EDSS) score was obtained at the time of CSF acquisition by an examiner who was blinded to the results of our analyses. Each patient also had an enhanced cranial MRI scan within 2 weeks of their lumbar puncture. The total number of T2 hyperintense lesions, T1 hypointense lesions, and gadolinium-enhancing T1 lesions meeting a >3 mm size cut-off criteria was determined from each scan by a single blinded examiner. Each scan was also judged as to whether it met the formal requirements for an abnormality consistent with MS according to published criteria (3,4).

Protein Chip Assay

All CSF samples were handled equally and placed immediately on ice and centrifuged at 3000 rpm for 10 min. The cell free samples were then stored at −80° C. in 0.5 ml aliquots. For protein chip analysis, a single aliquot of CSF was thawed and immediately realiquoted into 50 μl volumes and refrozen at −80° C. Each sample was thawed once more before analysis. CSF samples were initially analyzed using the weak cation exchange (CM10) and the hydrophobic chip (H50) protein chips (Ciphergen Biosystems, Freemont, Calif.). These chips bound proteins with specific physio-chemical properties, which were then resolved by SELDI time of flight mass spectroscopy (Ciphergen Biosystems, Freemont Calif.). Spectra derived from CM10 chips showed a greater number of peaks and a better resolution of low molecular mass species and were used in all subsequent assays. The protein chip arrays were assembled into a deep well type Bioprocessor assembly (Ciphergen Biosystems). Prior to sample loading, the arrays were equilibrated with 150 μl of binding buffer (50 mM ammonium acetate buffer, pH=4.0). Each spot on the array was then incubated with 15 μl of CSF diluted in binding buffer to a final volume of 150 μl with gentle agitation for one hour at room temperature. The spots were washed in the same buffer three times, after which 1 μl of 50% saturated sinapinic acid (SPA) dissolved in 50% acetonitrile, 0.5% trifluoroacetic acid solution was added. The chips were air-dried and SPA reapplied. The protein chips were analyzed in the ProteinChip® biology systems reader (model PBSIIc, Ciphergen Biosystems) using a laser intensity of 2.6 microJoules and a sensitivity setting of 5. Resulting spectra were noise filtered, baseline substracted, and calibrated with Ciphergen's "All-in-One Protein standard" consisting of cytochrome C (12, 360.2 Daltons), myoglobin (16,951.5 Daltons), and GAPDH (35,688 Daltons). Biochemical properties of the unique peaks identified in CSF samples were further characterized by changing the pH of the binding buffer (range 4.0-9.0). The stability of these peaks was also determined by monitoring the effects of freeze/thaw cycles on the CSF, heating of samples to 50° C. for 30 min or leaving them at room temperature for 16 hrs. Each sample was analyzed in duplicate. All peaks obtained through the peak detection process were aligned using the Biomarker Wizard tool in the Ciphergen ProteinChip software (version 3.1). Peaks of similar (0.3%) mass/charge (m/z) ratio were clustered across all spectra. Each cluster then represented a particular protein.

Data Analysis:

All data were internally normalized by total ion current. Spectra used for further analysis had normalization factors <2 standard deviations from the mean. The comparison of peak intensities and the ratios of the 12.5 kD and 13.4 kD peak amongst the patient groups was done by a one way ANOVA using a Tukey Kramer comparison test. Linear regression curves were generated using Graph Pad Prizm™ to determine if there was a correlation between cystatin C levels and cathepsin B activity.

Enrichment of 12.5 kD protein

A single CSF sample (MS267) that had a prominent 12.5 kD peak was selected for further study. One ml of CSF was semi-purified in 100 μl aliquots. 100 μl CSF was incubated with 50 μl of equilibrated protein A beads for 5 min at room temperature to remove IgG. The supernatant was collected and diluted 1:5 with 50 mM Tris, pH=9.0. Ten μl of Q Hyper D strong anion exchange beads (Ciphergen) equilibrated with 50 mM Tris pH=9.0 was incubated with each sample aliquot for 5 min at room temperature. The supernatant was collected and dialyzed in 4 changes of 1 L ultrapure water overnight. Purification of the 12.5 kD peak was confirmed by SELDI time of flight mass spectrometry.

Tris-Tricine Gel Electrophoresis:

All 10 aliquots processed in a manner described above were combined, lyophilized and resuspended in 45 ul ultra-pure water to which 45 μl of Tricine sample buffer (Biorad, Hercules, Calif.) with 2% β-mercaptoethanol was added. Proteins were resolved using precast 16.5% Tris-Tricine SDS-PAGE gels (BioRad, Hercules, Calif.). The anode buffer consisted of 0.2 M Tris-HCl, pH 8.9, and the cathode buffer consisted of 0.1 M Tris-HCl, 0.1 M Tricine, 0.1% SDS, pH 8.3. Samples were diluted in 10 mL of 50 mM Tris-HCl, 4% w/v SDS, 12% w/v sucrose, 5% v/v β-mercaptoethanol, and a trace of bromophenol blue, pH 6.8. After denaturation at 97° C. for 5 min, samples were loaded onto the gel with 30 μl/lane. Gels were run at 200 mamps for 3 hr. After electrophoresis, gels were fixed, stained with a Silver Stain Plus Kit (Biorad, Hercules, Calif.), and dried between 2 pieces of cellophane.

Protein Digestion and Peptide Extraction

The 12.5 kD band was excised following silver staining of the gel. Tryptic digestion and peptide extraction were performed on the excised band (6). The gel band was destained in 15 mM potassium ferricyanide/50 mM sodium thiosulfate followed by washing with water and dehydration with acetonitrile. The isolated gel band was then incubated for 45 min at 55° C. with 10 mM dithithreitol followed by incubation with 55 mM iodoacetamide for 30 min at room temperature. The sample was then washed and dehydrated with alternating washes of 5 mM ammonium bicarbonate followed by acentonitrile. After drying the extract in a speedvac for 15 min, tryptic digestion was performed with 12.5 μg/ml trypsin in 5 mM ammonium bicarbonate overnight at 37° C. Peptides were extracted with successive incubations of 25 mM ammonium bicarbonate, followed by 5% formic acid and then acetonitrile. Samples were dried, cleaned and concentrated using an OMIX C18 pipette tip according to manufacturer's instructions (Varian, Palo Alto, Calif.).

Protein Identification by Tandem Mass Spectrometry

An Axima CFR MALDI-TOF mass spectrometer (Kratos, Manchester, UK) was used for protein identification and accurate mass measurements. 2 μl of the cleaned peptides along with 125 fmol of a three-point calibrant mixture were spotted via the dried droplet method with 0.3 μl saturated α-Cyano-4-hydroxycinnamic acid (CHCA) (Sigma, St. Louis, Mo.) in 50% ethanol/50% ddH2O. Internal calibration was applied and the monoisotopic masses of the tryptic digest peaks were acquired. Tandem mass spectrometry (MS/MS) was performed on selected peaks. The monoisotopic masses of the tryptic digest peaks were combined with fragment data from the MS/MS into a single Mascot (matrixscience.com) search. To obtain an accurate mass of the peaks 12.5 kDa and 13.4 kDa, a CSF sample containing these peaks was processed as described above on a CM-10 chip. Prior to the addition of matrix, a three-point mass calibrant mixture was added directly to the sample spot to allow for internal calibration. Using a modified holder (with permission of Ciphergen Biosystems, Inc.) these chips were then analyzed for accurate mass using an Axima CFR MALDI-TOF mass spectrometer.

Immunodepletion of Cystatin C

20 μl of rabbit anti-human cystatin C or rabbit anti-fusin antisera (DakoCytomation, Carpinteria, Calif.) was bound to 10 μl of protein A beads equilibrated in PBS, pH 7.4, by rocking at room temperature for 1 hr. 10 μl of equilibrated protein A beads alone were used as another control. Each sample was washed three times with PBS pH=7.4. A CSF sample was selected that contained both the 13.4 kD and the 12.5 kD peaks. 30 µl of this CSF was added to each of the above sample and rocked for 1 hr at room temperature. 15 µl of the supernatant was applied to CM-10 arrays and analyzed as described above.

Cystatin C Levels

A sandwich ELISA was used to measure cystatin C levels in the CSF samples according to the manufacturers instructions (Alexis Biochemicals, San Diego, Calif.). Each CSF sample and standard was analyzed in duplicate. Concentration of cystatin C in each CSF sample was determined using a standard curve and expressed as relative fluorescence units.

Cathepsin B Activity

The activity of cathepsin B, a substrate of cystatin C, was measured using an activity assay kit (Biovision Research Products, Mountain View, Calif.). This fluorescence-based assay utilizes the cathepsin-B substrate sequence Arg-Arg labeled with amino-4-trifluoromethyl coumarin (AFP). Cathepsin-B cleaves the synthetic substrate RR-AFC to release free AFC. THP-1 cells (a monocytic cell line) were used as a source of cathepsin B. Cell lysates were prepared using a lysis buffer provided with the assay kit. Cell lysates from $1 \times 10^6$ cells were added to 50 µl of CSF in a microtiter plate (q.s. 100 µl). Two µl of substrate Ac-Arg-Arg-AFC was added to each well and incubated for 1 hr at 37° C. Absorbance was measured using a fluorescent plate reader with a 400 nm excitation filter and 505 nm emission filter. Controls included reaction buffer alone and a cathepsin B inhibitor provided in the kit. All samples were analyzed in duplicate.

Figure 2:
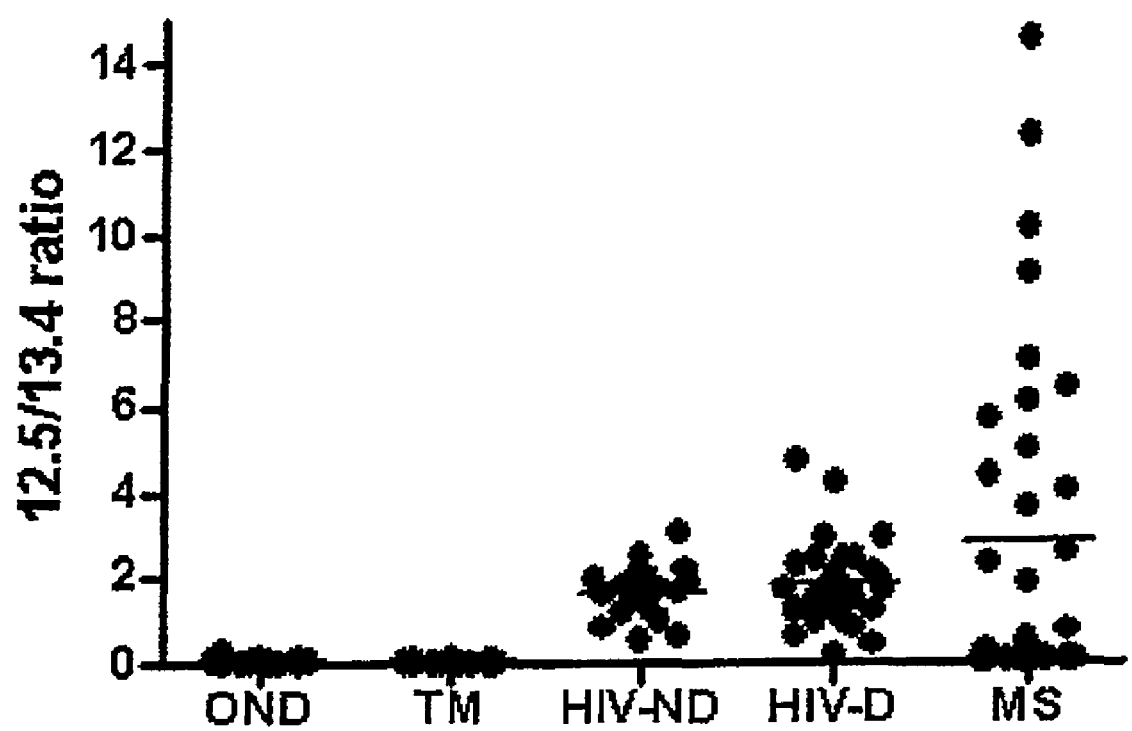
FIG. 2 shows a comparison of the ratio of the 12.5 kD to 13.4 kD peak in CSF from different disease states. The 12.5/13.4 peak ratio was significantly elevated in the MS group compared to OND (P<0.001), TM (P<0.001) HIV-ND (P<0.05) and HIV-D (P<0.05).

A total of 217 peaks with a signal to noise ratio of 5:1 in the mass range of 3-100 kD were identified in the CSF samples. SELDI mass spectra for 12,000 to 13,500 m/z range from a representative control and MS patient is shown in FIG. 1. Replicate samples were averaged and then analyzed by a Mann Whitney U test, using a P value cut off of 0.01. We found two peaks that were significantly elevated and another two peaks that were significantly diminished in the MS/CIS samples (Table 2; FIG. 11). Interestingly, two of these peaks appeared to have a reciprocal arrangement, such that all MS/CIS patients in whom the 12.5 kD peak was elevated, the 13.4 peak was diminished. The 13.6 kD peak was a broad peak and may represent a complex mixture of proteins. A peak at 3.9 kD (Table 2, FIG. 11) was also significantly elevated in the patients with MS/CIS, however the peak height was small and had only a two-fold increase in the MS/CIS patients compared to controls. Hence we have not pursued the identity of these proteins at this point. The 12.5 kD peak was present in 19/29 MS/CIS patients and in none of the patients with OND or TM. Its presence alone provided 100% specificity but only 66% sensitivity for diagnosis of MS when compared to these diseases. The 12.5 kD peak was found in some patients with HIV infection, the levels were small and significantly lower when compared to the MS/CIS patients. Due to a reciprocal relationship between the 12.5 and 13.4 kD peaks, we calculated a ratio of the 12.5 kD to 13.4 kD peak for comparison purposes. The ratios of the two peaks were significantly elevated in the MS/CIS group (mean±SE=4.632±0.909) compared to OND (mean±SE=0.109±0.011; P<0.001), TM patients (mean±SE=0.068±0.006; P<0.001), HIV ND (mean±SE=1.646±0.124; P<0.05) and HIVD (mean±SE=1.815±0.187; P<0.05) (FIG. 2). To examine the stability of this protein in CSF we reanalyzed three samples after leaving them at room temperature for four hours and overnight. We found that the 12.5 kD peak was stable with no change in CSF stored at room temperature for up to four hours and only a slight increase following overnight storage of CSF at room temperature. The peak was also not affected by heat treatment.

Figure 3:
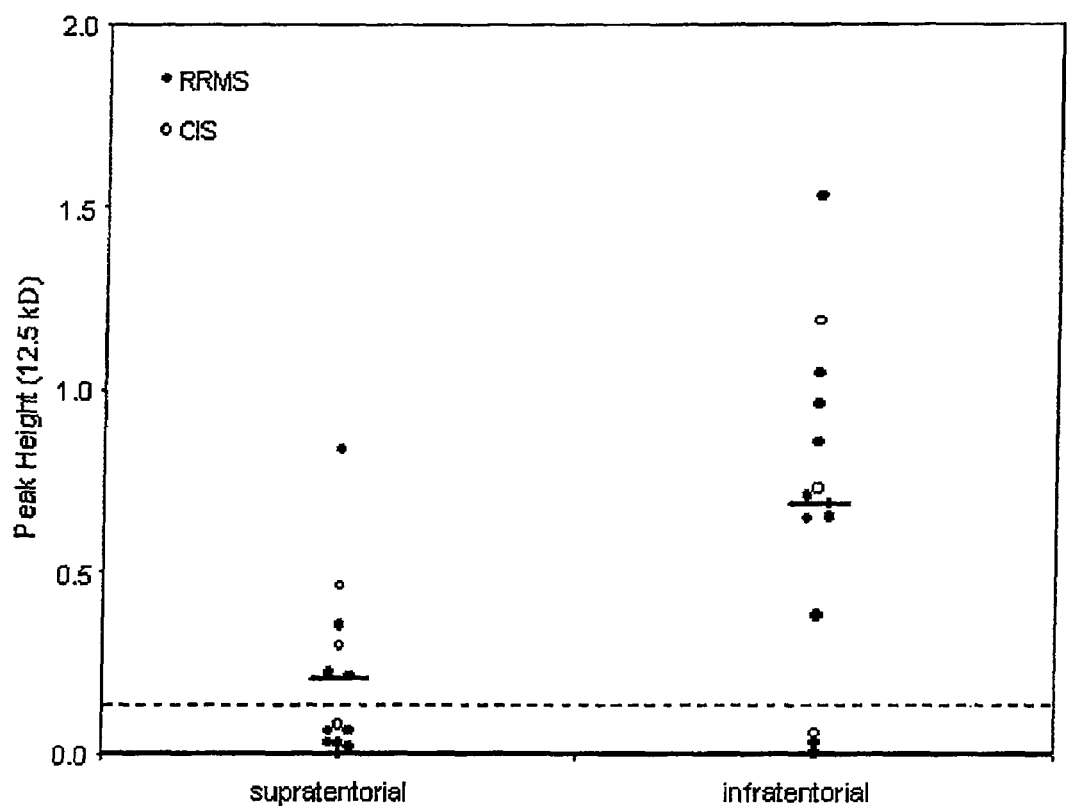
FIG. 3 shows an effect of anatomical location of last clinical attack on 12.5 kD peak height in CSF of MS/CIS patients. The peak was significantly higher in patients with recent infratentorial disease activity compared to those with a supratentorial involvement (P<0.05).

Despite the small samples sizes, we analyzed our data to determine if there was a correlation between the intensity of the 12.5 kD peak and the clinical pattern of MS (CIS, remitting relapsing, secondary progressive), measures of disease activity (duration since last attack, total lesion burden or contrast enhancement on MRI) or effect of treatment (Table 1; FIG. 10). Although no correlation could be found with any of these parameters, there were significantly higher levels in those patients whose last attack involved infratentorial regions (brain stem, cerebellum and spinal cord) when compared to those individuals whose last attack involved supratentorial regions (P=0.02) (FIG. 3). Interestingly, however, CSF from patients with acute transverse myelitis showed a prominent 13.4 kD peak in all samples, while the 12.5 kD peak was not visualized in any of them.

Figure 4:
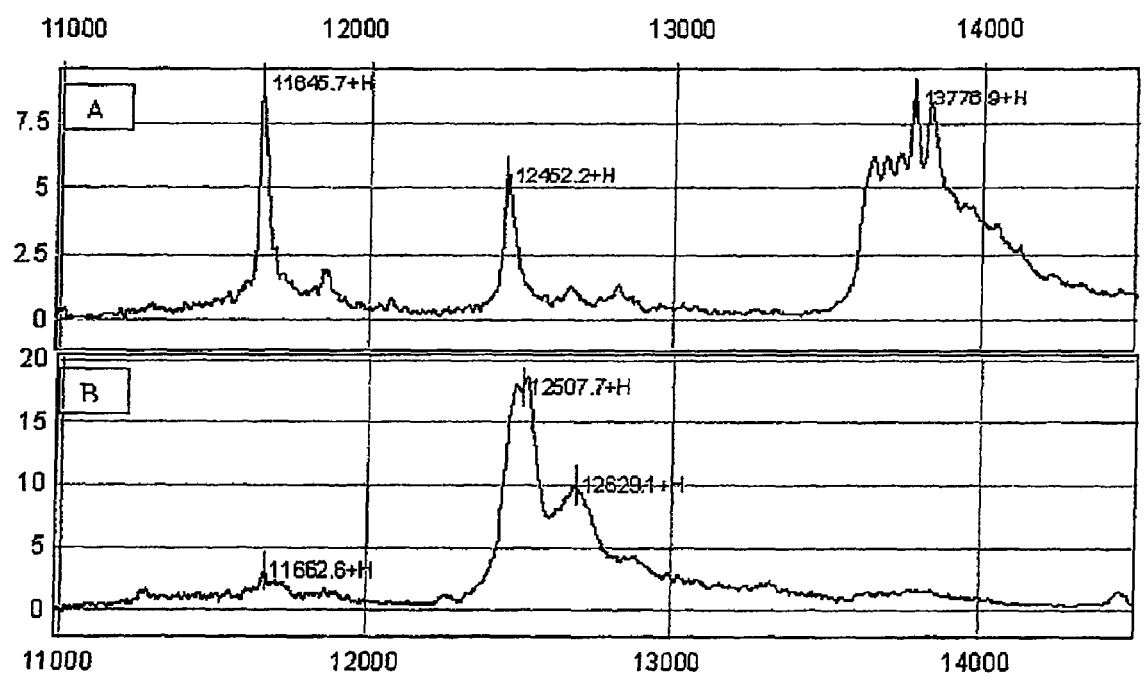
FIG. 4 shows a partial purification of the 12.5 kD protein from CSF. (A) CSF incubated with protein A beads to remove IgG and then analyzed by SELDI time of flight mass spectroscopy shows the presence of the 12.5 kD protein. (B) CSF was further exposed to strong anion exchange beads and reanalyzed by SELDI time of flight mass spectroscopy which shows the removal of the 11.6 kD and 13.8 kD complexes and relative enrichment of the 12.5 kD protein.

To identify the protein corresponding to the 12.5 kD peak, we studied its binding properties to CM-10 chips at different pH. We found that the overall binding properties of the 12.5 kD and 13.4 kD peaks were similar, as decreased binding with increasing pH was observed (data not shown). Although maximal binding was seen at pH=4.0, small amounts of this protein were still bound to the cation exchange chip even at pH 9.0 suggesting that the pI of this protein is >9.0. For purification purposes, we chose a CSF that showed high levels of the 12.5 kD protein. This sample was first run through a protein A column to remove IgG, followed by treatment using a strong anion exchange spin column. Proteins that passed through these columns were collected and analysis by the CM10 chip showed the 12.5 kD peak had been enriched (FIG. 4). This protein was then resolved by a tris-tricine gel and the corresponding band sequenced by MALDI MS/MS. Combining the monoisotopic masses of the tryptic peptides with the MS/MS fragment data yielded a Mascot score of 166 for human cystatin C (Accession #14278690) with 51% sequence coverage. The MS/MS data from two peptides (1226.68 Da, 2060.92 Da) yielded Mascot ion scores greater than 40 (Table 3). This combination of sequence and mass fingerprint information allowed for an unambiguous identification of human cystatin C. Intact MW measurements of the 12.5 kDa and 13.4 kDa peaks obtained via the Axima CFR were 12,538 Da and 13,361 Da respectively. The difference of 823 Da between the two peaks corresponds to the mass of the last eight amino acids at the carboxy terminal of cystatin C (accession#14278690), consistent with the conclusion that 12.5 kDa is a cleavage product of cystatin C.

Figure 5:
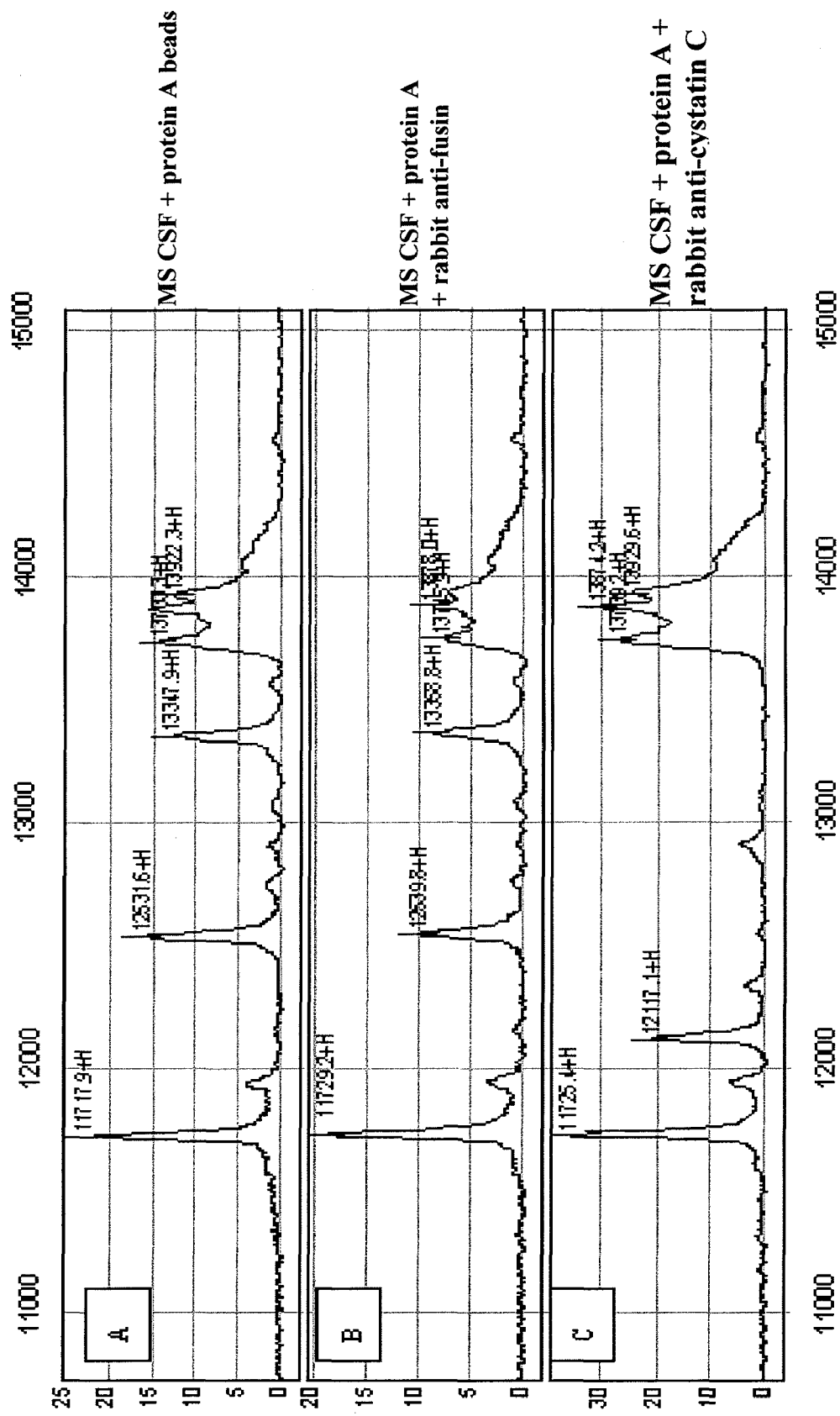
FIG. 5 shows immunodepletion of cystatin C from CSF. CSF was analyzed by SELDI time of flight mass spectroscopy following incubation with either (A) protein A beads alone, (B) protein A beads bound to rabbit anti-fusin antisera or (C) protein A beads bound to rabbit antisera to cystatin C. Both the 12.5 kD and the 13.4 kD proteins were selectively removed by the anti-cystatin antisera.

The identity of this 12.5 kD protein was further confirmed by immunodepletion from CSF samples using antisera to cystatin C followed by SELDI time of flight mass spectroscopy analysis. We chose CSF known to have both the 12.5 kD and 13.4 kD peaks. As shown in FIG. 5, exposure of the CSF to either protein A beads alone (FIG. 5A) or to protein A beads bound to rabbit anti-fusin antisera used as a control antisera to an irrelevant antigen (FIG. 5 B) had no effect on the detection of these proteins. However, protein A beads bound to anti-cystatin C antisera (FIG. 5C) immunodepleted both the 12.5 kD and the 13.4 kD peaks confirming that both of them are cystatin C. A new peak at 12.1 kD was now seen likely represents a protein unmasked protein by the removal of cystatin C.

We next measured total cystatin C levels in the CSF of the patients with MS/CIS (mean±SEM=9.3±0.3 units) and compared it to that of patients with OND (11.1±0.4 units). No significant differences were found between the two groups.

Since cystatin C is a protease inhibitor that specifically blocks cathepsin B activity, we also measured cathepsin B activity in the CSF of patients with MS/CIS. A significant inverse correlation ($P<0.05$) between the cystatin C levels and cathepsin B activity was found suggesting that the cystatin C in the CSF of MS/CIS patients is bioactive (FIG. 6A). To determine if cleavage of cystatin C alters its ability to inhibit cathepsin B, we compared the 12.5/13.4 kD peak ratio with cathepsin B activity in the MS patients. MS patients with peak ratio>0.1 the cathepsin B levels were 486±68.8 units (mean±SEM) and in MS patients with peak ratio<0.1 the levels were 697±52.8 (mean±SEM; P value=0.06). Further analysis of the MS group that showed a 12.5/13.4 kD peak ratio of >0.1 shows that patients with the highest CSF 12.5/13.4 ratios also exhibited the greatest inhibition of cathepsin B activity (FIG. 6B) suggesting the possibility that cleavage at the C terminal region may actually enhance its inhibitory function.

Identification of biomarkers for MS is not only of diagnostic importance but such biomarkers could be used to predict future clinical events, and may also be used for monitoring the effect of treatment. We demonstrated that CSF samples are a reliable biological specimen for SELDI analysis in search for biomarkers of MS.

We used SELDI-time of flight mass spectrometry to identify several novel protein peaks in the CSF of patients with MS/CIS compared to other controls. We focused in the mass range of 3-30 kD and compared only those proteins that bound to the weak cation chip. We identified a unique peak at 12.5 kD in the CSF of patients with MS/CIS. The identity of the 12.5 kD protein was established as a cleavage product of cystatin C formed by the removal of the last 8 amino acids from the carboxy terminal of the protein. Since this 12.5 kD peak was found in two thirds of MS/CIS samples and not in any of the controls with OND or TM, this maybe a novel biomarker for MS and hence of diagnostic and pathogenic significance. Higher concentrations of this protein in patients with infratentorial lesions maybe due to the anatomical proximity of the lesions to the lumbar thecal sac from where the CSF was withdrawn or due to unique features of MS lesions at these sites. However, the absence of the peak in patients with transverse myelitis may suggest that the pathophysiology of the lesions in the spinal cord of patients with TM and MS may be different. A previous study that included CSF samples from normal controls did not identify a 12.5 kD peak (7).

Several lines of evidence suggested that the 12.5 kD peak is a breakdown product of the 13.4 kD peak. The intensity of the 12.5 kD peak and that of the 13.4 kD peak seem to be reciprocally related to each other and the sequence analysis of the 12.5 kD peak revealed that it corresponds to cystatin C, which is has a molecular mass of 13.4 kD (7). Heating the CSF had no effect on the levels of the 12.5 kD and 13.4 kD peaks, while repeated freeze thaw cycles and overnight storage of CSF at room temperature resulted in a slight increase in the 12.5 peak intensity which suggests that heat treatment may denature the protease that cleaves the 13.4 kD protein into the 12.5 kD form (the 12.5 kDa peak resulting from the freeze/thaw is a different species than the peak in CSF of MS patients). These observations have important implications for future studies for biomarker discovery efforts in MS that will require the use of prospectively collected samples with strict adherence to uniform protocols for the collection, centrifugation and storage of CSF samples.

Cystatin C is an inhibitor of cysteine proteases including cathepsins B, H, K, L and S (8). It is present in high concentrations in CSF compared to serum and other body fluids (9). The protein is a non-glycosylated molecule of 120 amino acids formed after removal of a 26 amino acid signal peptide (10). Thus any altered activity or levels of cystatin C would also result in dysregulation of cathepsin function which have been implicated in a variety of effects including degranulation of cytotoxic lymphocytes (11) and in processing of MHC class II antigen in monocytes (12). A previous study that measured cystatin C levels in CSF of MS patients by ELISA also found diminished levels in patients compared to healthy controls. Conversely, levels of cathepsin B were increased in CSF and brain of patients with MS (13, 14). In contrast, while we did not have access to totally normal CSF, our studies did not show any significant difference between the cystatin C levels in the MS patients compared to patients with OND. Interestingly, other studies have shown that cystatin C levels are increased in the CSF of patients with Alzheimer's disease (7) and Creutzfeldt-Jacob disease (15). In both these studies, CSF was analyzed by SELDI and the 13.4 kD protein was further sequenced to identify it as cystatin C. In Icelandic patients with a hereditary form of amyloid angiopathy a mutated form of cystatin C (Leu68Gln substitution) has been found. This protein accumulates in the amyloid deposits and is truncated by 10 amino acids at the amino terminal (16). This region is critical for the functional activity of cystatin C (10). Leukocyte elastase has been shown to cleave cystatin C at Val10-Gly11 resulting in loss of its ability to bind to cathepsins (17). In our experiments, one of the peptides from the tryptic digest of the 12.5 kD protein that matched to cystatin C contained an intact Leu9-Val10-Gly11 and an intact amino terminal region suggesting the presence of a novel cleavage site at the carboxy terminal in the MS patients. The mass differences between the 12.5 kD and 13.4 kD proteins suggested that the cleavage site is at eight amino acids from the carboxy terminal end of the protein.

The role of cystatin C in the pathogenesis of MS is not understood. Elevated serum cystatin C levels have recently been shown to be a strong predictor of death in patients with cardiovascular disease (18). We did not find any significant difference in the total cystatin levels in the MS/CIS patients compared to controls. Our data suggested that the total levels of cystatin C are inversely proportional to cathepsin B activity. Furthermore it appears that cleavage of cystatin C did not lead to any augmentation of cathepsin B activity. In fact, the patients with the highest 12.5/13.4 ratios seemed to have the highest cathepsin B inhibition activity as well. This raised the possibility that cleavage of cystatin C at the carboxy terminus may lead to enhanced activity of this protein. This is in keeping with previous studies where the protease inhibiting effects of the molecule have been ascribed to the amino terminal region of the molecule (10). Cleavage of the carboxy terminus of cystatin C may thus be an adaptive host response in MS.

Based on these data, we concluded that measurement of levels of cystatin C and its breakdown product in the CSF of MS patients may identify a subtype of MS.

REFERENCES

1. Petricoin E F, Liotta L A. SELDI-TOF-based serum proteomic pattern diagnostics for early detection of cancer. Curr Opin Biotechnol. 2004; 15:24-30
2. Dumont D, Noben J P, Raus J et al. Proteomic analysis of cerebrospinal fluid from multiple sclerosis patients. Proteomics. 2004; 4:2117-2124
3. McDonald W I, Compston A, Edan G et al. Recommended diagnostic criteria for multiple sclerosis: guidelines from the International Panel on the diagnosis of multiple sclerosis. Ann Neurol. 2001; 50:121-127

4. Frohman E M, Goodin D S, Calabresi P A et al. The utility of MRI in suspected MS: report of the Therapeutics and Technology Assessment Subcommittee of the American Academy of Neurology. Neurology. 2003; 61:602-611
5. Sacktor N, McDermott M P, Marder K et al. HIV-associated cognitive impairment before and after the advent of combination therapy. J. Neurovirol. 2002; 8:136-142
6. Shevchenko A, Wilm M, Vorm O, Mann M. Mass spectrometric sequencing of proteins silver-stained polyacrylamide gels. Anal Chem. 1996; 68:850-858
7. Carrette O, Demalte I, Scherl A et al. A panel of cerebrospinal fluid potential biomarkers for the diagnosis of Alzheimer's disease. Proteomics. 2003; 3:1486-1494
8. Grzonka Z, Jankowska E, Kasprzykowski F et al. Structural studies of cysteine proteases and their inhibitors. Acta Biochim Pol. 2001; 48:1-20
9. Lofberg H, Grubb A O. Quantitation of gamma-trace in human biological fluids: indications for production in the central nervous system. Scand J Clin Lab Invest. 1979; 39:619-626
10. Abrahamson M, Ritonja A, Brown M A et al. Identification of the probable inhibitory reactive sites of the cysteine proteinase inhibitors human cystatin C and chicken cystatin. J Biol. Chem. 1987; 262:9688-9694
11. Balaji K N, Schaschke N, Machleidt W et al. Surface cathepsin B protects cytotoxic lymphocytes from self-destruction after degranulation. J Exp Med. 2002; 196:493-503
12. Greiner A, Lautwein A, Overkleeft H S et al. Activity and subcellular distribution of cathepsins in primary human monocytes. J Leukoc Biol. 2003; 73:235-242
13. Nagai A, Terashima M, Harada T et al. Cathepsin B and H activities and cystatin C concentrations in cerebrospinal fluid from patients with leptomeningeal metastasis. Clin Chim Acta. 2003; 329:53-60
14. Bever C T, Jr., Garver D W. Increased cathepsin B activity in multiple sclerosis brain. J Neurol Sci. 1995; 131:71-73
15. Sanchez J C, Guillaume E, Lescuyer P et al. Cystatin C as a potential cerebrospinal fluid biomarker for the diagnosis of Creutzfeldt-Jakob disease. Proteomics. 2004; 4:2229-2233
16. Gerhartz B, Abrahamson M. Physico-chemical properties of the N-terminally truncated L68Q cystatin C found in amyloid deposits of brain haemorrhage patients. Biol. Chem. 2002; 383:301-305
17. Abrahamson M, Mason R W, Hansson H et al. Human cystatin C. role of the N-terminal segment in the inhibition of human cysteine proteinases and in its inactivation by leucocyte elastase. Biochem J. 1991; 273 (Pt 3):621-626
18. Shlipak M G, Sarnak M J, Katz R et al. Cystatin C and the risk of death and cardiovascular events among elderly persons. N Engl J. Med. 2005; 352:2049-2060
19. Johansson L, Grubb A, Abrahamson M et al. A peptidyl derivative structurally based on the inhibitory center of cystatin C inhibits bone resorption in vitro. Bone. 2000; 26:451-459
20. Barrett A J, Kembhavi A A, Brown M A et al. L-trans-Epoxysuccinyl-leucylamido(4-guanidino)butane (E-64) and its analogues as inhibitors of cysteine proteinases including cathepsins B, H and L. Biochem J. 1982; 201:189-198
21. Matsumoto K, Mizoue K, Kitamura K et al. Structural basis of inhibition of cysteine proteases by E-64 and its derivatives. Biopolymers. 1999; 51:99-107

Example 2

Novel Cystatin C Cleavage Site in Patients with Multiple Sclerosis

We examined The effect of storage and freeze thaw cycles on cystatin C was examined in CSF. As described in detail below, this resulted in cleavage of the cystatin C at eight amino acids from the N terminal and a resulting loss in its effect on cathepsin B activity. In contrast, a distinct smaller peak was noted in the CSF of patients with remitting relapsing Multiple Sclerosis resulting from the cleavage of eight amino acids from the C terminal region of the protein. When recombinant cystatin C was cleaved the C terminal region, an enhancement of the cystatin C activity was noted. Thus the cystatin C fragment in patients with Multiple Sclerosis is molecularly and functionally distinct.

Figure 7:
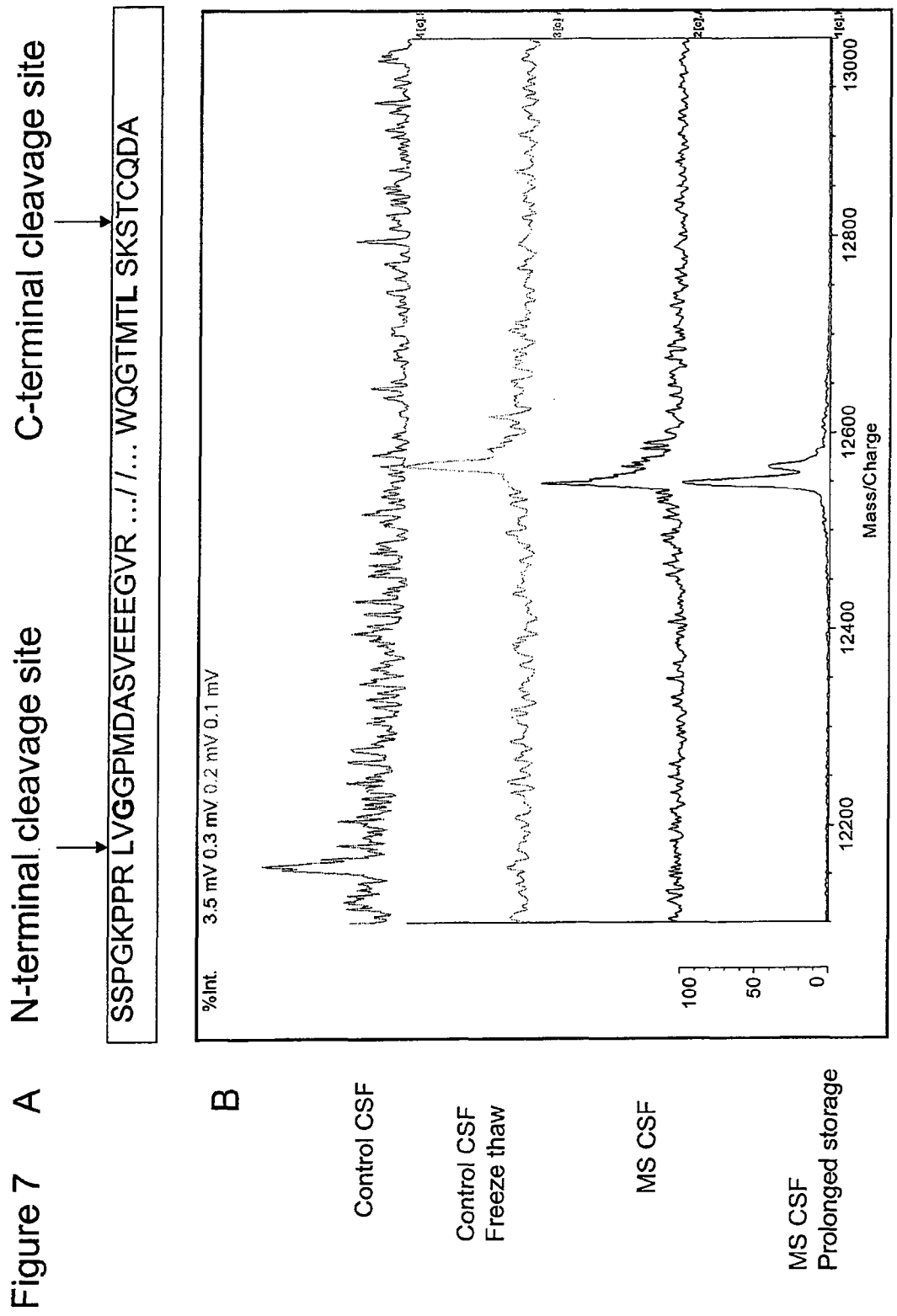
FIG. 7 shows N and C terminal cleavage of cystatin C. (A) Site of cleavage of cystatin C at the N terminal fragment between the arginine and lysine residues and at the C terminal region between the lysine and seine residues are marked by arrows. (B) Tracings obtained from CSF analysis on Axima CFR MALDI-TOF mass spectrometer are shown. The control CSF shows the absence of any peaks at 12.5 kD, however, following repeated freeze thaws the same CSF sample has a peak at M/Z of 12,543 which corresponds to cystatin C following N terminal cleavage. In contrast CSF from the MS patient shows a peak at M/Z of 12,527 which corresponds to cystatin C following C terminal cleavage. Following prolonged storage, the CSF from the MS patient acquired a new peak corresponding to cystatin C following N terminal cleavage while the previous peak remains unchanged

Protein cleavage occurs via proteases that are abundant in biological fluids. These proteases can be differentially regulated in disease states. For example, both matrix metalloproteases (MMPs) (5, 6) and cathepsins (7) have been shown to be altered in patients with remitting relapsing MS. All CSF samples used in our work were centrifuged immediately upon collection and then frozen at −80° C. within 2 hours until used for this analysis. Each sample was collected from the same clinic at our institution and handled and stored by the personnel in our laboratories using the same protocol. We examined the endogenous degradation of cystatin C. No changes in cystatin C were noted for up to 4 hours at room temperature. While cleavage of cystatin C was noted by leaving the sample overnight, no changes were noted in the protein with heating at 60° C. for one hour. Hansson et al., Del Biccio et al., and Carrette et al., showed that prolonged storage of CSF at −20° C. can result in cleavage of cystatin C (8, 32) at the eight amino acid N terminus. As shown by MALDI analysis, the cleavage site we identified as unique to remitting relapsing MS patients was at the C terminal region of the protein. A tryptic digest of the 12.5 kD protein that we isolated contained the N terminal peptide (see FIG. 7). There was no trypsin cleavage site in the C-terminal region of the 13.4 kD cystatin C that would yield a fragment of a similar size. Hence we were certain that the cleavage of cystatin C in patients with MS occurs at the C terminal region (FIG. 7). This suggested that the mechanism of cystatin C cleavage in MS and upon prolonged storage may be different and that the proteases responsible for these different cleavage events may also be different. To further explore this possibility, we have performed several additional experiments to examine the effects of freeze thaw cycles and various proteases on cystatin C cleavage and function.

Effect of Freeze Thaw of CSF on Cystatin C Cleavage

A CSF sample from a control patient who had only the 13.4 kD peak was subjected to seven freeze thaw cycles and another CSF sample from patient with remitting relapsing MS who had the 12.5 kD peak was stored at −20° C. for 4 months and reanalyzed by Axima CFR MALDI-TOF mass spectrometer (Kratos, Manchester, UK). Two microliters of the desalted solution were spotted on a stainless steel plate via the sandwich layering method with 0.64 saturated alpha-cyanto-4-hydroxycinnamic acid in 50% acetonitrile/50% 0.1% trifluoroacetic acid. 100 profiles containing 10 shots each were acquired for all sample spots. A new peak at M/Z of 12,543.3 emerged in the control CSF which corresponds to the N terminal cleavage product of cystatin C. The MS CSF had a peak at M/Z 12,527.6 which corresponds to the C-terminal cleavage product of cystatin C. Following prolonged storage, both the N terminal and the C-terminal products are noted (FIG. 7). These findings conclusively demonstrate that the cleavage site of cystatin C in CSF of MS patients is different than that seen by prolonged storage and by freeze thaw cycles.

Effect of Protease Inhibitors on Cystatin C Cleavage

Figure 8:
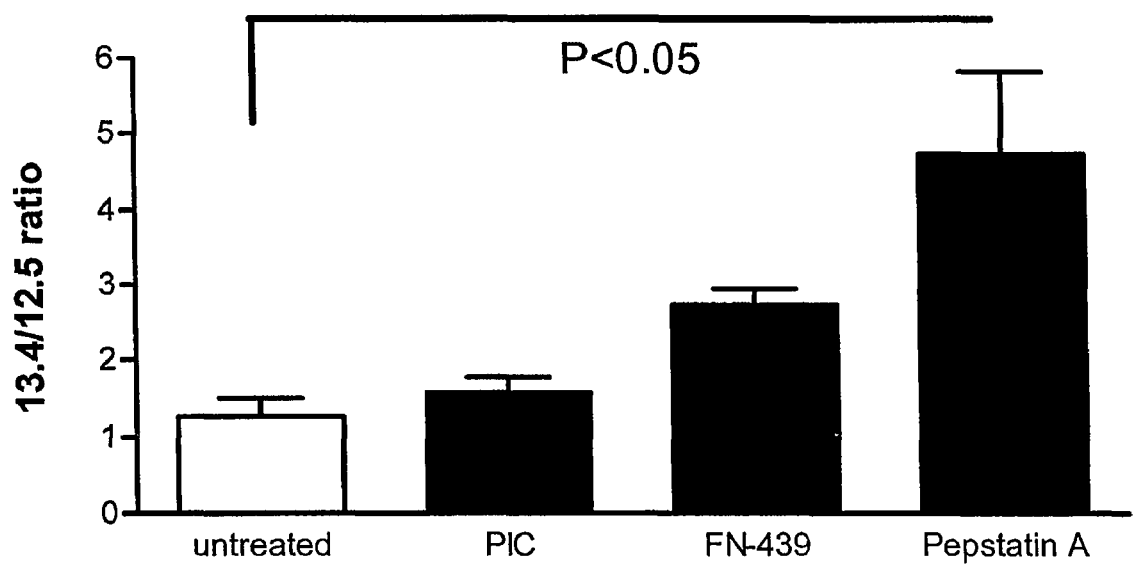
FIG. 8 shows inhibition of cystatin C cleavage by pepstatin A. A CSF sample that had only the 13.4 kD peak was incubated with a protease inhibitor cocktail (PIC), a MMP inhibitor (FN439) or a cathepsin D inhibitor (pepstatin A) for 48 hours at room temperature. Only, papstatin A significantly prevented cleavage of cystatin C

Since the N-terminal cleavage of cystatin C occurs at a tryptic site (R-L) and the C-terminal cleavage occurs at a cathepsin D cleavage site (9), we proposed the degradation to be protease dependent. We incubated control CSF which contained only the full length cystatin C at room temperature for 48 hours in the presence of various protease inhibitors and monitored it for the presence of the 12.5 kD fragment. As seen in FIG. 8, the protein inhibitor cocktail (Sigma) had no significant effect on the cleavage of cystatin C, while both FN-439 (500 ug/ml), a MMP specific inhibitor, and pepstatin A (500 ug/ml), a cathepsin D specific inhibitor, showed inhibition of the breakdown of cystatin C.

Inhibition of cathepsin B by cystatin C cleavage products

Figure 9:
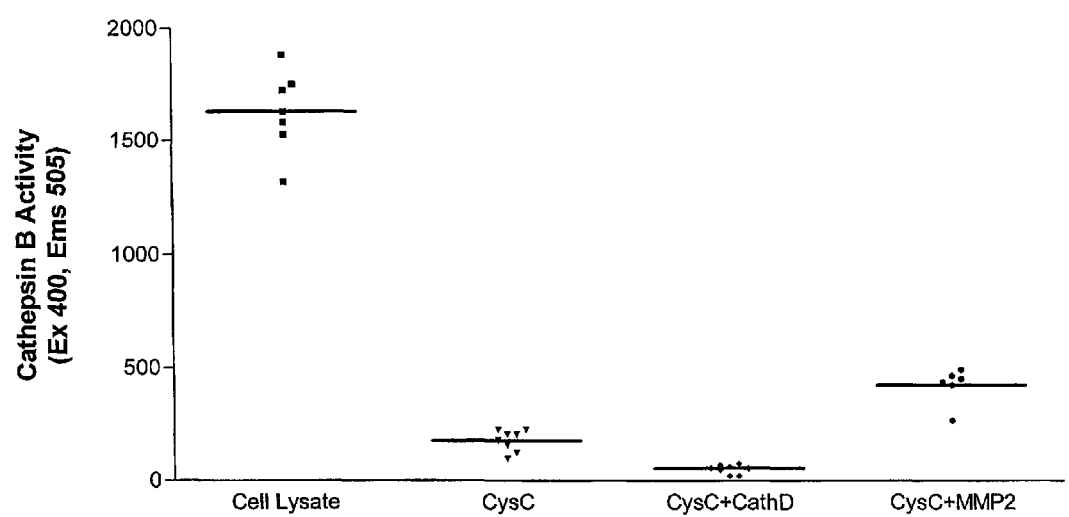
FIG. 9 shows modulation of cystatin C activity by cathepsin D and MMP-2. Recombinant cystatin C (CysC) shows significant inhibition of cathepsin B activity (P<0.01), which is further enhanced by treatment with cathepsin D (CathD). In contrast, treatment with MMP-2 shows an inhibition of CysC activity
Figure 13A:
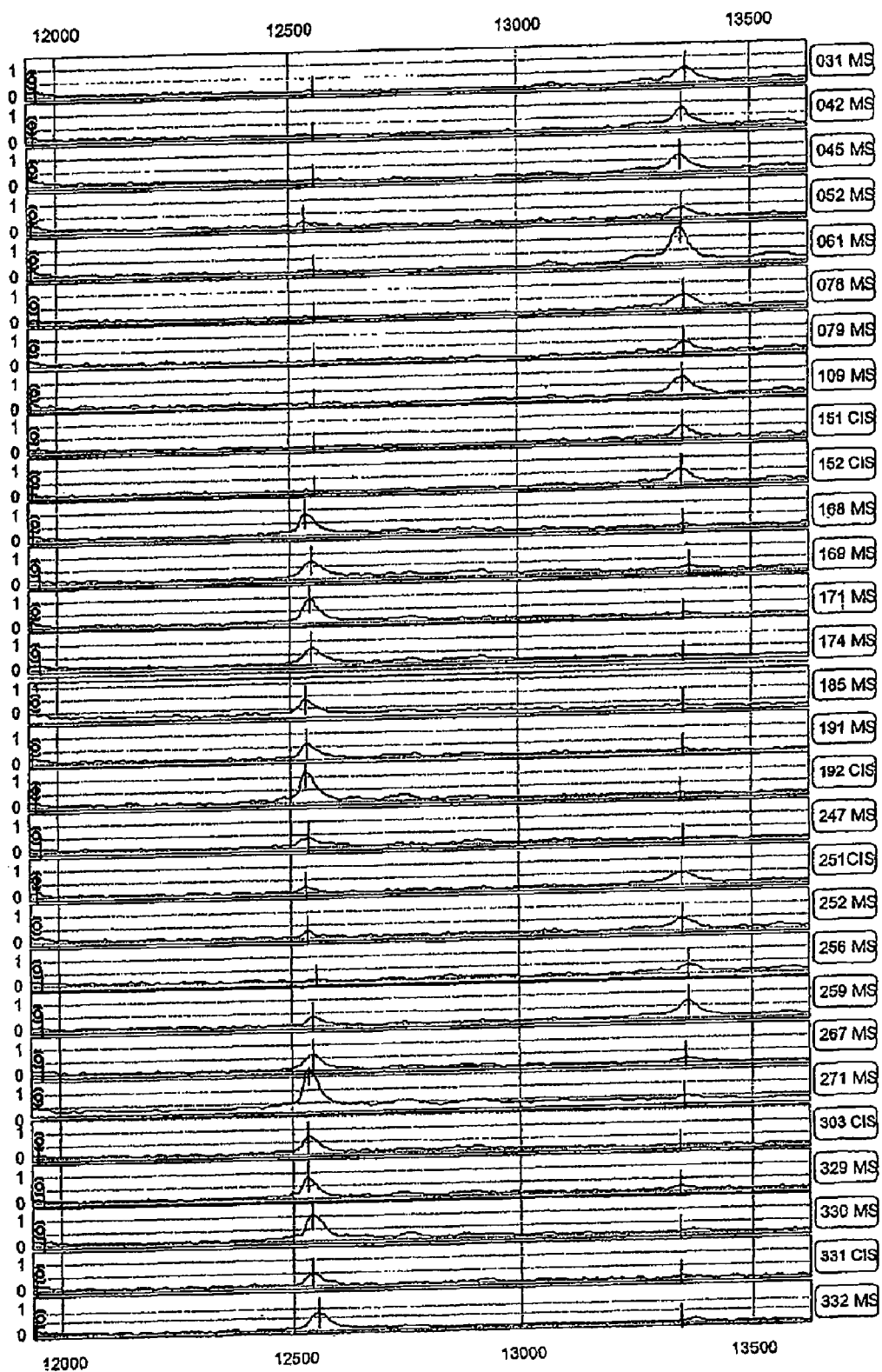
FIG. 13 shows cerebrospinal fluid spectra generated by surface-enhanced laser desorption/ionization analysis. (A) Patients with multiple sclerosis (MS) or clinically isolated syndromes (CIS) show either a prominent peak at 12.5 kDa, 13.4 kDa or blunted peaks at both molecular masses. (B) The 12.5 kDa peak is absent from control patients with other neurological diseases (OND). However, the 13.4 kDa peak is prominent. The scales in A and B are identical.
Figure 13B:
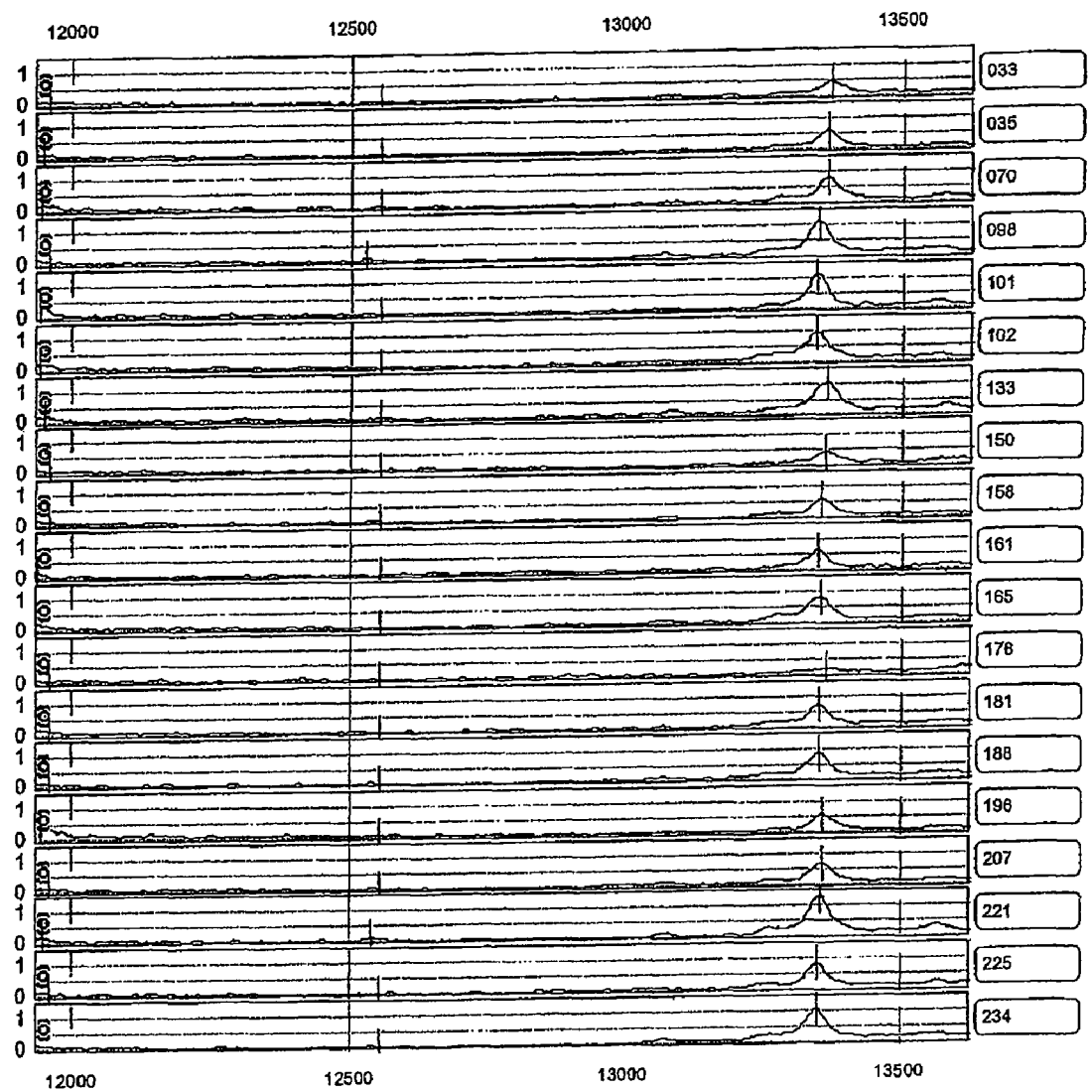
Figure 14:
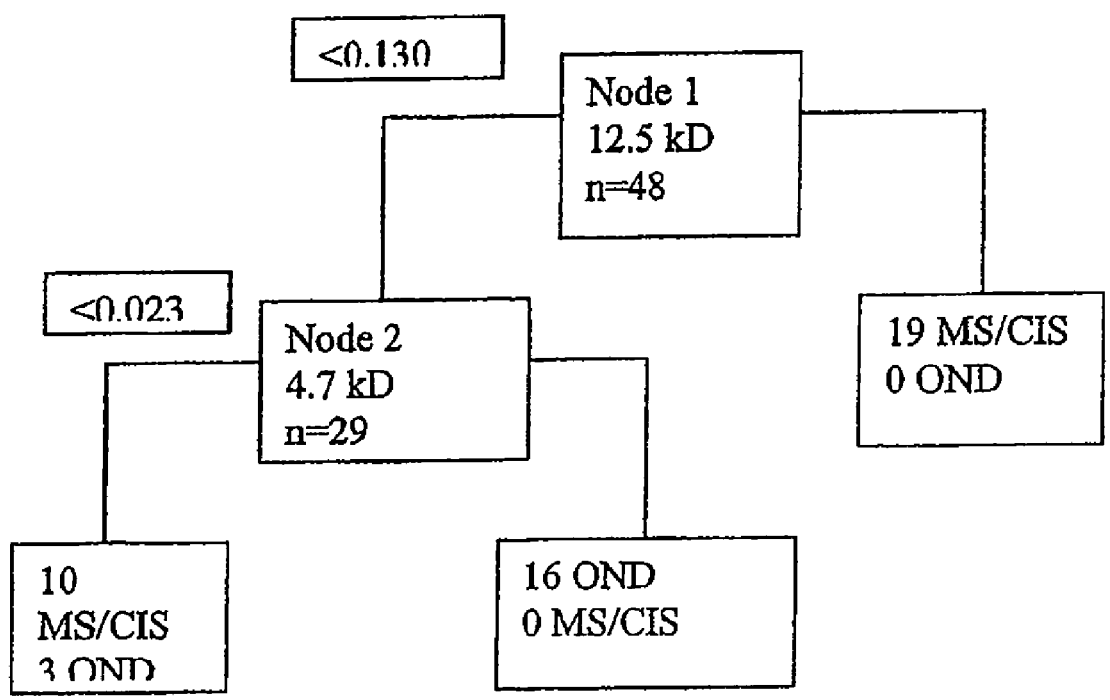
FIG. 14 shows a decision tree for identifying patients with MS. For the purpose of this analysis, MS and CIS patients were analyzed as a single group. BPS analysis of 2 1 7 clusters shows that the 12.5 kDa peak was the top splitter that correctly identified 19 of 29 MS/CIS patients. Of the remaining 29 samples, the 4.7 kDa peak correctly identified 16 OND patients. 3 of the OND patients but none of the MS/CIS patients were misclassified.
Figure 15:
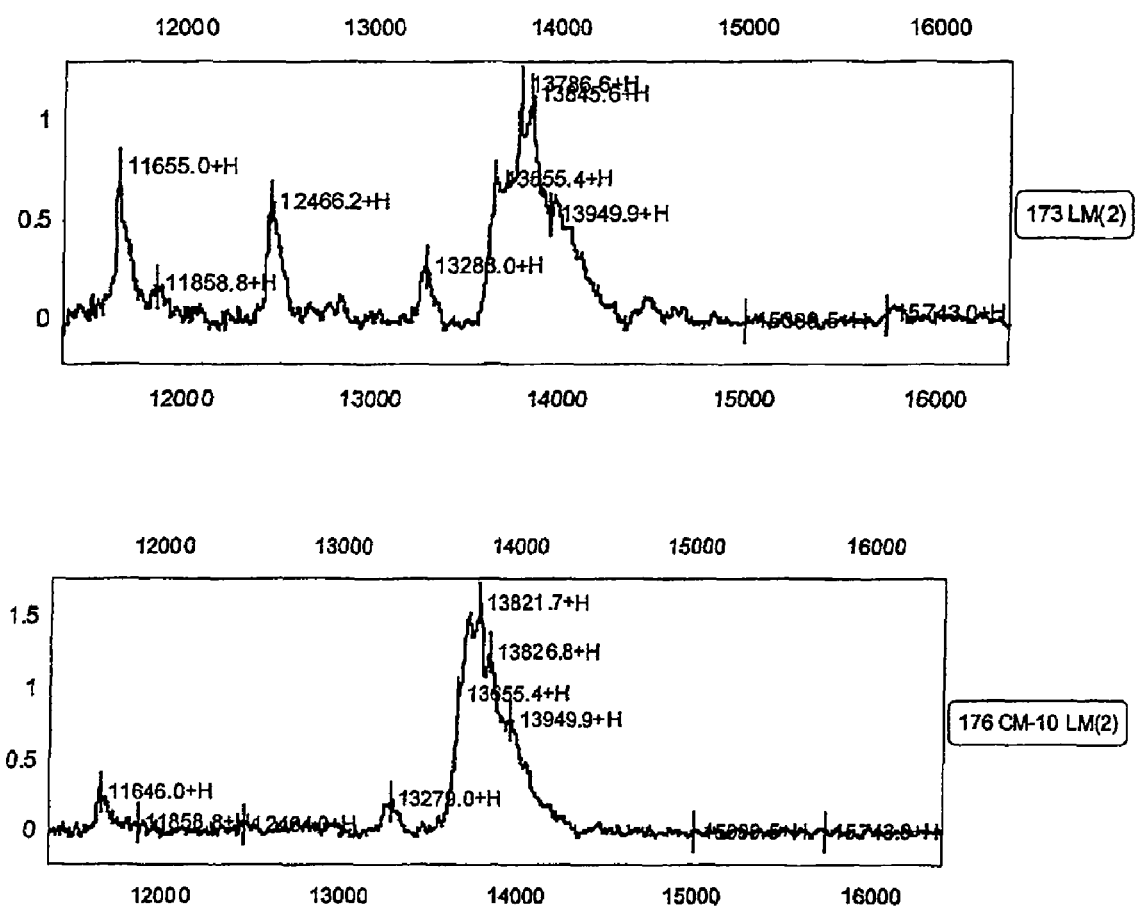
FIG. 15 shows the results of an analysis of CSF from patients with Multiple Sclerosis. A CM-10 chip was pre-equilibrated with 100 mM sodium acetate pH=4. A ¹/₁₀ dilution of CSF in 100 mM sodium acetate ph=4 and a final volume of 150 μL was put on each spot. Duplicate spots were used for each patient and incubated for 1 hour at room temperature. The chips were washed with binding buffer+0.1% Triton X100 and then rinsed with ultrapure water. The chip was air-dried and SPA applied as the EAM. The chips were "read" on a calibrated ProteinChip System (PBS11c; Ciphergen Biosystems, Inc.) at a laser intensity of 175 with the detector sensitivity at 6. Chips were also read at a higher laser intensity of 190 and mass deflector sensitivity at 8 to help detect higher mass proteins. A representative spectrum from a patient with multiple sclerosis shows a unique peak at 12.4 kD (upper panel), while it was absent in the patients with normal pressure hydrocephalus (lower panel).
Figure 18:
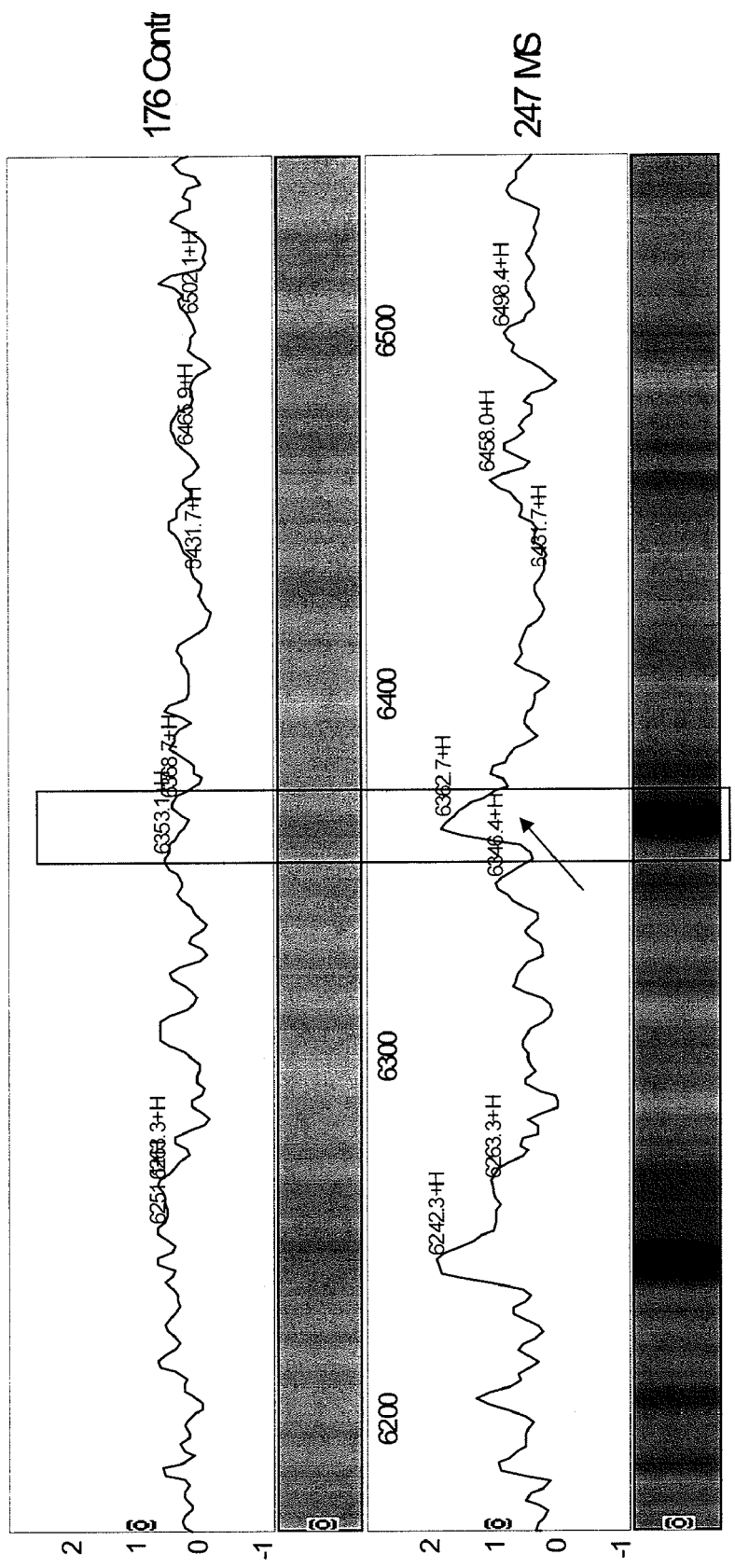
FIG. 18 shows a spectrum that shows one of the peaks listed in Table 4A.

Recombinant cystatin C was produced and the ability of MMP-2 and cathepsin D to cleave the recombinant protein was confirmed. As expected, cathepsin D cleaved cystatin C at four different sites, and yielded a 12.5 kD fragment following cleavage from the C terminal region (9). In contrast, MMP-2 cleaved cystatin C at three unique sites (GK, FC, and GT which correspond to amino acids 4,5; 96,97 and 108,109). Recombinant cystatin C was treated with either MMP-2 or cathepsin D and its activity monitored by a cathepsin B functional assay using a kit from Biovision Research Products, Mountain View, Calif. The assay was performed as previously described (4). As expected, full length cystatin C showed significant inhibition of cathepsin B. Treatment of cystatin C with cathepsin D showed further decrease in cathepsin B activity; in keeping with our previous observation that CSF of MS patients with the 12.5 kD fragment also showed a similar enhancement of cystatin C activity. In contrast treatment of cystatin C with MMP-2 lead to a decrease in its ability to inhibit cathepsin B activity. Cathepsin D and MMP-2 alone had no effect on cathepsin B activity (FIG. 9). These observations confirmed that C terminal fragmentation of cystatin C leads to a gain in activity while cleavage in other regions including the N terminal region leads to a loss or decrease of activity of cystatin C.

Our observations were consistent with those of other laboratories (38) that suggested that prolonged storage of CSF at −20° C. can result in N terminal cleavage of cystatin C. We have further extended these observations to show that incubation of CSF at room temperature for several hours and repeat freeze thaw cycles can also result in a similar cleavage of cystatin C. Thus, we suggest that for proteomics studies of the CSF, cell free CSF be collected following centrifugation to remove cells and the CSF be aliquoted and stored at −80° C. Close attention is also needed to the time interval between CSF collection and storage.

The unique observation made in our study was that in some patients with remitting relapsing MS, cleavage of cystatin C may occur from the C terminal region. This cleavage product also has an apparent mass of 12.5 kD which is similar to the mass of the fragment generated by N terminal cleavage and the resolution of the mass spectrometer by Ciphergen is not sufficient to clearly distinguish between the two peaks. This may explain the rather broad base of the peaks seen by both Nakashima et al., and Hansson et al., which could represent the combination of the N and C terminal products (13). In contrast, the peaks that we found with the CM10 chip were sharper, much larger and more distinct. We further used an Axima CFR MALDI-TOF mass spectrometer to distinguish between the two peaks, since this instrument provides a much greater mass accuracy. We found that the N terminal cleavage product had a measured mass of 12,543.3 Daltons while the C-terminal region had a measured mass of 12,527.6 Daltons and they could be clearly distinguished as separate peaks in the same CSF sample. We have further identified that cathepsin D can cleave full-length cystatin C to yield the C terminal fragment and that such cleavage changes its functional properties. Interestingly, upon C terminal cleavage, the inhibitory properties of cystatin C are enhanced. In contrast N terminal cleavage results in the loss of its functional properties.

In summary, based on these data, we conclusively showed that a unique C terminal fragment of cystatin C can be found in some patients with remitting relapsing MS.

REFERENCES

1. Nakashima I, Fujihara K, Fujinoki M et al. Alteration of Cystatin C in the cerebrospinal fluid of multiple sclerosis. Ann Neurol. 2006
2. Del Biccio P, Pieragostino D, Lugaresi A et al. Cleavage of cystatin C is not associated with multiple sclerosis. Ann Neurol. 2006
3. Hansson S F, Hviid-Simonsen A, Zetterberg H et al. Cystatin C in Cerebrospinal Fluid and Multiple Sclerosis. Ann Neurol. 2006
4. Irani D N, Anderson C, Gundry R et al. Cleavage of cystatin C in the cerebrospinal fluid of patients with multiple sclerosis. Ann Neurol. 2006; 59:237-247
5. Fainardi E, Castellazzi M, Bellini T et al. Cerebrospinal fluid and serum levels and intrathecal production of active matrix metalloproteinase-9 (MMP-9) as biomarkers of disease activity in patients with multiple sclerosis. Mult Scler. 2006; 12:294-301
6. Kanesaka T, Mori M, Hattori T et al. Serum matrix metalloproteinase-3 levels correlate with disease activity in relapsing-remitting multiple sclerosis. J Neurol Neurosurg Psychiatry. 2006; 77:185-188
7. Roberts R. Lysosomal cysteine proteases: structure, function and inhibition of cathepsins. Drug News Perspect. 2005; 18:605-614
8. Carrette O, Burkhard P R, Hughes S et al. Truncated cystatin C in cerebrospiral fluid: Technical [corrected] artefact or biological process? Proteomics. 2005; 5:3060-3065
9. Lenarcic B, Krasovec M, Ritonja A et al. Inactivation of human cystatin C and kininogen by human cathepsin D. FEBS Lett. 1991; 280:211-215.

Example 3

Exemplary Modified Terpenoids are Neuroprotective against an Oxidative Stressor and a Neurotoxic Protein We sought to evaluate the protective efficacy of a number of modified terpenoid compounds against the against many different neurotoxins, ranging from the chemotoxic 6-OHDA, NMDA, 3-nitropropionic acid (3-NP), and viral proteins such as Tat and gp120. Thus, we established an in vitro neuroprotection assay using rat mixed hippocampal cultures, in which we evaluated the protective efficacy of neuroprotective compounds disclosed herein. The oxidative stressor 3-NP was used to elicit toxicity in the rat hippocampal cultures to mimic the oxidative damage, reactive oxygen species production and ensuing neurodegeneration resulting from HIV infection.

Another measure of neurotoxicity which results from HIV infection was evaluated by exposure of the hippocampal cultures to HIV-1 Tat (Li et al (2005), *Neurotox Res,* 8(1-2):119-134).

Rat mixed hippocamal neuronal cultures were generated from freshly dissected rat hippocampi (embryonic day 18) in neurobasal media containing 5% fetal bovine serum and 2% B27 supplement. The cells were plated into 96 well plates at a density of $4 \times 10^5$ cells/mL and routinely used on days 11-14 following culturing. Cell viability was assessed with MTT [3-(4,5-dimethylthiazol-2-yl)-2,5-diphenyltetrazolium bromide] assay. The MTT assay is based on the ability of a mitochondrial dehydrogenase enzyme from viable cells to cleave the tetrazolium rings of the pale yellow MTT and form dark blue formazan crystals. See Mosmann (1983), *J Immunol Methods,* 65(1-2):55-63. These crystals are largely impermeable to cell membranes, and thus accumulate within healthy cells. The resultant formazan precipitates are solubilized with DMSO and read on a multiwell scanning spectrophotometer (ELISA reader). The number of surviving cells is directly proportional to the level of the formazan product created.

Mixed hippocampal cultures were incubated with 3-NP (0.5-10 mM) for 18 hours and then assessed for viability using an MTT assay. Titration of 3-NP levels for neurotoxic effects demonstrated that 3 mM 3-NP treatment consistently induced 25-35% cytotoxicity in rat mixed hippocampal cultures.

The assay system was validated using two neuroprotective agents, GPI 1046 and Resveratrol. Both of these compounds have demonstrated antioxidant and/or neuroprotective activities in numerous in vitro and in vivo assays (for review, see Poulter et al. (2004), *Neuroscience,* 128(1):1-6; Caporello, et al. (2006), *J Neurochem,* 98(1):146-155; Zamin et al. (2006), *Neurobiol Dis,* 24(1):176-182). Cultures were preincubated with GPI 1046 or Resveratrol for one hour prior to an 18 hour exposure to 3 mM 3-NP. These "positive control" neuroprotective compounds significantly protected rat neurons from oxidative damage elicited by 3-NP in the rat mixed hippocampal culture assay system described above. The same neuroprotective compounds were evaluated for efficacy against HIV-1 Tat protein toxicity using the same 1 hour preincubation protocol. As with the 3-NP neurotoxicity assay, these compounds protected hippocampal neurons from Tat toxicity as well. These findings indicated that the measurement of neuroprotection against 3-NP toxicity likely serves as a good indicator of protective activity against HIV-1 Tat toxicity.

We tested in the in vitro neuroprotection assay the modified terpenoids of Formula I listed in Table 5. As shown in Tables 5, a number of modified terpenoid compounds were identified as having neuroprotective activity against 3-NP.

Gedunin and Limonin also dose dependently protected hippocampal cultures from HIV-1 Tat toxicity, with nearly complete neuroprotection provided by 1-10 μM Gedunin. Thus, some modified terpenoids also protect hippocampal neurons from HIV-1 neurotoxic protein degeneration.

We also tested the ability of Limonin to protect against N-methyl-D-Aspartic Acid (NMDA) excitotoxicity, and 6-Hydroxydopamine (6-0HDA), a dopaminergic neurotoxin. Limonin dose-dependently blocked the neurotoxicity of both NMDA and 6-OHDA conferring complete protection at the highest Limonin dose tested (10 μM).

Finally, we sought to determine if the compounds tested in rat neuronal cultures would also be effective on cultured human fetal neurons. Indeed, Limonin dose-dependently protected human fetal neuronal cultures against both 3-NP and 6-OHDA.

Based on these data, we concluded that various modified terpenoid compounds are neuroprotective and are candidate therapeutic compounds for use in the treatment of MS and related disorders.

The examples and embodiments described herein are for illustrative purposes only and various modifications or changes are within the spirit and purview of this application and scope of the appended claims. All publications, patents, and patent applications cited herein are hereby incorporated by reference for all purposes.

What is claimed is:

1. A method for diagnosis of multiple sclerosis in a subject, that comprises (i) determining in a biological sample from the subject the level of full length cystatin C protein and the level of a cystatin C protein fragment lacking 8 amino acids at its C-terminus; and (ii) determining the ratio of the fragment to full length cystatin C protein in the biological sample; and (iii) comparing the ratio obtained in (ii) with a corresponding control ratio determined from a control subject; wherein a ratio determined in step (ii) that is greater than the control ratio indicates a diagnosis of multiple sclerosis.

2. The method of claim 1, wherein the biological sample is a cerebrospinal fluid or blood sample.

3. The method of claim 1, wherein the determining comprises performing mass spectroscopy on the biological sample and indicating the peak corresponding to the cystatin C protein fragment and the peak corresponding to the full length cystatin C protein.

4. The method of claim 1, that further comprises performing a cathepsin B activity assay on at least a fraction of the biological sample.

5. A method for optimizing multiple sclerosis treatment of a subject in need thereof, that comprises (i) obtaining a first biological sample from the subject; (ii) determining the ratio of the level of a cystatin C protein fragment lacking 8 amino acids at its C terminus to the level of full length cystatin C protein in the first biological sample; (iii) providing a multiple sclerosis treatment to the subject; (iv) obtaining a second biological sample from the subject; (v) determining the ratio of the fragment to the full length cystatin C protein in the second biological sample; and (vi) altering the treatment if the ratio in the second biological sample is greater than the ratio in the first biological sample; or maintaining the treatment unaltered if the ratio in the second biological sample is equal to or less than the ratio in the first biological sample.

* * * * *